US012649905B2

(12) United States Patent
Zhao et al.

(10) Patent No.: US 12,649,905 B2
(45) Date of Patent: Jun. 9, 2026

(54) METHODS FOR TREATING AN IMMUNE DISORDER-RELATED DISEASE BY REDUCING AUTOREACTIVITY IN A T CELL COMPARTMENT

(71) Applicant: Hackensack University Medical Center, Hackensack, NJ (US)

(72) Inventors: Yong Zhao, River Edge, NJ (US); Robert Korngold, Wayne, NJ (US); Michele Donato, Livingston, NJ (US)

(73) Assignee: Hackensack University Medical Center, Hackensack, NJ (US)

( * ) Notice: Subject to any disclaimer, the term of this patent is extended or adjusted under 35 U.S.C. 154(b) by 0 days.

(21) Appl. No.: 15/689,979

(22) Filed: Aug. 29, 2017

(65) Prior Publication Data

US 2018/0057797 A1     Mar. 1, 2018

Related U.S. Application Data

(60) Provisional application No. 62/380,904, filed on Aug. 29, 2016.

(51) Int. Cl.
| | |
|---|---|
| *C12N 5/071* | (2010.01) |
| *A61K 35/12* | (2015.01) |
| *A61K 35/14* | (2015.01) |
| *A61K 35/15* | (2025.01) |
| *C12N 5/073* | (2010.01) |
| *C12N 5/0783* | (2010.01) |
| *C12N 5/0786* | (2010.01) |

(52) U.S. Cl.
CPC ............ *C12N 5/0692* (2013.01); *A61K 35/15* (2013.01); *C12N 5/0605* (2013.01); *C12N 5/0636* (2013.01); *C12N 5/0645* (2013.01); *A61K 2035/122* (2013.01); *A61K 35/14* (2013.01); *C12N 2501/125* (2013.01); *C12N 2501/51* (2013.01); *C12N 2501/515* (2013.01); *C12N 2501/599* (2013.01); *C12N 2502/025* (2013.01); *C12N 2502/1107* (2013.01); *C12N 2502/1114* (2013.01); *C12N 2502/1157* (2013.01); *C12N 2502/1164* (2013.01); *C12N 2506/11* (2013.01)

(58) Field of Classification Search
CPC .. C12N 5/0692; C12N 5/0645; C12N 5/0636; A61K 35/14; A61K 2035/122; A61K 35/15; A61P 43/00; A61P 37/02; A61P 37/00; A61P 3/10
See application file for complete search history.

(56) References Cited

U.S. PATENT DOCUMENTS

| | | | |
|---|---|---|---|
| 4,520,110 A | 5/1985 | Stryer et al. |
| 4,714,680 A | 12/1987 | Civin |
| 4,859,582 A | 8/1989 | Stryer et al. |
| 4,876,190 A | 10/1989 | Recktenwald |
| 4,965,204 A | 10/1990 | Civin |
| 5,035,994 A | 7/1991 | Civin |
| 5,055,556 A | 10/1991 | Stryer et al. |
| 5,187,083 A | 2/1993 | Mullis |
| 5,187,288 A | 2/1993 | Kang et al. |
| 5,234,824 A | 8/1993 | Mullis |
| 5,286,486 A | 2/1994 | Payne et al. |
| 5,333,675 A | 8/1994 | Mullis et al. |
| 5,486,616 A | 1/1996 | Waggoner et al. |
| 5,569,587 A | 10/1996 | Waggoner |
| 5,569,766 A | 10/1996 | Waggoner et al. |
| 5,627,027 A | 5/1997 | Waggoner |
| 5,637,677 A | 6/1997 | Greene et al. |
| 5,656,493 A | 8/1997 | Mullis et al. |
| 5,723,218 A | 3/1998 | Haugland et al. |
| 5,776,709 A | 7/1998 | Jackson et al. |
| 2008/0299090 A1 | 12/2008 | Weiss et al. |
| 2011/0256110 A1 | 10/2011 | Perin et al. |

(Continued)

FOREIGN PATENT DOCUMENTS

| | | |
|---|---|---|
| CA | 1179942 A | 12/1984 |
| CN | 1918287 A | 2/2007 |
| CN | 101326280 A | 12/2008 |

(Continued)

OTHER PUBLICATIONS

Schwendemann et al. Dynamic Differentiation of Activated Human Peripheral Blood CD8+ and CD4+ Effector Memory T Cells. The Journal of Immunology. 2005;175:1433-1439.*

Sallusto et al., Two subsets of memory T lymphocytes with distinct homing potentials and effector functions. Nature, vol. 401 (1999) pp. 708-712. (Year: 1999).*

Delgado et al., Modulation of autoimmune T-cell memory by stem cell educator therapy: phase 1/2 clinical trial. EBioMedicine, vol. 2, No. 12 (Dec. 2015) pp. 2024-2036. (Year: 2015).*

Lee et al., Comparison of surface markers between human and rabbit mesenchymal stem cells. PLoS One, vol. 9, No. 11 (2014) pp. 1-10. (Year: 2014).*

(Continued)

*Primary Examiner* — Kara D Johnson
(74) *Attorney, Agent, or Firm* — Beverly W. Lubit; Bochner PLLC

(57) ABSTRACT

The described invention provides a pharmaceutical composition comprising a therapeutic amount of an educated mononuclear cell product, a process for preparing the educated mononuclear cell product, and a method for treating a disease characterized by lymphocyte autoreactivity. Mononuclear cells from a diseased subject are co-cultured with a viable population of adherent umbilical cord blood stem cells at at least 80% confluence to form an educated mononuclear cell product. A therapeutic amount of the educated mononuclear cell product is returned by infusion intravascularly to the subject. The therapeutic amount is effective to modulate autoreactivity in a T cell compartment of the subject and to reduce symptoms of the disease characterized by lymphocyte autoreactivity.

5 Claims, 14 Drawing Sheets
(10 of 14 Drawing Sheet(s) Filed in Color)

(56)                 References Cited

U.S. PATENT DOCUMENTS

2012/0277652 A1*  11/2012  Zhao ................... A61M 1/3472
                                                      604/6.01

FOREIGN PATENT DOCUMENTS

CN        104721232 A     6/2015
CN        105154399 A    12/2015
EP             76695 A1    4/1983

OTHER PUBLICATIONS

Nguyen et al., "Approach to flow cytometry: General consider-
ations." in: Flow cytometry in Hematopathology: A visual approach
to data analysis and interpretation. 2nd Ed. (Human Press, Totowa,
New Jersey, 2007), pp. 1-12. Z39.48-1984. (Year: 2007).*
Huang Y. et al., "Defining CD59-C9 binding interaction", J. Biol.
Chem., vol. 281(37): 27398-27404, (2006).
Hugues S. et al., "Tolerance to Islet Antigens and Prevention from
Diabetes Induced by Limited Apoptosis of Pancreatic b Cells";
Immunity, 16:169-181, (2002).
Jagannathan-Bogdan M. et al., "Elevated proinflammatory cytokine
production by a skewed T cell compartment requires monocytes and
promotes inflammation in type 2 diabetes", J Immunol, vol. 186:
1162-1172, (2011).
Janeway, CA, Jr., "The priming of helper T cells", Semin. Immunol.,
vol. 1(1): 13-20 (1989).
Jellis C. L. et al., "Genomic organization of the gene coding for the
costimulatory human B-lymphocyte antigen B7-2 (CD86)",
Immunogenetics, vol. 42: 85-89, (1995).
Jiang T.T., "Regulatory T cells: new keys for further unlocking the
enigma of fetal tolerance and pregnancy complications", J Immunol.,
vol. 192(11): 4949-4956, (2014).
Kaplan R. et al., "Cloning of three human tyrosine phosphatases
reveals a multigene family of receptor-linked protein-tyrosine-
phosphatases expressed in brain", Proc. Natl. Acad. Sci. U.S.A, vol.
87(18): 7000-7004, (1990).
Kiecker C. et al., "Molecular specification of germ layers in
vertebrate embryos", Cell Mol Life Sci., Mar. 2016, 73(5):923-47,
doi: 10.1007/s00018-015-2092-y. Epub Dec. 14, 2015.
Kim W. S. et al., "The pivotal role of PDGF and its receptor
isoforms in adipose-derived stem cells", vol. 30(7), 793-799 (2015).
Klein L., "Aire gets company for immune tolerance", Cell, vol.
163(4):794-795, (2015).
Klingemann, H., et al, Autologous Stem Cell Transplant Recipients
Tolerate Haploidentical Related-Donor Natural Killer Cell Enriched
Infusions. Transfusion, Feb. 16, 2013, Epub 28, Jun. 2012, vol. 53,
No. 2, 412-418.
Kohn L. A. et al., "Lymphoid priming in human bone marrow
begins before expression of CD10 with upregulation of L-selectin",
Nat. Immunol., vol. 13(10): 963-971, (2012).
Kornete M. et al., "Th1-Like ICOS+ Foxp3+ Treg Cells Preferen-
tially Express CXCR3 and Home to ?-Islets during Pre-Diabetes in
BDC2.5 NOD Mice", PLoS One. , vol. 10(5): 1-16, (2015).
Kronenberg, M. et al., "Regulation of immunity by self-reactive T
cells", Nature, vol. 435: 598-604 (2005).
Kumar N.P. et al.; Coincident diabetes mellitus modulates Th1-,
Th2-, and Th17-cell responses in latent tuberculosis in an IL-10- and
TGF-?-dependent manner; doi: 10.1002/eji.201545973; Eur. J. Immunol,
46:390-399 (2016).
Leahy D. J. et al., "Crystal structure of a soluble form of the human
T cell coreceptor CD8 at 2.6 A resolution", Cell, vol. 68(6):
1145-62, (1992).
Lehuen A. et al., "Immune cell crosstalk in type I diabetes", Nat Rev
Immunol. vol. 10: 501-513, (2010).
Li X. et al., "Fibroblast growth factors, old kids on the new block",
Semin Cell Dev Biol., 53: 155-167 (2016).
Li Y. et al., "Inflammatory signaling regulates embryonic hematopoietic
stem and progenitor cell production", Genes Dev., vol. 28(23):
2596-2612, (2014).

Loetscher P. et al., "The ligands of CXC chemokine receptor 3,
I-TAC, Mig, and IP10, are natural antagonists for CCR3", J. Biol.
Chem., vol. 276: 2986-2991, (2001).
MacDonald P.E. et al., "The multiple actions of GLP-1 on the
process of glucose-stimulated insulin secretion", Diabetes, vol. 51
(Suppl. 3): S434-S442, (2002).
MacKay C.R., "Chemokines: immunology's high impact factors",
Nat Immunol., vol. 2: 95-101, (2001).
Marion G. Macey, Flow cytometry: principles and applications,
Humana Press, 2007 (16 Pages).
Mathieu C. et al., "Arresting type I diabetes after diagnosis: GAD
is not enough", Lancet, vol. 378: 291-292, (2011).
Matteucci, E., et al., "Altered proportions of naïve, central memory
and terminally differentiated central memory subsets among CD4+
and CD8+ T cells expressing CD26 in patients with type 1 diabe-
tes", J. Clin. Immunol, vol. 31: 977-984, (2011).
Metzger T.C. et al., "Control of central and peripheral tolerance by
Aire", Immunol. Rev. 2011, vol. 241: 89-103, (2011).
Mihu C. et al., "Isolation and characterization of stem cells from the
placenta and the umbilical cord", Romanian Journal of Morphology
and Embryology, 2008, 49(4):441-446, (2008).
Mojsov S. et al, "Preproglucagon gene expression in pancreas and
intestine diversifies at the level of post-translational processing", J.
Biol. Chem., vol. 261: 11880-11889 (1986).
Moschovakis G.L. et al., "Multifaceted activities of CCR7 regulate
T-cell homeostasis in health and disease", Eur J Immunol, vol. 42:
1949-1955, (2012).
Munn D. et al., "Inhibition of T cell proliferation by macrophage
tryptophan catabolism", J Exp Med, vol. 189: 1363-1372, (1999).
Munn D. et al., "Prevention of allogeneic fetal rejection by trypto-
phan catabolism", Science, vol. 281: 1191-1193, (1998).
Murphy, Kenneth; Janeway's Immunobiology: 8th Ed., Chapter 15,
pp. 611-668: Garland Science (2012).
Najar M. et al., "Mesenchymal stromal cells and immunomodula-
tion: A gathering of regulatory immune cells", Cytotherapy, vol.
18(2): 160-171, (2016).
Nettersheim D. et al., BMP Inhibition in Seminomas Initiates
Acquisition of Pluripotency via Nodal Signaling Resulting in Repro-
gramming to an Embryonal Carcinoma, PLOS Genet. vol. 11(7):
1-26, (2015).
Nurieva R.I. et al., "Molecular mechnisms for T cell tolerance",
Immunol. Rev. vol. 241: 133-144, (2011).
Orciani M. et al., "CD38 is constitutively expressed in the nucleus
of human hematopoietic cells", J. Cell. Biochem., vol. 105(3):
905-912, (2008).
Pant et al., "Accumulation of effector memory CD8+ T cells in nasal
polyps", Am. J. Rhinol. Allergy, vol. 27(5): 117-126, (2013).
Paul, W. E., "Chapter 1: The immune system: an introduction,"
Fundamental Immunology, 4th Edition, Ed. Lippicott-Raven Pub-
lishers, Philadelphia, (1999).
PCT/US17/49163; PCT International Search Report, Nov. 2, 2017
(2 pgs).
Peng et al., "Stems Cells and Development", vol. 17: 761-774,
(2008).
Portha B. et al., "Activation of the GLP-1 receptor signalling
pathway: a relevant strategy to repair a deficient beta-cell mass",
Exptl Diabetes Res. Article 376509: 1-11, (2011).
Prendergast F.G. et al, "Chemical and physical properties of aequorin
and the green fluorescent protein isolated from Aequorea forskaleå".
Biochemistry, vol. 17(17): 3448-53, (1978).
Rabinovitch A. et al., "Roles of cytokines in the pathogenesis and
therapy of type 1 diabetes", Cell Biochem Biophys , vol. 48(2-3):
159-63, (2007).
Raker V. K. et al., "Tolerogenic Dendritic Cells for Regulatory T
Cell Induction in Man", Front Immunol vol. 6(569): 1-11, (2015).
Raskin P. et al. "Glucagon and diabetes" The Medical Clinics of
North America 62, 713 (1978).
Romito A. et al., "Pluripotent Stem Cells: Current Understanding
and Future Directions", Stem Cells Int., Article ID 9451492 (2016).
Rossi D. et al., "The biology of chemokines and their receptors",
Annu Rev Immunol,, vol. 18: 217-242, (2000).

(56)        References Cited

OTHER PUBLICATIONS

Round J.L. et al., "Coordination of tolerogenic immune responses by the commensal microbiota", J Autoimmun, vol. 34(3): 220-225, (2010).

Rudensky A.Y., "Regulatory T cells and Foxp3", Immunol. Rev., vol. 241: 260-268 (2011).

Saito, T. et al., "Myogenic Expression of Mesenchymal Stem Cells within Myotubes of mdx Mice in Vitro and in Vivo", Tissue Eng., vol. 1: 327-343, (1995).

Abdi R. et al., "Immunomodulation by mesenchymal stem cells, A potential therapeutic strategy for type I diabetes", Diabetes, vol. 57: 1759-1767, (2008).

Aguayo-Mazzucato C. et al., "Stem cell therapy for type I diabetes", Nat Rev Endocrinol., vol. 6: 139-148, (2010).

Aguirre G.A. et al., Insulin-like growth factor-1 deficiency and metabolic syndrome, J. Trans. Med., vol. 14(1): 1-23, (2016).

Alberts, B., et al, "The Adaptive Immune System" Chapter 24, Molecular Biology of the Cell, Garland Science, NY (2002).

Alexandraki K. et al., "Inflammatory process in type 2 diabetes: The role of cytokines", Annals of the New York Academy of Sciences, 1084: 89-117, (2006).

Allenbach et al., "Role of regulatory T cells in a new mouse model of experimental autoimmune myositis", Am J. Pathol., vol. 174(3): 989-998, (2014).

Alvarez S. et al., "GM-CSF and IL-3 activities in schistosomal liver granulomas are controlled by stroma-associated heparan sulfate proteoglycans", J Leukoc Biol., vol. 59 (3): 435-441, (1996).

Aschner, Y. et al., "Transforming Growth Factor-?: Master Regulator of the Respiratory System in Health and Disease", Am J Respir Cell Mol Biol., vol. 54, No. 5 (2016).

Assmus, B., et al., "Transplantation of Progenitor Cells and Regeneration Enhancement in Acute Myocardial Infarction (TOPCARE-AMI)", Circulation, 2002; 106:3009-3017.

Bach J.F., "Anti-CD3 antibodies for type 1 diabetes: beyond expectations", Lancet., vol. 378: 459-460, (2011).

Barnett D, et al., "Absolute CD4+ T-lymphocyte and CD34+ stem cell counts by single-platform flow cytometry: the way forward", Br. J Haematol. vol. 106: 1059-1062, (1999).

Battaglia, M. et al., "Rapamycin promotes expansion of functional CD4+CD25+Foxp3+ regulator T cells of both healthy subjects and type 1 diabetic patients", J. Immunol., vol. 177: 8338-8347, (2006).

Benkirane, N., et al., Exploration of Requirements for Peptidomimetic Immune Recognition—Antigenic and Immunogenic Properties of Reduced Peptide Bond Pseudopeptide Analogues of a Histone Hexapeptide*, J. Biol. Chem., vol. 271: 33218-33224, (1996).

Bour-Jourdan H. et al., "Intrinsic and extrinsic control of peripheral T-cell tolerance by costimulatory molecules of the CD28/?B7 family", Immunol. Rev., vol. 241: 180-205, (2011).

Bradley L.M. et al., "Islet-specific Th1, but not Th2, cells secrete multiple chemokines and promote rapid induction of autoimmune diabetes", J Immunol, vol. 162:2511-2520, (1999).

Bryant, et al, Nat. Rev. Mol. Cell Biol. "Regulated transport of the glucose transporter GLUT 4", vol. 3(4): 267-277, (2002).

Cabrera O. et al., "The unique cytoarchitecture of human pancreatic islets has implications for islet cell function", Proc. Natl Acad. Sci. U.S., vol. 103: 2334-2339, (2006).

Cambiaggi C. et al., "Constitutive expression of CD69 in interspecies T-cell hybrids and locus assignment to human chromosome 12", ,Immunogenetics, vol. 36(2): 117-120, (1992).

Castelli C., "Lymphocyte activation gene-3 (LAG-3, CD223) in plasmacytoid dendritic cells (pDCs): a molecular target for the restoration of active antitumor immunity", Oncoimmunology, vol. 3(11): 1-4, (2014).

Choi J. et al., "The pathogenesis of systemic lupus erythematosus—an update", Curr Opin Immunol, vol. 24(6): 651-657, (2012).

Clark, R.A., "Resident memory T cells in human health and disease", Sci. Transl. Med., 7, 269rv1, (2015).

Curotto De Lafaille et al., "Effective recruitment and retention of older adults in physical activity research: PALS study", Immunity, vol. 30(6): 626-635, (2009).

Dalgleish A. G. et al., "The CD4 (T4) antigen is an essential component of the receptor for the AIDS retrovirus", Nature, vol. 312: 763-768, (1984).

Davis L.A. et al., "Mesodermal fate decisions of a stem cell: the Wnt switch", Cell Mol Life Sci., vol. 65(17): 2658-2574, (2008).

Defronzo R.A., "Pathogenesis of type 2 diabetes mellitus" Med. Clin. N. Am., vol. 88: 787-835 (2004).

Delgado, E., et al., Modulation of Autoimmune T-Cell Memory by Stem Cell Educator Therapy: Phase 1/2 Clinical Trial; EBioMedicine, vol. 2 , Issue 12 , 2024-2036.

Desai-Mehta, A. et al., "Hyperexpression of CD40 ligand by B and T cells in human lupus and its role in pathogenic autoantibody production," J. Clin. Invest. vol. 97(9), 2063-2073 (1996).

Devaraj S. et al., "Low-density lipoprotein postsecretory modification, monocyte function, and circulating adhesion molecules in type 2 diabetic patients with and without macrovascular complications: the effect of alpha-tocopherol supplementation", Circulation, vol. 102: 191-196, (2000).

Dey A. et al., "Significance of prohormone convertase 2, PC2, mediated initial cleavage at the proglucagon interdomain site, Lys70-Arg71, to generate glucagon", Endocrinol., vol. 146: 713-727, (2005).

Dobert, N., et al; Transplantation of progenitor cells after reperfused acute myocardial infarction: evaluation of perfusion and myocardial viability with FDG-PET and thallium SPECT; Eur J Nucl Med Mol Imaging (2004) 31:1146-1151; DOI 10.1007/s00259-004-1490-4.

Drucker D.J. et al., "The incretin system: glucagon-like peptide-1 receptor agonists and dipeptidyl peptidase-4 inhibitors in type 2 diabetes", Lancet, vol. 368: 1696-1705, (2006).

Drucker D.J., "The biology of incretin hormones", Cell Metab. vol. 3: 153-165, (2006).

Dzierzak E. et al., "Of lineage and legacy: the development of mammalian hematopoietic stem cells", Nature Immunol., vol. 9(2): 129-136, (2008).

Ehrlich M., "Endocytosis and trafficking of BMP receptors: Regulatory mechanisms for fine-tuning the signaling response in different cellular contexts", Cytokine Growth Factor Reviews, vol. 27, 35-42 (2016).

Elhabazi A.., "Structure and function of the immune semaphorin CD100/SEMA4D", Crit Rev Immunol., vol. 23(1-2):65-81, (2003).

Farrar W.L. et al., "Hematopoietic growth-factor signal transduction and regulation of gene expression", Immunology series, vol. 49: 379-410, (1990).

Forster R. et al., "CCR7 and its ligands: balancing immunity and tolerance", Nat Rev Immunol, vol. 8: 362-371, (2008).

Forster R. et al., "CCR7 coordinates the primary immune response by establishing functional microenvironments in secondary lymphoid organs", Cell, vol. 99: 23-33, (1999).

G. Da Silva Xavier et al.,"Per-arnt-sim (PAS) domain-containing protein kinase is downregulated in human islets in type 2 diabetes and regulates glucagon secretion", Diabetologia, vol. 54: 819-827, (2011).

Gerich J.E., "Physiology of glucose homeostasis", Diabetes Obes. Metab. vol. 2: 345-350, (2000).

Gotsman I. et al., "Impaired regulatory T-cell response and enhanced atherosclerosis in the absence of inducible costimulatory molecule", Circulation, vol. 114: 2047-2055, (2006).

Griffith J. W., "Chemokines and chemokine receptors: positioning cells for host defense and immunity", Annual Review of Immunology, vol. 32: 659-702, (2014).

Grifoni D. et al., "*Drosophila* Myc: A master regulator of cellular performance", Biochim Biophys Acta, vol. 1849(5): 570-581 (2015).

Habener J. F. et al., "Alpha cells some of age", Trends in Endocrinology & Metabolism: TEM vol. 24, 153-163 (2013).

Hamano K. et al., "Local implantation of autologous bone marrow cells for therapeutic angiogenesis in patients with ischemic heart disease: clinical trial and preliminary result", Japan Cir. J., vol. 65: 845-847, (2001).

Herman, A. E., et al, CD4+ CD25+ T regulatory cells dependent on ICOS promote regulation of effector cells in the prediabeti clesion, J. Expt Med. vol. 199: 1479-1489, (2004).

Hodgkinson T. et al., "Adult stem cells in tissue engineering", Expert Rev Med Devices , vol. 6(6): 621-640 (2009).

(56) References Cited

OTHER PUBLICATIONS

Hopken U. E. et al., "The chemokine receptor CCR7 controls lymph node-dependent cytotoxic T cell priming in alloimmune responses", Eur J Immunol., vol. 34:461-470, (2004).

Hori S., "Effective proliferation of human regulatory T cells requires a strong costimulatory CD28 signal that cannot be substituted by IL-2", Eur. J. Immunol., vol. 40: 664-667, (2010).

Hornbach A. A. et al., "Effective proliferation of human regulatory T cells requires a strong costimulatory CD28 signal that cannot be substituted by IL-2", J. Immunol., vol. 179: 7924-7931, (2007).

Schrum S. et al., "Synthesis of the CC-chemokines MIP-1alpha, MIP-1beta, and Rantes is associated with a type 1 immune response", J Immunol, vol. 157: 3598-3604, (1996).

Schwartz, R. H., "T cell anergy", Annu. Rev. Immunol., vol. 21: 305-334 (2003).

Shoelson S.E. et al., "Inflammation and insulin resistance", J Clin Invest, vol. 116: 1793-1801, (2006).

Simmons D. L. et al.,"Molecular cloning of a cDNA encoding CD34, a sialomucin of human hematopoietic stem cells", J. Immunol,, vol. 148(1): 267-271, (1992).

Sprent J. et al., "The thymus and central tolerance", Philos Trans R Soc Lond B Biol Sci, vol. 356(1409): 609-616, (2001).

Strauer B. E., et al., "Repair of infarcted myocardium by autologous intracoronary mononuclear bone marrow cell transplantation in humans", Circulation, vol. 106: 1913-1918, (2002).

Sumarac-Dumanovic M. et al.,"Increased activity of interleukin-23/interleukin-17 proinflammatory axis in obese women", Int J Obes (Lond), vol. 33: 151-156, (2009).

Sutherland, et al., "The Ishage guidelines for CD34+ cell determination by flow cytometry. International Society of Hematotherapy and Graft Engineering", J Hematotherapy. vol. 5: 213-226, (1996).

Taams, L. S. et al., "Human anergic/suppressive CD4+CD25+ T cells: a highly differentiated and apoptosis-prone population", Eur. J. Immunol. vol. 31: 1122-1131(2001).

Tang Q. et al., "CTLA4 Expression Is an Indicator and Regulator of Steady-State CD4+FoxP3+ T Cell Homeostasis", J. Immunol., vol. 171: 3348-3352, (2003).

Taub D.D. et al., "Recombinant human interferon-inducible protein 10 is a chemoattractant for human monocytes and T lymphocytes and promotes T cell adhesion to endothelial cells", J Exp Med., vol. 177:1809-1814, (1993).

Tedder T. F. et al., "Isolation and structure of a cDNA encoding the B1 (CD20) cell-surface antigen of human B lymphocytes", Proc Natl Acad Sci USA, vol. 85(1): 208-212, (1998).

Thomson J. A. et al., "Embryonic stem cell lines derived from human blastocysts", Science, vol. 282: 1145-1147, (1992).

Tomita S. et al., "Autologous transplantation of bone marrow cells improves damaged heart function", Circulation, vol. 100 (Suppl. II): 247-256, (1999).

Triplett, T. A., et al, Defining a functionally distinct subset of human memory CD4+ T cells that are CD25POS and FOXP3NEG, Eur. J. Immunol. 2012. 42: 1893-1905.

Triplitt C.L., "Examining the mechanisms of glucose regulation", Am. J. Manag. Care, vol. 18 (1 Suppl) S4-S10, (2012).

Uccelli A. et al., "Mesenchymal stem cells in health and disease", Nat Rev Immunol., vol. 8: 726-736, (2008).

Uldry M. et al., "The SLC2 family of facilitated hexose and polyol transporters", Thorens B, Eur. J. Physiol. 2004; vol. 447: 480-489, (2004).

Unger R.H. et al., "Glucagonocentric restructuring of diabetes: a pathophysiologic and therapeutic makeover", J. Clinical Investig. vol. 122(1): 4-12, (2012).

Unger R.H. et al., "Paracrinology of islets and the paracrinopathy of diabetes", Proc. Natl Acad. Sci., U.S., vol. 107 (37): 16009-16012, (2010).

Vang K.B., et al., "Cutting edge: CD28 and c-Rel-dependent pathways initiate regulatory T cell development" , J. Immunol., vol. 184: 4074-77, (2010).

Vuguin P.M. et al. "Novel insight into glucagon receptor action: lessons from knockout and transgenic mouse models", Diabetes, Obesity & Metabolism, vol. 13(1), 144-150, (2011).

Wahren J. et al., "The clinical potential of C-peptide in replacement in type 1 diabetes", Diabetes, vol. 61(4), 761-772, (2012).

Wang J. S. et al., "The coronary delivery of marrow stromal cells for myocardial regeneration: pathophysiologic and therapeutic implications", J. Thorac. Cardiovasc. Surg., vol. 122: 699-705, (2001).

Wetzel A. et al., "Human Thy-1 (CD90) on activated endothelial cells is a counterreceptor for the leukocyte integrin Mac-1 (CD11b/CD18)", J. Immunol., 172: 3850-3857, (2004).

Wherrett D.K. et al., "Antigen-based therapy with glutamic acid decarboxylase (GAD) vaccine in patients with recent-onset type 1 diabetes: a randomized double-blind trial", Lancet., vol. 378: 319-327, (2011).

Wollert K. C. et al., "Intracoronary autologous bone-marrow cell transfer after myocardial infarction: the Boost randomized controlled clinical trial", Lancet, vol. 364: 141-148, (2004).

Wu H.P. et al., "High interleukin-12 production from stimulated peripheral blood mononuclear cells of type 2 diabetes patients", Cytokine, vol. 51: 298-304, (2010).

Xu W. et al., "Progress in the development of aminopeptidase N (APN/CD13) inhibitors", Curr Med Chem Anticancer Agents., vol. 5(3): 281-301, (2005).

Youn B. et al., "Chemokines, chemokine receptors and hematopoiesis", Immunol Rev, vol. 177: 150-174, (2000).

Zhang X. et al., "Successful immortalization of mesenchymal progenitor cells derived from human placenta and the differentiation abilities of immortalized cells", Biochem Biophys Res Commun, vol. 351: 853-859, (2006).

Zhao Y. et al., "Human cord blood stem cell-modulated regulatory T lymphocytes reverse the autoimmune-caused type 1 diabetes in nonobese diabetic (NOD) mice", Plos One, vol. 4: e4226, (2009).

Zhao Y. et al., "Human cord blood stem cells and the journey to a cure for type 1 diabetes", Autoimmun Rev., vol. 10: 103-107, (2010).

Zhao Y. et al., "Reversal of type 1 diabetes via islet ?-cell regeneration following immune modulation by cord blood-derived multipotent stem cells", BMC Med. vol. 10(3), 1-11, (2012).

Zhao Y. et al., "Targeting insulin resistance in type 2 diabetes via immune modulation of cord blood-derived multipotent stem cells (CB-SCs) in stem cell educator therapy: phase I/II clinical trial", BMC Med., vol. 11: 160, (2013).

Zhao Y. et al.," Immune regulation of T lymphocyte by a newly characterized human umbilical cord blood stem cell", Immunol Lett., vol. 108: 78-87, (2007).

Zhao Y., "Stem cell educator therapy and induction of immune balance", Curr Diab Rep., vol. 12: 517-523, (2012).

Zhao, Y., et al; "Identification of stem cells from human umbilical cord blood with embryonic and hematopoietic characteristics", Exp. Cell Res., vol. 312: 2454-2464 (2006).

Zuccarino-Catania G. V. et al., "CD80 and PD-L2 define functionally distinct memory B cell subsets that are independent of antibody isotype", Nat Immunol., vol. 15(7):631-637, (2012).

Li, Y. et al., Hair regrowth in alopecia areata patients following Stem Cell Educator therapy. BMC Medicine, 13:87, Apr. 20, 2015.

Wang, Z-X, et al., Clinical efficacy of autologous stem cell transplantation for the treatment of patients with type 2 diabetes mellitus: a meta-analysis. Cytotherapy, 2015; 17:956-968.

Guidance to Accompany the Fact-Jacie International Standards for Cellular Therapy Product Collection, Processing, and Administration. Draft Fifth Edition. 2011.

McCall, A. L. et al., Treating type 1 diabetes: from strateges for insulin delivery to dual hormonal control, Minerva Endocrinol, Jun. 2013; 38(2): 145-163.

CN Publication No. 109844093, China International Search Report, Mar. 3, 2022 (translation), (4 pages).

KR Publication No. 10-2019-0042079, Korean International Office Action, dated Feb. 4, 2022 (translation), (6 pages).

Ospina, S. B. et al, Is the endocrine research pipeline broken? A systematic evaluation of the Endocrine Society clinical practice guidelines and trial registration, BMC Medicine (2015) 13:187.

(56)         References Cited

OTHER PUBLICATIONS

Yamada, Y. et al, A novel approach for myocardial regeneration with educated cord blood celle cocultured with cells from brown adipose tissue, BRRC, vol. 353 (2007) 182-188.

JP Published Application No. 2019-512007, Office Action dated May 2, 2022 and translation.

CN Publication No. 109844093, Decision on Rejection dated Sep. 6, 2023 [English translation included].

Aoki, Mika, et al., Derivation of Functional Endothelial Progenitor Cells from Human Umbilical Cord Blood Mononuclear Cells Isolated by a Novel Cell Filtration Device, Stem Cells, vol. 22, Issue 6, Nov. 2004, pp. 994-1002.

Duan Huacin, "Isolation and culture of two types of endothelial progenitor cells derived from human cord blood", The 11th China Conference on Experimental Hematology, 2016 [English translation included].

Zhao, Meng-die, et al., Study on the separation, culturation and identification of human umbilical cord blood progenitor cells., J Bengbu Med Coll, Sep. 2016, vol. 41, No. 9 [English translation of Abstract].

Gattinoni, Luca, et al.; Paths to stemness:building the ultimate antitumour T cell; Nature Reviews | Cancer; 2012, vol. 12, pp. 671-684.

\* cited by examiner

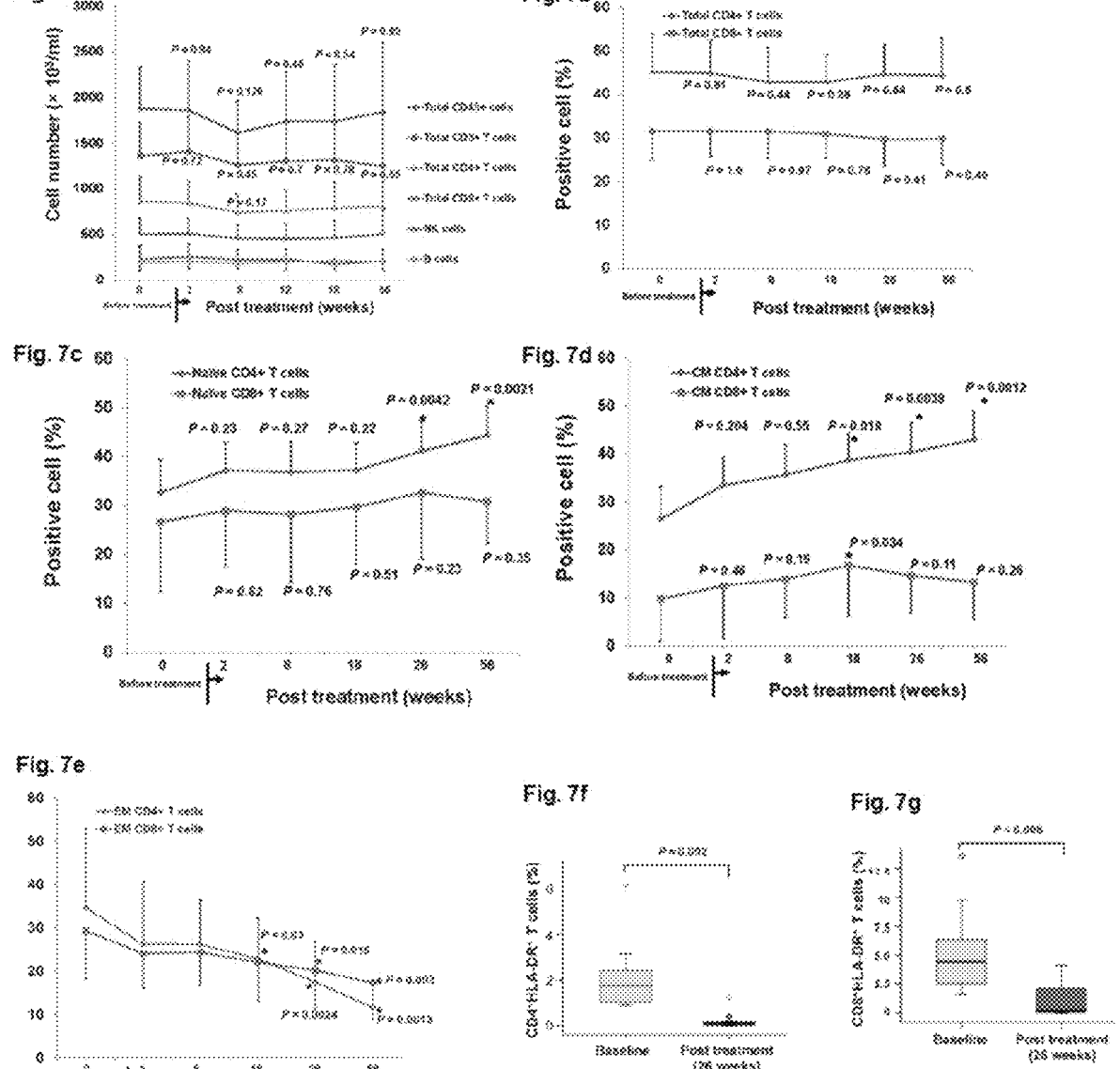

Fig. 9a
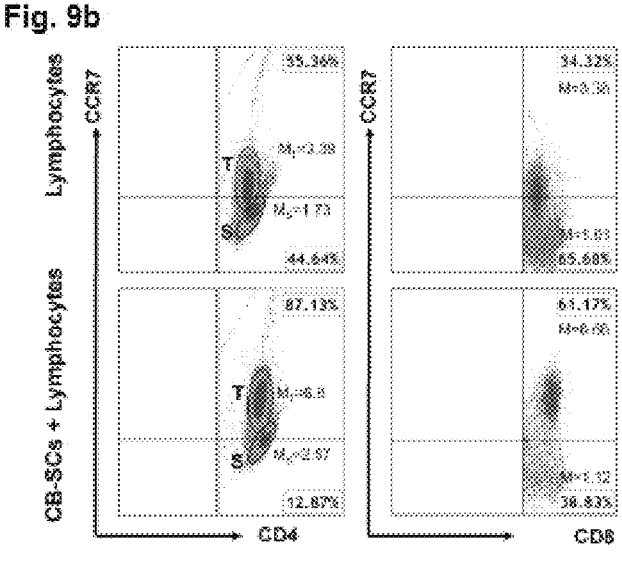
Fig. 9b
Fig. 9c
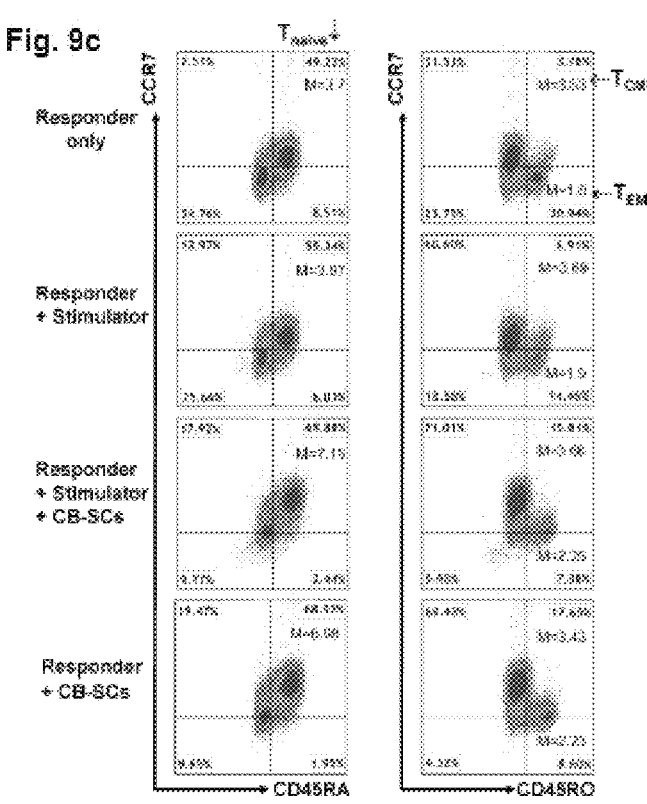

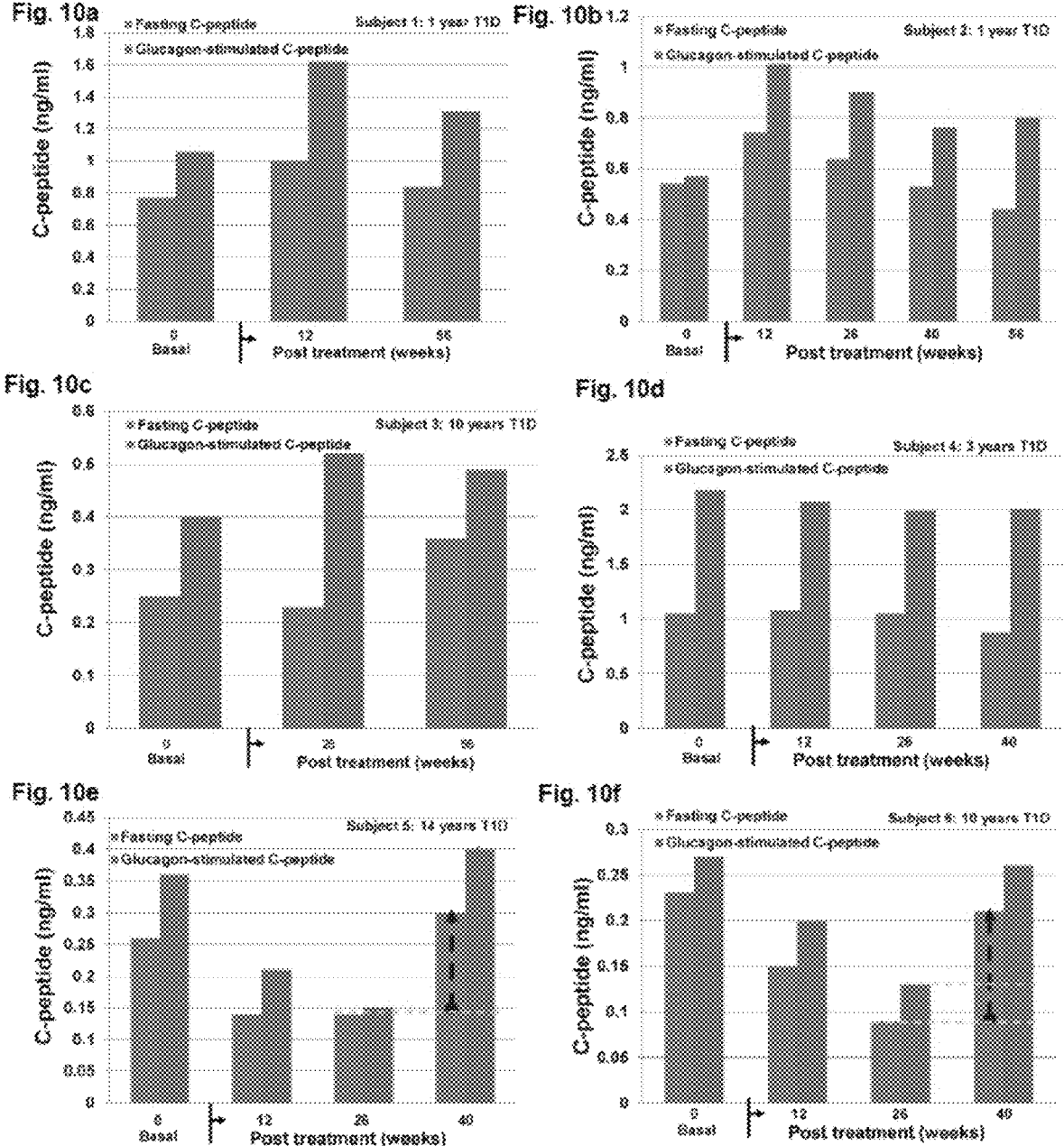

Fig. 12a                    Fig. 12b
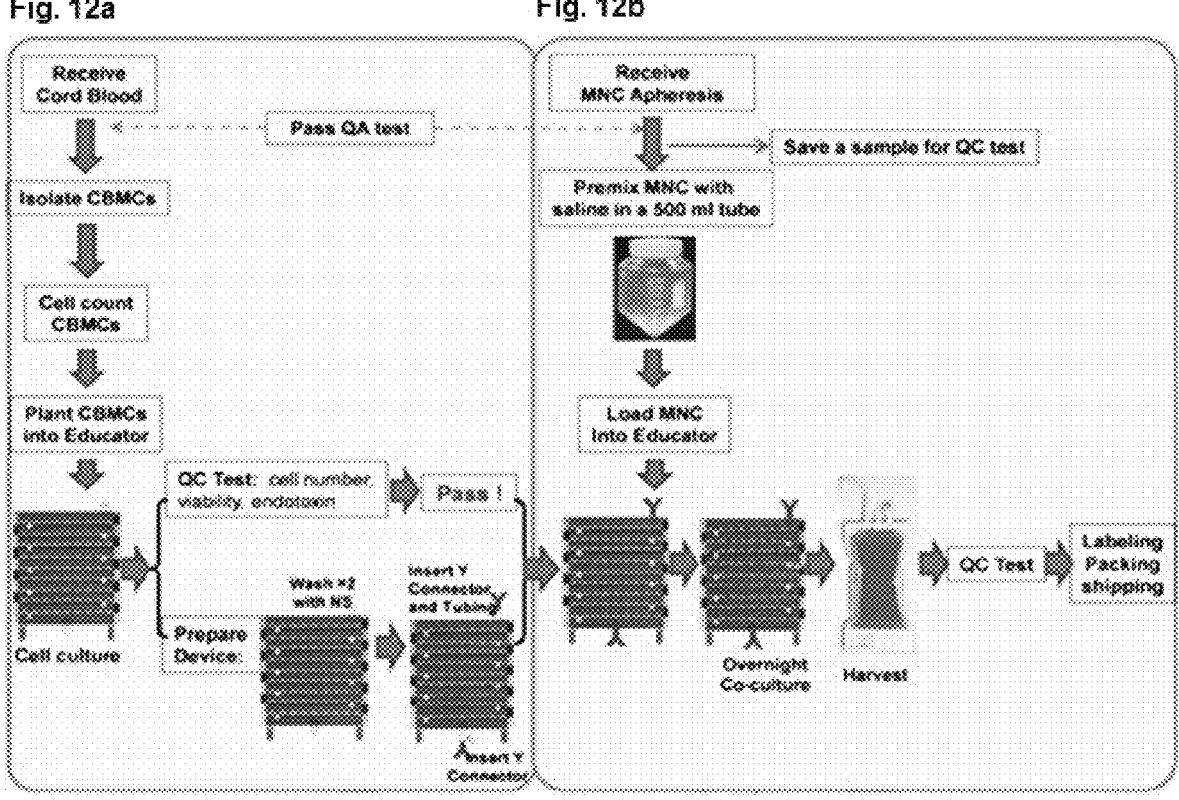

Diagram flow chart 1 of the phase 1/2 clinical trial.

METHODS FOR TREATING AN IMMUNE DISORDER-RELATED DISEASE BY REDUCING AUTOREACTIVITY IN A T CELL COMPARTMENT

CROSS-REFERENCE TO RELATED APPLICATIONS

This application claims the benefit of priority to U.S. Provisional Application No. 62/380,904 filed on Aug. 29, 2016, the entire contents of which are incorporated by reference herein.

FIELD OF THE INVENTION

The described invention relates to an apparatus, pharmaceutical compositions and methods for treating patients with autoreactivity in a T cell compartment.

BACKGROUND OF THE INVENTION

Characteristics of an Immune Response

Generally speaking, immune responses are initiated by an encounter between an individual and a foreign antigenic substance, e.g., an infectious microorganism. The infected individual rapidly responds with the production of antibody molecules specific for the antigenic determinants/epitopes of the immunogen and with the expansion and differentiation of antigen-specific regulatory and effector T-lymphocytes, including both cells that produce cytokines and killer T cells, capable of lysing infected cells. Primary immunization with a given microorganism evokes antibodies and T cells that are specific for the antigenic determinants/epitopes found on that microorganism but that usually fail to recognize or recognize only poorly antigenic determinants expressed by unrelated microbes [Paul, W. E., "Chapter 1: The immune system: an introduction," Fundamental Immunology, 4th Edition, d. Paul, W. E., Lippicott-Raven Publishers, Philadelphia, (1999), at p. 102].

As a consequence of this initial response, the immunized individual develops a state of immunologic memory. If the same or a closely related microorganism is encountered again, a secondary response ensues. This secondary response generally consists of an antibody response that is more rapid, greater in magnitude and composed of antibodies that bind to the antigen with greater affinity and are more effective in clearing the microbe from the body, and a similarly enhanced and often more effective T-cell response. However, immune responses against infectious agents do not always lead to elimination of the pathogen. Id.

While the immune response is highly specific in its reactivity, the range of antigenic specificities that can be discriminated by the immune system is enormous.

Cells of the Immune System

Cells of the immune system include lymphocytes, monocytes/macrophages, dendritic cells, the closely related Langerhans cells, natural killer (NK) cells, mast cells, basophils, and other members of the myeloid lineage of cells. In addition, a series of specialized epithelial and stromal cells provide the anatomic environment in which immunity occurs, often by secreting critical factors that regulate growth and/or gene activation in cells of the immune system, which also play direct roles in the induction and effector phases of the response. Id.

The cells of the immune system are found in peripheral organized tissues, such as the spleen, lymph nodes, Peyer's patches of the intestine and tonsils. Lymphocytes also are found in the central lymphoid organs, the thymus, and bone marrow where they undergo developmental steps that equip the to mediate the myriad responses of the mature immune system. A substantial portion of the lymphocytes and macrophages comprise a recirculating pool of cells found in the blood and lymph, providing the means to deliver immunocompetent cells to sites where they are needed and to allow immunity that is generated locally to become generalized. Id.

The term "lymphocyte" refers to a small white blood cel formed in lymphatic tissue throughout the body and in normal adults making up about 22-28% of the total number of leukocytes in the circulating blood that plays a large role in defending the body against disease. Individual lymphocytes are specialized in t at they are committed to respond to a limited set of structurally related antigens. This commitment, which exists before the first contact of the immune system with a given antigen, is expressed by the presence of receptors specific for determinants (epitopes) on the antigen on the lymphocyte's surface membrane. Each lymphocyte possesses a population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions. Id.

Two broad classes of lymphocytes are recognized: the B-lymphocytes (B-cells), which are precursors of antibody-secreting cells, and T-lymphocytes (T-cells), B-Lymphocytes B-lymphocytes are derived from hematopoietic cells of the bone marrow. A mature B-cell can be activated with an antigen that expresses epitopes that are recognized by its cell surface. The activation process may be direct, dependent on cross-linkage of membrane Ig molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses [Paul, W. E., "Chapter 1: The immune system: an introduction," Fundamental Immunology, 4th Edition, Ed. Paul, W. E., Lippicott-Raven Publishers, Philadelphia, (1999)].

Cross-linkage dependent B-cell activation requires that the antigen express multiple copies of the epitope complementary to the binding site of the cell surface receptors because each B-cell expresses Ig molecules with identical variable regions. Such a requirement is fulfilled by other antigens with repetitive epitopes, such as capsular polysaccharides of microorganisms or viral envelope proteins. Cross-linkage-dependent B-cell activation is a major protective immune response mounted against these microbes [Paul, W. E., "Chapter 1: The immune system: an introduction", Fundamental Immunology, 4th Edition, Ed. Paul, W. E., Lippicott-Raven Publishers, Philadelphia, (1999)].

Cognate help allows B-cells to mount responses against antigens that cannot cross-link receptors and, at the same time, provides costimulatory signals that rescue B cells from inactivation when they are stimulated by weak cross-linkage events. Cognate help is dependent on the binding of antigen by the B-cell's membrane immunoglobulin (Ig), the endocytosis of the antigen, and its fragmentation into peptides within the endosomal/lysosomal compartment of the cell. Some of the resultant peptides are loaded into a groove in a specialized set of cell surface proteins known as class II major histocompatibility complex (MHC) molecules. The resultant class II/peptide complexes are expressed on the cell surface and act as ligands for the antigen-specific receptors of a set of T-cells designated as CD4⁺ T-cells. The CD4⁺ T-cells bear receptors on their surface specific for the B-cell's class II/peptide complex. B-cell activation depends not only on the binding of the T cell through its T cell receptor (TCR), but this interaction also allows an activation ligand on the T-cell (CD40 ligand) to bind to its receptor on the B-cell (CD40) signaling B-cell activation. In addition, T helper cells secrete several cytokines that regulate the growth and differentiation of the stimulated B-cell by binding to cytokine receptors on the B cell [Paul, W. E., "Chapter 1: The immune system: an introduction, "Fundamental Immunology, 4th Edition, Ed. Paul, W. E., Lippicott-Raven Publishers, Philadelphia, (1999)].

During cognate help for antibody production, the CD40 ligand is transiently expressed on activated CD4⁺ T helper cells, and it binds to CD40 on the antigen-specific B cells, thereby transducing a second costimulatory sign 1. The latter signal is essential for B cell growth and differentiation and for the generation of memory B cells by preventing apoptosis of germinal center B cells that have encountered antigen. Hyperexpression of the CD40 ligand in both B and T cells is implicated in the pathogenic autoantibody production in human SLE patients [Desai-Mehta, A. et al., "Hyperexpression of CD40 ligand by B and T cells in human lupus and its role in pathogenic autoantibody production," J. Clin. Invest. Vol. 97(9), 2063-2073, (1996)].

T-Lymphocytes

T-lymphocytes derive from precursors in hematopoietic tissue, undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on their expression of specific cell surface molecules and the secretion of cytokines [Paul, W. E., "Chapter 1: The immune system: an introduction", Fundamental Immunology, 4th Edition, Ed. Paul, W. E., Lippicott-Raven Publishers, Philadelphia, (1999)].

T cells differ from B cells in their mechanism of antigen recognition. Immunoglobulin, the B cell's receptor, binds to individual epitopes on soluble molecules or on particulate surfaces. B-cell receptors see epitopes expressed on the surface of native molecules. While antibody and B-cell receptors evolved to bind to and to protect against microorganisms in extracellular fluids, T cells recognize antigens on the surface of other cells and mediate their functions by interacting with, and altering, the behavior of these antigen-presenting cells (APCs). There are three main types of antigen-presenting cells in peripheral lymphoid organs that can activate T cells: dendritic cells, macrophages and B cells. The most potent of these are the dendritic cells, whose only function is to present foreign antigens to T cells. Immature dendritic cells are located in tissues throughout the body, including the skin, gut, and respiratory tract. When they encounter invading microbes at these sites, they endocytose the pathogens and their products, and carry them via the lymph to local lymph nodes or gut associated lymphoid organs. The encounter with a pathogen induces the dendritic cell to mature from an antigen-capturing cell to an antigen-presenting cell (APC) that can activate T cells. APCs display three types of protein molecules on their surface that have a role in activating a T cell to become an effector cell: (1) MHC proteins, which present foreign antigen to the T cell receptor; (2) costimulatory proteins which bind to complementary receptors on the T cell surface; and (3) cell-cell adhesion molecules, which enable a T cell to bind to the antigen-presenting cell (APC) for long enough to become activated ["Chapter 24: The adaptive immune system," Molecular Biology of the Cell, Alberts, B. et al., Garland Science, NY, (2002)].

T-cells are subdivided into two distinct classes based on the cell surface receptors they express. The majority of T cells express T cell receptors (TCR) consisting of α and β-chains. A small group of T cells express receptors made of γ and δ chains. Among the α/β T cells are two sub-lineages: those that express the coreceptor molecule CD4 (CD4⁺ T cells); and those that express CD8 (CD8⁺ T cells). These cells differ in how they recognize antigen and in their effector and regulatory functions.

CD4+ T cells are the major regulatory cells of the immune system. Their regulatory function depends both on the expression of their cell-surface molecules, such as CD40 ligand whose expression is induced when the T cells are activated, and the wide array of cytokines they secrete when activated.

T cells also mediate important effector functions, some of which are determined by the patterns of cytokines they secrete. The cytokines can be directly toxic to target cells and can mobilize potent inflammatory mechanisms.

In addition, T cells, particularly CD8⁺ T cells, can develop into cytotoxic T-lymphocytes (CTLs) capable of efficiently lysing target cells that express antigens recognized by the CTLs [Paul, W. E., "Chapter 1: The immune system: an introduction," Fundamental Immunology, 4th Edition, Ed. Paul, W. E., Lippicott-Raven Publishers, Philadelphia, (1999)].

T cell receptors (TCRs) recognize a complex consisting of a peptide derived by proteolysis of the antigen bound to a specialized groove of a class II or class I MHC protein. CD4+ T cells recognize only peptide/class II complexes while CD8⁺ T cells recognize peptide/class I complexes [Paul, W. E., "Chapter 1: The immune system: an introduction," Fundamental Immunology, 4th Edition, Ed. Paul, W. E., Lippicott-Raven Publishers, Philadelphia, (1999)].

The TCR's ligand (i.e., the peptide/MHC protein complex) is created within antigen-presenting cells (APCs). In general, class II MHC molecules bind peptides derived from proteins that have been taken up by the APC through an endocytic process. These peptide-loaded class II molecules are then expressed on the surface of the cell, where they are available to be bound by CD4⁺ T cells with TCRs capable of recognizing the expressed cell surface complex. Thus, CD4⁺ T cells are specialized to react with antigens derived from extracellular sources [Paul, W. E., "Chapter 1: The immune system: an introduction," Fundamental Immunology, 4th Edition, Ed. Paul, W. E., Lippicott-Raven Publishers, Philadelphia, (1999)].

In contrast, class I MHC molecules are mainly loaded with peptides derived from internally synthesized proteins, such as viral proteins. These peptides are produced from cytosolic proteins by proteolysis by the proteosome and are translocated into the rough endoplasmic reticulum. Such peptides, generally composed of nine amino acids in length, are bound into the class I MHC molecules and are brought to the cell surface, where they can be recognized by CD8+ T cells expressing appropriate receptors. This gives the T cell system, particularly CD8⁺ T cells, the ability to detect cells expressing proteins that are different from, or produced in much larger amounts than, those of cells of the remainder of the organism (e.g., viral antigens) or mutant antigens (such as active oncogene products), even if these proteins in their intact form are neither expressed on the cell surface nor secreted [Paul, W. E., "Chapter 1: The immune system: an introduction," Fundamental Immunology, 4th Edition, Ed. Paul, W. E., Lippicott-Raven Publishers, Philadelphia, (1999)].

T cells can also be classified based on their function as helper T cells; T cells involved in inducing cellular immunity; suppressor T cells; and cytotoxic T cells.

Helper T Cells

Helper T cells are T cells that stimulate B cells to make antibody responses to proteins and other T cell-dependent antigens. T cell-dependent antigens are immunogens in which individual epitopes appear only once or a limited number of times such that they are unable to cross-link the membrane immunoglobulin (Ig) of B cells or do so inefficiently. B cells bind the antigen through their membrane Ig, and the complex undergoes endocytosis. Within the endosomal and lysosomal compartments, the antigen is fragmented into peptides by proteolytic enzymes and one or more of the generated peptides are loaded into class II MHC molecules, which traffic through this vesicular compartment. The resulting peptide/class II MHC complex is then exported to the B-cell surface membrane. T cells with receptors specific for the peptide/class II molecular complex recognize this complex on the B-cell surface. [Paul, W. E., "Chapter 1: The immune system: an introduction," Fundamental Immunology, 4th Edition, Ed. Paul, W. E., Lippicott-Raven Publishers, Philadelphia (1999)].

B-cell activation depends both on the binding of the T cell through its TCR and on the interaction of the T-cell CD40 ligand (CD40L) with CD40 on the B cell. T cells do not constitutively express CD40L. Rather, CD40L expression is induced as a result of an interaction with an APC that expresses both a cognate antigen recognized by the TCR of the T cell and CD80 or CD86. CD80/CD86 is gen rally expressed by activated, but not resting, B cells so that the helper interaction involving an activated B cell and a T cell can lead to efficient antibody production. In many cases, however, the initial induction of CD40L on T cells is dependent on their recognition of antigen on the surface of APCs that constitutively express CD80/86, such as dendritic cells. Such activated helper T cells can then efficiently interact with and help B cells. Cross-linkage of membrane Ig on the B cell, even if inefficient, may synergize with the CD40L/CD40 interaction to yield vigorous B-cell activation. The subsequent events in the B-cell response, including proliferation, Ig secretion, and class switching (of the Ig class being expressed) either depend or are enhanced by the actions of T cell-derived cytokines [Paul, W. E., "Chapter 1: The immune system: an introduction," Fundamental Immunology, 4th Edition, Ed. Paul, W. E., Lippicott-Raven Publishers, Philadelphia, (1999)].

CD4+ T cells tend to differentiate into cells that principally secrete the cytokines IL-4, IL-5, IL-6, and IL-10 (TH2 cells) or into cells that mainly produce IL-2, IFN-γ, and lymphotoxin (TH1 cells). The TH2 cells are very effective in helping B-cells develop into antibody-producing cells, whereas the TH1 cells are effective inducers of cellular immune responses, involving enhancement of microbicidal activity of monocytes and macrophages, and consequent increased efficiency in lysing microorganisms in intracellular vesicular compartments. Although CD4+ T cells with the phenotype of TH2 cells (i.e., IL-4, IL-5, IL-6 and IL-10) are efficient helper cells, TH1 cells also have the capacity to be helpers [Paul, W. E., "Chapter 1: The immune system: an introduction, "Fundamental Immunology, 4th Edition, Ed. Paul, W. E., Lippicott-Raven Publishers, Philadelphia, (1999)].

T Cells Involved in Induction of Cellular Immunity

T cells also may act to enhance the capacity of monocytes and macrophages to destroy intracellular microorganisms. In particular, interferon-gamma (IFN-γ) produced by helper T cells enhances several mechanisms through which mononuclear phagocytes destroy intracellular bacteria and parasitism including the generation of nitric oxide and induction of tumor necrosis factor (TNF) production. TH1 cells are effective in enhancing the microbicidal action, because they produce IFN-γ. In contrast, two of the major cytokines produced by TH2 cells, IL-4 and IL-10, block these activities [Paul, W. E., "Chapter 1: The immune system: an introduction," Fundamental Immunology, 4th Edition, Ed. Paul, W. E., Lippicott-Raven Publishers, Philadelphia, (1999)].

Suppressor or Regulatory T (Treg) Cells

Immune homeostasis is maintained by a controlled balance between initiation and downregulation of the immune response. The mechanisms of both apoptosis and T cell anergy (a tolerance mechanism in which the T cells are intrinsically functionally inactivated following an antigen encounter [Scwartz, R. H., "T cell anergy", Annu. Rev. Immunol., Vol. 21: 305-334 (2003)] contribute to the downregulation of the immune response. A third mechanism is provided by active suppression of activated T cells by suppressor or regulatory CD4+ T (Treg) cells [Reviewed in Kronenberg, M. et al., "Regulation of immunity by self-reactive T cells", Nature, Vol. 435: 598-604 (2005)]. CD4+ Tregs that constitutively express the IL-2 receptor alpha (IL-2Rα) chain (CD4+CD25+) are a naturally occurring T cell subset that are anergic and suppressive [Taams, L. S. et al., "Human anergic/suppressive CD4+CD25+ T cells: a highly differentiated and apoptosis-prone population", Eur. J. Immunol. Vol. 31: 1122-1131 (2001)]. Depletion of CD4+ CD25+ Tregs results in systemic autoimmune disease in mice. Furthermore, transfer of these Tregs prevents development of autoimmune disease. Human CD4+ CD25+ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human CD4+CD25+ T cells can be split into suppressive (CD25^high) and nonsuppressive (CD25^low) cells, according to the level of CD25 expression. A member of the forkhead family of transcription factors, FOXP3, has been shown to be expressed in murine and human CD4+CD25+ Tregs and appears to be a master gene controlling CD4+CD25+ Treg development [Battaglia, M. et al., "Rapamycin promotes expansion of functional CD4+ CD25+ Foxp3+ regulator T cells of both healthy subjects and type 1 diabetic patients", J. Immunol., Vol. 177: 8338-8347, (2006)].

Cytotoxic T Lymphocytes (CTL)

CD8+ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by granzymes, a series of enzymes produced by activated CTLs. Many active CTLs also express large amounts of fas ligand on their surface. The interaction of fas ligand on the surface of CTL with fas on the surface of the target cell initiates apoptosis in the target cell, leading to the death of these cells. CTL-mediated lysis appears to be a major mechanism for the destruction of virally infected cells.

Priming

The term "unprimed cells" (also referred to as virgin, naïve, or inexperienced cells) as used herein refers to T cells and B cells that have generated an antigen receptor (TCR for T cells, BCR for B cells) of a particular specificity, but have never encountered the antigen. The term "priming" as used herein refers to the process whereby T cells and B cell precursors encounter the antigen for which they are specific.

For example, before helper T cells and B cells can interact to produce specific antibody, the antigen-specific T cell precursors must be primed. Priming involves several steps: antigen uptake, processing, and cell surface expression bound to class II MHC molecules by an antigen presenting cell, recirculation and antigen-specific trapping of helper T cell precursors in lymphoid tissue, and T cell proliferation and differentiation [Janeway, CA, Jr., "The priming of helper T cells", Semin. Immunol., Vol. 1(1): 13-20 (1989)]. Helper T cells express CD4, but not all CD4 T cells are helper cells. Id. The signals required for clonal expansion of helper T cells differ from those required by other CD4 T cells. The critical antigen-presenting cell for helper T cell priming appears to be a macrophage; and the critical second signal for helper T cell growth is the macrophage product interleukin 1 (IL-1). Id. If the primed T cells and/or B cells receive a second, co-stimulatory signal, they become activated T cells or B cells.

Lymphocyte Activation

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immunoglobulin Ig. The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase C$\gamma$1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the antigen presenting cell (APC). The soluble product of an activated B lymphocyte is immunoglobulins (antibodies). The soluble product of an activated T lymphocyte is lymphokines.

Chemokines are chemotactic cytokines, which constitute a family of low molecular mass (8-11 kDa) structurally-related proteins with diverse immune and neural functions [Mackay C. R., "Chemokines: immunology's high impact factors", Nat Immunol., Vol. 2: 95-101, (2001)]; [Youn B. et al., "Chemokines, chemokine receptors and hematopoiesis", Immunol Rev, Vol. 177: 150-174, (2000)] that can be categorized into four subfamilies (C, CC, CXC and CX3C) based on the relative positions of conserved cysteine residues [Rossi D. et al., "The biology of chemokines and their receptors", Annu Rev Immunol, Vol. 18: 217-242, (2000)]. Chemokines are essential molecules in directing leucocyte migration between blood, lymph nodes and tissues. They constitute a complex signaling network because they are not always restricted to one type of receptor [Loetscher P. et al., "The ligands of CXC chemokine receptor 3, I-TAC, Mig, and IP10, are natural antagonists for CCR3", J. Biol. Chem., Vol. 276: 2986-2991, (2001)]. Chemokines affect cells by activating surface receptors that are seven-transmembrane-domain G-protein-coupled receptors. Leukocyte responses to particular chemokines are determined by their expression of chemokine receptors. The binding of the chemokine to the receptor activates various signaling cascades, similar to the action of cytokines that culminate in the activation of a biological response. Secretion of the ligands for the CCR5 receptor, regulated upon activation normal T cell expressed and secreted (RANTES), macrophage inflammatory protein (MIP)-1$\alpha$/and MIP-1$\beta$ [Schrum S. et al., "Synthesis of the CC-chemokines MIP-1alpha, MIP-1beta, and RANTES is associated with a type 1 immune response", J Immunol, Vol. 157: 3598-3604, (1996)] and the ligand for CXC chemokine receptor 3 (CXCR3), induced protein (IP)-10 [Taub D. D. et al., "Recombinant human interferon inducible protein 10 is a chemoattractant for human monocytes and T lymphocytes and promotes T cell adhesion to endothelial cells", J Exp Med., Vol. 177:1809-1814, (1993)] have been associated with unwanted heightened T$_{H1}$ responses. Additionally, elevated damaging pro-inflammatory cytokine levels of IL-2 and IFN-$\gamma$ correlate with T1D [Rabinovitch A. et al., "Roles of cytokines in the pathogenesis and therapy of type 1 diabetes", Cell Biochem Biophys, Vol. 48(2-3): 159-63, (2007)]. Chemokines have been observed in T$_{H1}$ pancreatic infiltrates and other inflammatory lesions characterized by T cell infiltration [Bradley L. M. et al., "Islet-specific Th1, but not Th2, cell s secrete multiple chemokines and promote rapid induction of autoimmune diabetes", J Immunol, Vol. 162:2511-2520, (1999)].

Pro-inflammatory cytokines like IL-1$\beta$, IL-6, and TNF-$\alpha$ n the plasma have been primarily detected and involved in the insulin resistance and development of T2D which are kept in check and modulated by the anti-inflammatory and immune suppressive cytokines TGF-$\beta$1 and IL-10 [Alexandraki K. et al., "Inflammatory process in type 2 diabetes: The role of cytokines", Annals of the New York Academy of Sciences, 1084: 89-117, (2006)]; [Kumar N. P. et al. 2015. Eur J Immunol. doi: 10.1002/eji.201545973 ahead of print]. IL-17A is a well-known pro-inflammatory cytokine involved in several autoimmune diseases.

Immune Tolerance

The immune system is tolerant of self-antigens, i.e., it can discriminate between antigenic determinants expressed on foreign substances, and antigenic determinants expressed by tissues of the host. The capacity of the system to ignore host antigens, referred to as immune tolerance or immunological tolerance, is an active process involving the elimination or inactivation of cells that could recognize self-antigens through immunologic tolerance [Fundamental immunology, 4th Edn, William E. Paul, Ed. Lippincott-Raven Publishers, Philadelphia, (1999), at p. 2].

Immune tolerance is classified into 1) central tolerance or 2) peripheral tolerance depending on where the state is originally induced, i.e., whether it is in the thymus and bone marrow (central) or in other tissues and lymph odes (peripheral). The biological mechanisms whereby these forms of tolerance are established are distinct, but the resulting effect is similar [Raker V. K. et al., "Tolerogenic Dendritic Cells for Regulatory T Cell Induction in Man", Front Immunol, Vol., 6(569): 1-11, (2015)].

Central tolerance, the principal way in which the immune system is educated to discriminate self-molecules from non-self-molecules, is established by deleting autoreactive lymphocyte clones at a point before they mature into fully immunocompetent cells. It occurs during lymphocyte development in the thymus and bone marrow for T and B lymphocytes, respectively [Sprent J. et al., "The thymus and central tolerance", Philos Trans R Soc Lond B Biol Sci, Vol. 356(1409): 609-616, (2001)]. In these tissues, maturing lymphocytes are exposed to self-antigens presented by thymic epithelial cells and thymic dendritic cells, or bone marrow cells. Self-antigens are present due to endogenous expression, importation of antigen from peripheral sites via circulating blood, and in the case of thymic stromal cells, expression of proteins of other non-thymic tissues by the action of the transcription factor AIRE [Murphy, Kenneth. Janeway's Immunobiology: 8th ed. Chapter 15: Garland Science. (2012), pp. 611-668]; [Klein L., "Aire gets company for immune tolerance", Cell, Vol. 163(4):794-795, (2015)]. Those lymphocytes that have receptors that bind strongly to self-antigens are removed by means of apoptosis of the autoreactive cells, or by induction of anergy, meaning a state of non-reactivity [Id. at pp. 275-334]. Weakly autoreactive B cells may also remain in a state of immunological inactivity where they do not respond to stimulation of their B cell receptor. Some weakly self-recognizing T cells are alternatively differentiated into natural regulatory T cells (nTreg cells), which act as sentinels in the periphery to lower potential instances of T cell autoreactivity [Id. at pp. 611-668].

The deletion threshold is more stringent for T cells than for B cells since T cells are the main populations of cells that can cause direct tissue damage. Furthermore, it is more advantageous for the organism to let its B cells recognize a wider variety of antigens, so that they can elicit antibodies against a greater diversity of pathogens. Since B cells can only be fully activated after confirmation by more self-restricted T cells that recognize the same antigen, autoreactivity is held in great check [Murphy, Kenneth. Janeway's Immunobiology: 8th ed. Chapter 8: Garland Sciences. pp. 275-334].

This process of negative selection ensures that T and B cells that potentially may initiate a potent immune response to the individual's own tissues are destroyed while preserving the ability to recognize foreign antigens. This step in lymphocyte education is detrimental to preventing autoimmunity. Lymphocyte development and education is most active in fetal development, but continues throughout life as immature lymphocytes are generated, slowing as the thymus degenerates and the bone marrow shrinks in the adult life [Murphy, Kenneth. Janeway's Immunobiology: 8th ed. Chapter 8: Garland Sciences. (2012), pp. 275-334]; [Jiang T. T., "Regulatory T cells: new keys for further unlocking the enigma of fetal tolerance and pregnancy complications", J Immunol., Vol. 192(11): 4949-4956, (2014)].

Peripheral tolerance develops after T and B cells mature and enter the peripheral tissues and lymph nodes [Murphy, Kenneth. Janeway's Immunobiology: 8th ed. Chapter 8: Garland Sciences. pp. 275-334]. It is set forth by a number of overlapping mechanisms that predominantly involve control at the level of T cells, especially CD4$^+$ helper T cells, which orchestrate immune responses and give B cells the confirmatory signals that the B cells need in order to progress to produce antibodies. Inappropriate reactivity toward a normal self-antigen that was not eliminated in the thymus can occur, since the T cells that leave the thymus are relatively but not completely safe. Some will have receptors (TCRs) that can respond to self-antigens that the T cell did not encounter in the thymus [Murphy, Kenneth. Janeway's Immunobiology: 8th ed. Chapter 8: Garland Sciences. (2012), pp. 275-334]. Those self-reactive T cells that escape intra-thymic negative selection in the thymus can inflict cell injury unless they are deleted in the peripheral tissue chiefly by nTreg cells.

CCR7 is a homing receptor important in T, B and dendritic cell migration into secondary lymphoid organs [Forster R. et al., "CCR7 coordinates the primary immune response by establishing functional microenvironments in secondary lymphoid organs", Cell, Vol. 99: 23-33, (1999)]. Multiple roles for CCR7 have been described, [Hopken U. E. et al., "The chemokine receptor CCR7 controls lymph node-dependent cytotoxic T cell priming in alloimmune responses", Eur J Immunol., Vol. 34:461-470, (2004)], including induction and maintenance of central and peripheral tolerance [Hugues S. et al., "Immunity, 16:169-181, (2002)]. Based on the expression of the two isoforms of CD45 leucocyte, T cells are often characterized as naive and/or effector CD45RA$^+$ T cells or memory CD45RO$^+$ T cells.

Autoimmune regulator (Aire), usually expressed in thymic medullary epithelial cells, plays a role in immune tolerance by mediating ectopic expression of peripheral self-antigens and mediating the deletion of auto-reactive T cells. [Metzger T. C. et al., "Control of central and peripheral tolerance by Aire", Immunol. Rev. 2011, Vol. 241: 89-103, (2011)].

Appropriate reactivity towards certain antigens can also be suppressed by induction of tolerance after repeated exposure. Naïve CD4+ helper T cells differentiate into induced Treg cells (iTreg cells) in the peripheral tissue, or accordingly, in nearby lymphoid tissue (lymph nodes, mucosal-associated lymphoid tissue, etc.). This differentiation is mediated by IL-2 produced upon T cell-activation and TGF-3 from any of a variety of sources, including tolerizing dendritic cells (DCs) or other antigen presenting cells [Curotto de Lafaille et al., "Effective recruitment and retention of older adults in physical activity research: PALS study", Immunity, Vol. 30(6): 626-635, (2009)].

T Memory Cells

Following the recognition and eradication of pathogens through adaptive immune responses, the vast majority (90-95%) of T cells undergo apoptosis with the remaining cells forming a pool of memory T cells, designated central memory T cells (T$_{CM}$), effector memory T cells (T$_{EM}$), and resident memory T cells (T$_{RM}$) [Clark, R. A., "Resident memory T cells in human health and disease", Sci. Transl. Med., 7, 269rv1, (2015)].

Compared to standard T cells, these memory T cells are long-lived with distinct phenotypes such as expression of specific surface markers, rapid production of different cytokine profiles, capability of direct effector cell function, and unique homing distribution patterns. Memory T cells exhibit quick reactions upon re-exposure to their respective antigens in order to eliminate the reinfection of the offender and thereby restore balance of the immune system rapidly. Increasing evidence substantiates that autoimmune memory T cells hinder most attempts to treat or cure autoimmune diseases [Clark, R. A., "Resident memory T cells in human health and disease", Sci. Transl. Med., Vol. 7, 269rv1, (2015)].

Autoimmunity

Failure in establishing immunologic tolerance or unusual presentations of self-antigens that give rise to tissue-damaging immune responses directed against antigenic determinants/epitopes on host molecules often result in autoimmune disease, meaning an illness that occurs when the body's tissues are attacked by its own immune system [Round J. L. et al., "Coordination of tolerogenic immune responses by the commensal microbiota", J Autoimmun, Vol. 34(3): 220-225, (2010)]; [Choi J. et al., "The pathogenesis of systemic lupus erythematosus-an update", Curr pin Immunol, Vol. 24(6): 651-657, (2012)]. Exemplary diseases that are autoimmune or have major autoimmune components include, without limitation, Addison's disease, Alopecia Areata (AA), amyloidosis, celiac disease, Crohn's disease, glomerulonephritis, Hashimoto thyroiditis, multiple sclerosis, type 1 diabetes mellitus, myasthenia gravis, polymyositis, psoriasis, rheumatoid arthritis, scleroderma, Sjogren syndrome, and systemic lupus erythematosus. The presence of one autoimmune disease increases the chance for developing another simultaneous autoimmune disease.

Glucose Homeostasis

Normally, following glucose ingestion, the increase in plasma glucose concentration triggers insulin release, which stimulates splanchnic (liver and gastrointestinal tissue) and peripheral glucose uptake and suppresses endogenous (primarily hepatic) glucose production. In healthy adults, blood glucose levels are tightly regulated within a range of 70 to 99 mg/dL, and maintained by specific hormones (e.g., insulin, glucagon, incretins) as well as the central and peripheral nervous system, to meet metabolic requirements. Various cells and tissues within the brain, muscle, gastrointestinal tract, liver, kidney and adipose tissue also are involved in blood glucose regulation by means of uptake, metabolism, storage and secretion [DeFronzo R. A., "Pathogenesis of type 2 diabetes mellitus" Med. Clin. N. Am., Vol. 88: 787-835 (2004)]; Gerich J. E., "Physiology of glucose homeostasis", Diabetes Obes. Metab. Vol. 2: 345-350, (2000)]. Under normal physiologic circumstances, glucose levels rarely rise beyond 140 mg/dL, even after consumption of a high-carbohydrate meal.

Insulin, a potent antilipolytic (inhibiting fat breakdown) hormone, is known to reduce blood glucose levels by accelerating transport of glucose into insulin-sensitive cells and facilitating its conversion to storage compounds via glycogenesis (conversion of glucose toglycogen) and lipogenesis (fat formation) within the islets of Langerhans of the pancreas, β-cells produce insulin.

Glucagon, a hormone that also plays a role in glucose homeostasis, is produced by α-cells within the islets of Langerhans in response to low normal glucose levels or hypoglycemia, and acts to increase glucose levels by accelerating glycogenolysis and promoting gluconeogenesis. After a glucose-containing meal, glucagon secretion is inhibited by hyperinsulinemia, which contributes to suppression of hepatic glucose production and maintenance of normal postprandial glucose tolerance.

Incretins, which include glucose-dependent insulinotropic polypeptide (GIP) and glucagon-like peptide 1 (GLP-1), are also involved in regulation of blood glucose, in part by their effects on insulin and glucagon [Drucker D. J. et al., "The incretin system: glucagon-like peptide-1 receptor agonists and dipeptidyl peptidase-4 inhibitors in type 2 diabetes", Lancet, Vol. 368: 1696-1705, (2006)]. Both GLP-1 and GIP are considered glucose-dependent hormones, meaning they are secreted only when glucose levels increase above normal fasting plasma glucose levels. Normally, these hormones are released in response to meals and, by activating certain receptor on pancreatic β-cells, they aid in stimulation of insulin secretion. When glucose levels are low, however, GLP-1 and GIP levels (and their stimulating effects on insulin secretion) are diminished [Drucker D. J., "The biology of incretin hormones", Cell Metab. Vol. 3: 153-165, (2006)].

The preproglucagon-derived peptides glucagon, GLP1 and GLP2, are encoded by the preproglucagon gene, which is expressed in the central nervous system, intestinal L-cells, and pancreatic and gastric α-cells. A post-translational cleavage by prohormone convertases (PC) is responsible for the maturation of the preglucagon hormone that generates all these peptides. The expression of different PC subtypes in each tissue mediates the production of each different peptide. In α-cells, the predominance of proprotein convertase subtilisin/kexin type 2 (PCSK2) leads to production of glucagon together with the products glicentin, glicentin-repeated pancreatic polypeptide, intervening peptide 1 and the major proglucagon fragment [Dey A. et al., "Significance of prohormone convertase 2, PC2, mediated initial cleavage at the proglucagon interdomain site, Lys70-Arg71, to generate glucagon", Endocrinol., Vol. 146: 713-727, (2005)]. In enteroendocrine cells, PCSK1/3 enzymes cleave the preproglucagon hormone to generate GLP1 and GLP2 along with glicentin, intervening peptide 1 and oxyntomodulin [Mojsov S., "Preproglucagon gene expression in pancreas and intestine diversifies at the level of post-translational processing", J. Biol. Chem., Vol. 261: 11880-11889 (1986)]. Under certain conditions, islet α cells are an extraintestinal site for GLP-1 production [Portha B. et al., "Activation of the GLP-1 receptor signalling pathway: a relevant strategy to repair a deficient beta-cell mass", Exptl Diabetes Res. Article 376509: 1-11, (2011)]. One of the many observed cellular effects of GLP-1 is the inhibition of β-cell $K_{ATP}$ channels, which initiates $Ca^{2+}$ influx through voltage-dependent calcium channels and triggers the exocytotic release of insulin [MacDonald P. E. et al., "The multiple actions of GLP-1 on the process of glucose-stimulated insulin secretion", Diabetes, Vol. 51 (Suppl. 3): S434-S442, (2002)].

Transport of Glucose into Cells

Since glucose cannot readily diffuse through all cell membranes, it requires assistance from both insulin and a family of transport proteins (facilitated glucose transporter [GLUT] molecules) in order to gain entry into most cells [Bryant, et al, Nat. Rev. Mol. Cell Biol. "Regulated transport of the glucose transporter GLUT 4", Vol. 3(4): 267-277, (2002)]. GLUTs act as shuttles, forming an aqueous pore across otherwise hydrophobic cellular membranes, through which glucose can move more easily. Of the 12 known GLUT molecules, GLUT4 is considered the major transporter for adipose, muscle, and cardiac tissue, whereas GLUTs 1, 2, 3, and 8 facilitate glucose entry into other organs (eg, brain, liver). Activation of GLUT4 and, in turn, facilitated glucose diffusion into muscle and adipose tissue, is dependent on the presence of insulin, whereas the function of other GLUTs is more independent of insulin [Uldry M. et al., "The SLC2 family of facilitated hexose and polyol transporters", Thorens B, Eur. J. Physiol. 2004; Vol. 447: 480-489, (2004)].

The majority of glucose uptake (>80%) in peripheral tissue occurs in muscle, where glucose may either be used immediately for energy or stored as glycogen. Skeletal muscle is insulin-dependent, and thus requires insulin for activation of glycogen synthase, the major enzyme that regulates production of glycogen. While adipose tissue is responsible for a much smaller amount of peripheral glucose uptake (2%-5%), it plays an important role in the maintenance of total body glucose homeostasis by regulating the release of free fatty acids (which increase gluconeogenesis) from stored triglycerides, influencing insulin sensitivity in the muscle and liver.

While the liver does not require insulin to facilitate glucose uptake, it does need insulin to regulate glucose output. Thus, for example, when insulin concentrations are low, hepatic glucose output rises. Additionally, insulin helps the liver store most of the absorbed glucose in the form of glycogen.

The kidneys play a role in glucose homeostasis via release of glucose into the circulation (gluconeogenesis), uptake of glucose from the circulation to meet renal energy needs, and reabsorption of glucose at the proximal tubule. The kidneys also aid in elimination of excess glucose (when levels exceed approximately 180 mg/dL, though this threshold may rise during chronic hyperglycemia) by facilitating its excretion in the urine.

Cytoarchitecture of Human Islets

In human islets, insulin-containing $\beta$-cells intermingle with other cell types within the islet, i.e., insulin-, glucagon-, and somatostatin-containing cells are found distributed throughout the human islet [Cabrera O. et al., "The unique cytoarchitecture of human pancreatic islets has implications for islet cell function", Proc. Natl Acad. Sci. U.S., Vol. 103: 2334-2339, (2006)]. Human islets do not show obvious subdivisions, but 90% of $\alpha$-cells are in direct contact with $\beta$-cells, and $\beta$-cells intermingled freely with other endocrine cells throughout the islet. $\beta$, $\alpha$, and $\delta$-cells had equivalent and random access to blood vessels within the islet, ruling out the possibility that the different endocrine cells are organized in layers around blood vessels. These results support a model in which there is no set order of islet perfusion and in which any given cell type can influence other cell types, including its own cell type [G. da Silva Xavier et al.," Per-arnt-sim (PAS) domain-containing protein kinase is downregulated in human islets in type 2 diabetes and regulates glucagon secretion", Diabetologia, Vol. 54: 819-827, (2011)].

Diabetes as an Autoimmune Disease

Diabetes mellitus is a group of metabolic diseases characterized by hyperglycemia. Chronic hyperglycemia is associated with long-term damage, dysfunction, and potential failure of organs, including the eyes, kidneys, nerves, heart and blood vessels. The ideal therapeutic agent for treating diabetes has yet to be developed.

Type 1 Diabetes Mellitus (T1D)

In type 1 diabetes mellitus, 13 cells are destroyed by an autoimmune process and largely replaced by $\alpha$-cells. [Unger R. H. et al., "Paracrinology of islets and the paracrinopathy of diabetes", Proc. Natl Acad. Sci., U.S., Vol. 107(37): 16009-16012, (2010)]. These $\alpha$-cells lack the tonic restraint normally provided by the high local concentrations of insulin from juxtaposed $\beta$-cells, resulting in inappropriate hyperglucagonemia [Raskin P. et al. Glucagon and diabetes. The Medical Clinics of North America 62, 713 (1978)];

[Habener J. F. et al., "Alpha cells some of age", Trends in Endocrinology & Metabolism: $T_{EM}$ Vol. 24, 153-163 (2013)]; [Unger R. H. et al., "Glucagonocentric restructuring of diabetes: a pathophysiologic and therapeutic makeover", J. Clinical Investig. Vol. 122(1): 4-12, (2012)]; [Vuguin P. M. et al. "Novel insight into glucagon receptor action: lessons from knockout and transgenic mouse models", Diabetes, Obesity & Metabolism, Vol. 13(1), 144-150, (2011)], which drives surges of hyperglycemia which increases glucagon secretion [Unger R. H. et al., "Glucagonocentric restructuring of diabetes: a pathophysiologic a d therapeutic makeover", J. Clinical Investig. Vol. 122(1): 4-12, (2012)]. Supernormal insulin levels are needed to match the insulin that neighboring $\beta$-cells give to $\alpha$-cells in normal islets. This results in lifelong hyperinsulinemia, which exposes the subject to frequent incidences of hypoglycemia, which increases such sequelae as accumulation of low density lipoprotein (LDL) in the walls of blood vessels, causing the blockages of atherosclerosis, and coronary artery disease.

Four Pathological Characteristics of T1D are Blood Glucose Levels, Hemoglobin A1C, Glucagon and C-Peptide The immune dysfunction in T1D is complicated, with effects both in pancreatic islets and outside the pancreas. Different components of the immune system [e.g., CD4+, CD8+ T cells, T regulatory cells (Tregs), B cells, dendritic cells (DCs), monocyte/macrophages (Mo/M$\phi$s), natural killer T cells (NKTs)] are all envisioned to actively contribute to auto-immune responses in T1D, thus complicating potential efforts to develop effective and successful treatments or a cure that will work across individuals with the disease. Several clinical trials [Bach J. F., "Anti-CD3 antibodies for type 1 diabetes: beyond expectations", Lancet., Vol. 378: 459-460, (2011)]; [Wherrett D. K. et al., "Antigen-based therapy with glutamic acid decarboxylase (GAD) vaccine in patients with recent-onset type 1 diabetes: a randomized double-blind trial", Lancet., Vol. 378: 319-327, (2011)] highlight the obstacles in developing a therapy and finding a cure for T1D, and point to the need for an approach that produces comprehensive immune modulation at both the local pancreatic and systematic levels rather than targeting the pancreatic effects of one or a few components of the immune system.

Possible triggers for autoimmunity in T1D include, without limitation, genetic, epigenetic, physical, social, and environmental factors, which may act independently or jointly to initiate or potentiate the development of autoimmunity. T1 D-related dysfunction in the immune system has been traced to dysfunctions in multiple cell types and targets including T cells, B cells, regulatory T cells (Tregs), monocytes/macrophages, dendritic cells (DCs), natural killer (NK) cells, and natural killer T (NKT) cells [Lehuen A. et al., "Immune cell crosstalk in type I diabetes", Nat Rev Immunol. Vol. 10: 501-513, (2010)]. Due to the polyclonal nature of T1 D-related autoimmune responses and the global challenges of immune regulation in T1D patients, therapies and trials that only target one or a few components of the autoimmune response are likely to fail just as recent trials involving anti-CD3 Ab for T cells, anti-CD19 Ab for B cells, and GAD 65 vaccination have failed [Bach J F., "Anti CD-3 antibodies for type 1 diabetes: beyond expectations", Lancet, Vol. 378: 459-460, (2011)]; [Mathieu C. et al., "Arresting type I diabetes after diagnosis: GAD is not enough", Lancet, Vol. 378: 291-292, (2011)].

While stem cell therapy has been explored as a means of replacing destroyed pancreatic islet $\beta$-cells, this approach does little in the absence of reducing the underlying auto-immune response.

Attempts to address the underlying autoimmunity in T1D have been unsuccessful [Zhao Y. et al., "Human cord blood stem cells and the journey to a cure for type 1 diabetes", Autoimmun Rev., Vol. 10: 103-107, (2010)] due to the polyclonal nature of the autoimmune response and the global challenges of immune regulation in T1D patients [Zhao Y. et al., "Human cord blood stem cells and the journey to a cure for type 1 diabetes", Autoimmun Rev., Vol. 10: 103-107, (2010)]; [Abdi R. et al., "Immunomodulation by mesenchymal stem cells: a potential therapeutic strategy for type 1 diabetes", Diabetes, Vol. 57: 1759-1767, (2008)]; [Aguayo-Mazzucato C. et al., "Stem cell therapy for type I diabetes", Nat Rev Endocrinol., Vol. 6: 139-148, (2010)]; [Uccelli A. et al., "Mesenchymal stem cells in health and disease", Nat Rev Immunol., Vol. 8: 726-736, (2008)]; [Zhao Y. et al.," Immune regulation of T lymphocyte by a newly characterized human umbilical cord blood stem cell", Immunol Lett., Vol. 108: 78-87, (2007)]. Combinations of individual approaches have been proposed to address these challenges [Aguayo-Mazzucato C et al., "Stem cell therapy for type I diabetes mellitus", Nat Rev Endocrinol, Vol. 6: 139-148, (2010)]; [Zhao Y. et al., "Human cord blood stem cell-modulated regulatory T lymphocytes reverse the auto-immune-caused type 1 diabetes in nonobese diabetic (NOD) mice", PLoS ONE, Vol. 4: e 226, (2009)]; [Zhao Y. et al., "Reversal of type 1 diabetes via islet β-cell regeneration following immune modulation by cord blood-derived multipotent stem cells", BMC Med. Vol. 10(3), 1-11, (2012)], but adherence to these approaches is still complicated and often very costly.

Type 2 Diabetes

Type 2 diabetes (T2D) is a hyperglycemic disorder in which β-cells are present, thus distinguishing it from type 1 diabetes. Although numerous factors contribute to the development of T2D, the central defects are inadequate insulin secretion (insulin deficiency) and/or diminished tissue responses to insulin (insulin resistance) at one or more points in the complex pathways of hormone action [Triplitt C. L., "Examining the mechanisms of glucose regulation", Am. J. Manag. Care, Vol. 18 (1 Suppl) S4-S10, (2012)]. Insulin deficiency and insulin resistance frequently coexist, though the contribution to hyperglycemia can vary widely along the spectrum of T2D.

There is evidence that the etiology of T2D includes an autoimmune component that initiates inflammation affecting pancreatic islet β-cells, which provides new insight into the mechanism and potential treatment of insulin resistance through immune modulation. Some clinical studies showed increasing levels of IL-17 production in T2D patients [Jagannathan-Bogdan M. et al., "Elevated proinflammatory cytokine production by a skewed T cell compartment requires monocytes and promotes inflammation in type 2 diabetes", J Immunol, Vol. 186: 1162-1172 (2011)] and obese patients [Sumarac-Dumanovic M. et al.," Increased activity of interleukin-23/interleukin-17 proinflammatory axis in obese women", Int J Obes (Lond), Vol. 33: 151-156, (2009)]. Other studies show that the level of $T_{H1}$-associated cytokine IL-12 is increased in T2D subjects [Wu H. P. et al., "High interleukin-12 production from stimulated peripheral blood mononuclear cells of type 2 diabetes patients", Cytokine, Vol. 51: 298-304, (2010)].

Tissue Compartments

In multicellular organisms, cells that are specialized to perform common functions are usually organized into cooperative assemblies embedded in a complex network of secreted extracellular macromolecules, the extracellular matrix (ECM), to form specialized tissue compartments.

Individual cells in such tissue compartments are in contact with ECM macromolecules. The ECM helps hold the cells and compartments together and provides an organized lattice or scaffold within which cells can migrate and interact with one another. In many cases, cells in a compartment can be held in place by direct cell-cell adhesion. In vertebrates, such compartments may be of four major types: a connective tissue compartment, an epithelial tissue compartment, a muscle tissue compartment and a nervous tissue compartment, which are derived from three embryonic germ layers: ectoderm, mesoderm and endoderm. The neural tissue compartment and portions of the epithelial compartment are differentiated from the ectoderm; the connective tissue compartment, muscle tissue compartment and further portions of the epithelial tissue compartment are derived from the mesoderm [Kiecker C. et al., "Molecular specification of germ layers in vertebrate embryos", Cell Mol Life Sci., Epub ahead of print, (2015) PMID: 26667903].

Stem Cell Niche

Adult tissue compartments contain endogenous niches of adult stem cells that are capable of differentiating into diverse cell lineages of determined endodermal, mesodermal or ectodermal fate depending on their location in the body. For example, in the presence of an appropriate set of internal and external signals, bone marrow-derived adult hematopoietic stem cells (HSCs) have the potential to differentiate into blood, endothelial, hepatic and muscle cells; brain-derived neural stem cells (NSCs) have the potential to differentiate into neurons, astrocytes, oligodendrocytes and blood cells; gut- and epidermis-derived adult epithelial stem cells (EpSCs) have the potential to give rise to cells of the epithelial crypts and epidermal layers; adipose-derived stem cells (ASCs have the potential to give rise to fat, muscle, cartilage, endothelial cells, neuron-like cells and osteoblasts; and bone-marrow-derived adult mesenchymal stem cells (MSCs) have the potential to give rise to bone, cartilage, tendon, adipose, muscle, marrow stroma and neural cells [Hodgkinson T. et al., "Adult stem cells in tissue engineering", Expert Rev Med Devices, Vol. 6(6): 621-640].

Endogenous adult stem cells are embedded within the ECM component of a given tissue compartment, which, along with support cells, f rm the cellular niche. Such cellular niches within the ECM scaffold together with the surrounding microenvironment contribute important biochemical and physical signals, including growth factors and transcription factors required to initiate stem cell differentiation into committed precursors cells and subsequent precursor cell maturation to form adult tissue cells with specialized phenotypic and functional characteristics [Hodgkinson T. et al., "Adult stem cells in tissue engineering", Expert Rev Med Devices, Vol. 6(6): 621-640].

Growth Factors

Growth factors are extracellular polypeptide molecules that bind to a cell-surface receptor triggering an intracellular signaling pathway, leading to proliferation, differentiation, or other cellular response. These pathways stimulate the accumulation of proteins and other macromolecules, and they do so by both increasing their rate of synthesis and decreasing their rate of d gradation. One intracellular signaling pathway activated by growth factor receptors involves the enzyme PI 3-kinase, which adds a phosphate from ATP to the 3 position of inositol phospholipids in the plasma membrane. The activation of PI 3-kinase leads to the activation of several protein kinases, including S6 kinase. S6 kinase phosphorylates ribosomal protein S6, increasing the ability of ribosomes to translate a subset of mRNAs, most of which encode ribosomal components, as a result of which, protein synthesis increases. When the gene encoding S6 kinase is inactivated in *Drosophila*, cell numbers are normal, but cell size is abnormally small, and the mutant flies are small. Growth factors also activate a translation initiation factor called eIF4E, further increasing protein synthesis and cell growth [Farrar W. L. et al., "Hematopoietic growth-factor signal transduction and regulation of gene expression", Vol. 49: 379-410, (1990)].

Growth factor stimulation also leads to increased production of the gene regulatory protein Myc, which plays a part in signaling by mitogens. Myc increases the transcription of a number of genes that encode proteins involved in cell metabolism and macromolecular synthesis. In this way, it stimulates both cell metabolism and cell growth [Grifoni D. et al., "*Drosophila* Myc: A master regulator of cellular performance", Vol. 1849(5): 570-581].

Some extracellular signal proteins, including platelet-derived growth factor (PDGF), can act as both growth factors and mitogens, stimulating both cell growth and cell-cycle progression. This functional overlap is achieved in part by overlaps in the intracellular signaling pathways that control these two processes. The signaling protein Ras, for example, is activated by both growth factors and mitogens. It can stimulate the PI3-kinase pathway to promote cell growth and the MAP-kinase pathway to trigger cell-cycle progression. Similarly, Myc stimulates both cell growth and cell-cycle progression. Extracellular factors that act as both growth factors and mitogens help ensure that cells maintain their appropriate size as they proliferate [Kim W. S. et al., "The pivotal role of PDGF and its receptor isoforms in adipose-derived stem cells", Vol. 30(7), 793-799].

Since many mitogens, growth factors, and survival factors are positive regulators of cell-cycle progression, cell growth, and cell survival, they tend to increase the size of organs and organisms. In some tissues, however, cell and tissue size also is influenced by inhibitory extracellular signal proteins that oppose the positive regulators and thereby inhibit organ growth. The best-understood inhibitory signal proteins are TGF-β and its relatives. TGF-β inhibits the proliferation of several cell types, either by blocking cell-cycle progression in g1 or by stimulating apoptosis. TGF-β binds to cell-surface receptors and initiates an intracellular signaling pathway that leads to changes in the activities of gene regulatory proteins called Smads. This results in complex changes in the transcription of genes encoding regulators of cell division and cell death.

Bone morphogenetic protein (BMP), a TGF-β family member, helps trigger the apoptosis that removes the tissue between the developing digits in the mouse paw. Like TGF-β, BMP stimulates changes in the transcription of genes that regulate cell death [ehrlich in., "endocytosis and trafficking of bmp receptors: regulatory mechanisms for fine-tuning the signaling response in different cellular contexts", cytokine growth factor rev. Epub ahead of print pmid:26776724, (2016)].

Fibroblast Growth Factor (FGF)

The fibroblast growth factor (FGF) family currently has over a dozen structurally related members. FGF1 is also known as acidic FGF FGF2 is sometimes called basic FGF (bFGF) and FGF7 sometimes goes by the name keratinocyte growth factor. Over a dozen distinct FGF genes are known in vertebrates. They can generate hundreds of protein isoforms by varying their RNA splicing or initiation codons in different tissues. FGFs can activate a set of receptor tyrosine kinases called the fibroblast growth factor receptors (FG-FRs). Receptor tyrosine kinases are proteins that extend through the cell membrane. The portion of the protein that binds the paracrine factor is on the extracellular side, while a dormant tyrosine kinase (i.e., a protein that can phosphorylate another protein by splitting ATP) is on the intracellular side. When the FGF receptor binds an FGF (and only when it binds an FGF), the dormant kinase is activated, and phosphorylates certain proteins within the responding cell, activating those proteins [Li X. et al., "Fibroblast growth factors, old kids on the new block", Semin Cell Dev Biol. Epub ahead of print, PMID: 26768548, (2016)].

FGFs are associated with several developmental functions, including angiogenesis (blood vessel formation), mesoderm formation, and axon extension. While FGFs often can substitute for one another, their expression pattern's give them separate functions. FGF2 is especially important in angiogenesis, whereas FGF8 is involved in the development of the midbrain and limbs [Peng et al., "Stems Ce Is and Development", Vol. 17: 761-774, (2008)].

The expression levels of angiogenic factors, such as VEGF, IGF, PDGF, HGF, FGF, TGFβ, Angiopoeitin-1, and stem cell factor (SCF) have been found to differ amongst bone-derived-, cartilage-derived, and adipose-derived MSCs [Peng et al., "Stems Cells and Development", Vol. 17: 761-774, (2008)].

Insulin-Like Growth Factor (IGF-1)

IGF-1, a hormone similar in molecular structure to insulin, has growth-promoting effects on almost every cell in the body, especially skeletal muscle, cartilage, bone, liver, kidney, nerves, skin, hematopoietic cell, and lungs. It plays an important role in childhood growth and continues to have anabolic effects in adults. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signaling molecules, including SHP2 and STAT5B. Its primary action is mediated by binding to its specific receptor, the Insulin-like growth factor 1 receptor (IGF1R), present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the pituitary gland, released into the blood stream, and then stimulates the liver to produce IGF-1. IGF-1 then stimulates systemic body growth. In addition to its insulin-like effects, IGF-1 also can regulate cell growth and development, especially in nerve cells, as well as cellular DNA synthesis [Aquirre G. A. et al., "Insulin-like growth factor-1 deficiency and metabolic syndrome, J. Trans. Med., Vol. 14(1): 1-23, (2016)]

Transforming Growth Factor beta TGF-β

There are over 30 structurally related members of the TGF-β superfamily, and they regulate some of the most important interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell. The TGF-β superfamily includes the TGF-β family, the activin family, the bone morphogenetic proteins (BMPs), the Vg-1 family, and other proteins, including glial-derived neurotrophic factor (GDNF, necessary for kidney and enteric neuron differentiation) and Mullerian inhibitory factor, which is involved in mammalian sex determination. TGF-β family members TGF-β 1, 2, 3, and 5 are important in regulating the formation of the extracellular matrix between cells and for regulating cell division (both positively and negatively). TGF-β1 increases the amount of extracellular matrix epithelial cell make both by stimulating collagen and fibronectin synthesis and by inhibiting matrix degradation. TGF-βs may be critical in controlling where and when epithelia can branch to form the ducts of kidneys, lungs, and salivary glands Aschner Y. et al., "Transforming Growth Factor-β: Master Regulator of the Respiratory System in Health and Disease", Am J Respir Cell Mol Biol, Epub ahead of print PMID: 26796672, (2016)].

The members of the BMP family were originally discovered by their ability to induce bone formation. Bone formation, however, is only one of their many functions, and they have been found to regulate cell division, apoptosis (programmed cell death), cell migration, and differentiation. BMPs can be distinguished from other members of the TGF-β superfamily by their having seven, rather than nine, conserved cysteines in the mature polypeptide. The BMPs include proteins such as Nodal (responsible for left-right axis formation) and BMP4 (important in neural tube polarity, eye development, and cell death) [Nettersheim D. et al., "BMP Inhibition in Seminomas Initiates Acquisition of Pluripotency via NODAL Signaling Resulting in Reprogramming to an Embryonal Carcinoma, PLOS Genet. Vol. 11(7): 1-26, (2015)].

Stem Cells

The term "stem cells" as used herein refers to undifferentiated cells having high proliferative potential with the ability to self-renew that can generate daughter cells that can undergo terminal differentiation into more than one distinct cell phenotype. Stem cells are distinguished from other cell types by two characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions [Romito A. et al., "Pluripotent Stem Cells: Current Understanding and Future Directions", Stem Cells Int., ID 9451492, 2016)].

Embryonic stem cells (EmSC) are stem cells derived from an embryo that is pluripotent, i.e., they are able to differentiate in vitro into endodermal, mesodermal and ectodermal cell types. [Thomson J. A. et al., "Embryonic stem cell lines derived from human blastocysts", Science, Vol. 282(5391): 1145-1147, (1992)].

Adult (somatic) stem cells are undifferentiated cells found among differentiated cells in a tissue or organ. Their primary role in vivo s to maintain and repair the tissue in which they are found. Adult stem cells have been identified in many organs and tissues, including brain, bone marrow, peripheral blood, blood vessels, skeletal muscles, skin, teeth, gastrointestinal tract, liver, ovarian epithelium, and testis. Adult stem cells are thought to reside in a specific area of each tissue, known as a stem cell niche, where they may remain quiescent (non-dividing) for long periods of time until they are activated by a normal need for more cells to maintain tissue, or by disease or tissue injury. Examples of adult stem cells include, but not limited to, hematopoietic stem cells, and mesenchymal stem cells [Dzierzak E. et al., "Of lineage and legacy: the development of mammalian hematopoietic stem cells", Nature Immunol., Vol. 9(2): 129-136, (2008)].

Hematopoietic Stem Cells (HSCs)

Hematopoietic stem cells (also known as the colony-forming unit of the myeloid and lymphoid cells (CFU-M,L), or CD34+ cells) are rare pluripotent cells within the blood-forming organs that are responsible for the continued production of blood cells during life [Li Y. et al., "Inflammatory signaling regulates embryonic hematopoietic stem and progenitor cell production", Genes Dev., Vol. 28(23): 2596-2612, (2014)].

While there is no single cell surface marker exclusively expressed by hematopoietic stem cells, it generally has been accepted that human HSCs have the following antigenic profile: CD34+, CD59+, Thyl+(CD90), CD38 low/- and C-kit-/low. CD45 is also a common marker of HSCs, except platelets and red blood cells. HSCs can generate a variety of cell types, including erythrocytes, neutrophils, basophils, eosinophils, platelets, mast cells, monocytes, tissue macrophages, osteoclasts, and the T and B lymphocytes. The regulation of hematopoietic stem cells is a complex process involving self-renewal, survival and proliferation, lineage commitment and differentiation and is coordinated by diverse mechanisms including intrinsic cellular programming and external stimuli, such as adhesive interactions with the micro-environmental stroma and the actions of cytokines.

Different paracrine factors are important in causing hematopoietic stem cells to differentiate along particular pathways. Paracrine factors involved in blood cell and lymphocyte formation are called cytokines. Cytokines can be ma e by several cell types, but they are collected and concentrated by the extracellular matrix of the stromal (mesenchymal) cells at the sites of hematopoiesis. For example, granulocyte-macrophage colony-stimulating factor (GM-CSF) and the multilineage growth factor IL-3 both bind to the heparan sulfate glycosaminoglycan of the bone marrow stroma. The extracellular matrix then presents these factors to the stem cells in concentrations high enough to bind to their receptors [Alvarez S. et al., "GM-CSF and IL-3 activities in schistosomal liver granulomas are controlled by stroma-associated heparan sulfate proteoglycans", J Leukoc Biol., Vol. 59(3): 435-441, (1996)].

Mesenchymal Stem Cells (MSCs)

Mesenchymal stem cells (MSCs) (also known as bone marrow stromal stem cells or skeletal stem cells) are non-blood adult stem cells found in a variety of tissues. They are characterized by their spindle-shape morphologically; b the expression of specific markers on their cell surface; and by their ability, under appropriate conditions, to differentiates along a minimum of three lineages (osteogenic, chondrogenic, and adipogenic) [Najar M. et al., "Mesenchymal stromal cells and immunomodulation: A gathering of regulatory immune cells", Cytotherapy, Vol. 18(2): 160-171, (2016)].

No single marker that definitely delineates MSCs in vivo has been identified due to the lack of consensus regarding the MSC phenotype, but it generally is considered that MSCs are positive for cell surface markers CD105, CD166, CD90, and CD44 and that MSCs are negative for typical hematopoietic antigens, such as CD45, CD34, and CD14. As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic supporting stroma. Studies using transgenic and knockout mice and human musculoskeletal disorders have reported that MSC differentiate into multiple lineages during embryonic development and adult homeostasis [Najar M. et al., "Mesenchymal stromal cells and immunomodulation: A gathering of regulatory immune cells", Cytotherapy, Vol. 18(2): 160-171, (2016)].

Analysis of the in vitro differentiation of MSCs under appropriate conditions that recapitulate the in vivo process have led to the identification of various factors essential for stem cell commitment. Among them, secreted molecules and their receptors (e.g., transforming growth factor-(β), extracellular matrix molecules (e.g., collagens and proteoglycans), the actin cytoskeleton, and intracellular transcription factors (e.g., Cbfal/Runx2, PPARγ, Sox9, and MEF2) have been shown to play important roles in driving the commitment of multipotent MSCs into specific lineages, and maintaining their differentiated phenotypes [Davis L. A. et al., "Mesodermal fate decisions of a stem cell: the Wnt switch", Cell Mol Life Sci., Vol. 65(17): 2568-2574, (2008)].

Bone marrow contains a variety of precursor and mature cell types, including hematopoietic cells, which are precursor cells of mature blood cells and stromal cells that are precursors of a broad spectrum of connective tissue cells, both of which are capable of differentiating into other cell types [Wang J. S. et al., "The coronary delivery of marrow stromal cells for myocardial regeneration: pathophysiologic and therapeutic implications", J. Thorac. Cardiovasc. Surg., Vol. 122: 699-705, (2001)]; [Tomita S. et al., "Autologous transplantation of bone marrow cells improves damaged heart function", Circulation, Vol. 100 (Suppl. II): 247-256, (1999)]; [Saito, T. et al., "Myogenic Expression of Mesenchymal Stem Cells within Myotubes of mdx Mice in Vitro and in Vivo", Tissue Eng., Vol. 1: 327-343, (1995)]. Unmodified (i.e., not fractionated) marrow or blood-derived cells have been used in several clinical studies, for example, [Hamano K. et al., "Local implantation of autologous bone marrow cells for therapeutic angiogenesis in patients with ischemic heart disease: clinical trial and preliminary result", Japan Cir. J., Vol. 65: 845-847, (2001)]; [Strauer B. E., et al., "Repair of infarcted myocardium by autologous intracoronary mononuclear bone marrow cell transplantation in humans", Circulation, Vol. 106: 1913-1918, (2002)]; [Assmus et al., "Transplantation of Progenitor Cells and Regeneration Enhancement in Acute Myocardial Infarction (TOP-CARE-AMI)", Circulation., Vol. 106: 3009-3017, (2002)]; [Dobert N. et al., "Transplantation of Progenitor Cells and Regeneration Enhancement in Acute Myocardial Infarction (TOPCARE-AMI)", Eur. J. Nuel. Med. Mol. Imaging., Vol. 8:1146-51, (2004)]; [Wollert K. C. et al., "Intracoronary autologous bone-marrow cell transfer after myocardial infarction: the BOOST randomized controlled clinical trial", Lancet, Vol. 364: 141-148, (2004)]. Since the mononuclear fraction of bone marrow contains stromal cells, hematopoietic precursors, and endothelial precursors, the relative contribution of each of these populations to the observed effects, if any, remains unknown.

Mouse models have suggested that modulation of Tregs can potentiate the treatment of autoimmune diseases [Allenbach et al., "Role of regulatory T cells in a new mouse model of experimental autoimmune myositis", Am J. Pathol., Vol. 174(3): 989-998, (2014)].

Umbilical Cord Stem Cells

Umbilical cord stem cells are examples of cells of the epithelial tissue compartment. In vivo, two types of umbilical stem cells can be found, namely hematopoietic stem cells (UC-HS) and mesenchymal stem cells, which in turn can be found in umbilical cord blood (UC-MS) or in Wharton's jelly (UC-MM). The blood of the umbilical cord has long been in the focus of attention of researchers as an important source of stem cells for transplantation for several reasons: (1) it contains a higher number of primitive hematopoietic stem cells (HSC) per volume unit, which proliferate more rapidly, than bone marrow; (2) there is a lower risk of rejection after transplantation; (3) transplantation does not require a perfect HLA antigen match (unlike in the case of bone marrow); (4) UC blood has already been successfully used in the treatment of inborn metabolic errors; and (5) there is no need for a new technology for collection and storage of the mononuclear cells from umbilical cord blood, since such methods are long established [Mihu C. et al., "Isolation and characterization of stem cells from the placenta and the umbilical cord", Romanian Journal of Morphology and Embryology, 2008, 49(4):441-446, (2008)].

Umbilical cord (UC) vessels and the surrounding mesenchyma (including the connective tissue known as Wharton's jelly) derive from the embryonic and/or extraembryonic mesoderm. Thus, these tissues, as well as the primitive germ cells, are differentiated from the proximal epiblast, at the time of formation of the primitive line of the embryo, containing MSC and even some cells with pluripotent potential. The UC matrix material is speculated to be derived from a primitive mesenchyma, which is in a transition state towards the adult bone marrow mesenchyma [Mihu C. et al., "Isolation and characterization of stem cells from the placenta and the umbilical cord", Romanian Journal of Morphology and Embryology, 2008, Vol. 49(4):441-446, (2008)].

The blood from the placenta and the umbilical cord is relatively easy to collect in usual blood donation bags, which contain anticoagulant substances. Mononuclear cells are separated by centrifugation on a Ficoll gradient, from which the two stem cell populations will be separated: (1) hematopoietic stem cells (HSC), which express certain characteristic markers (CD34, CD133); and (2) mesenchymal stem cells (MSC) that adhere to the culture surface under certain conditions (e.g., modified McCoy medium and lining of vessels with Fetal Bovine Serum (FBS) or Fetal Calf Serum (FCS) [Munn D. et al., "Prevention of allogeneic fetal rejection by tryptophan catabolism", Science, Vol. 281: 1191-1193, (1998)]; [Munn D. et al., "Inhibition of T cell proliferation by macrophage tryptophan catabolism", J Exp Med, Vol. 189: 1363-1372, (1999)]. Umbilical cord blood MSCs (UC-MS) can produce cytokines, which facilitate grafting in the donor and in vitro HSC survival compared to bone marrow MSC [Zhang X. et al., "Successful immortalization of mesenchymal progenitor cells derived from human placenta and the differentiation abilities of immortalized cells", Biochem Biophys Res Commun, Vol. 351: 853-859, (2006)].

A population of cord blood-derived multipotent stem cells (CB-SCs) of very low immunogenicity that display embryonic cell markers (for example, transcription factors OT-4 and Nanog, stage specific embryonic antigen (SSEA)-3 and SSEA-4), and leukocyte common antigen CD45, but are negative for CD34, that distinguish them from other known stem cell types, including hematopoietic stem cells (HSCs), mesenchymal stem cells (MSCs), and monocytes/macrophages (Mo/Mφ), have been described [Zhao Y. et al., "Successful immortalization of mesenchymal progenitor cells derived from human placenta and the differentiation abilities of immortalized cells", Exp. Cell Res., Vol. 312: 2454-2464, (2006)]; [Zhao Y. et al., "Reversal of type 1 diabetes via islet β-cell regeneration following immune modulation by cord blood-derived multipotent stem cells", BMC Med., Vol. 10(3), 1-11, (2012)]; [Zhao Y. et al., "Immune regulation of T lymphocyte by a newly characterized human umbilical cord blood stem cell", Immunol. Lett., Vol. 108: 78-87, (2010)].

Human cord blood-derived stem cells (CB-SCs) and mesenchymal stem cells (MSCs) have been shown to modulate immune activity in vitro [Zhao Y. et al., "Human cord blood stem cells and the journey to a cure for type 1 diabetes", Autoimmun Rev., Vol. 10: 103-107, (2010); [Abdi R. et al., "Immunomodulation by mesenchymal stem cells, A potential therapeutic strategy for type I diabetes", Diabetes, Vol. 57: 1759-1767, (2008)]; [Aguayo-Mazzucato C. et al., "Stem cell therapy for type diabetes", Nat Rev Endocrinol, Vol. 6: 139-148, (2010)]; [Uccelli A. et al., "Mesenchynmal stem cells in health and disease", Nat Rev Immunol, Vol. 8: 726-736, (2008)]; [Zhao Y. et al.," Immune regulation of T lymphocyte by a newly characterized human umbilical cord blood stem cell", Immunol Lett., Vol. 108: 78-87, (2007)]. Subsequent studies have demonstrated that CB-SCs can be used to alter immune function and improve markers of T1D in non-obese diabetic mice (NOD) [Zhao Y. et al., "Human cord blood stem cell-modulated regulatory T lymphocytes reverse the autoimmune-caused type 1 diabetes in nonobese diabetic (NOD) mice", PLoS ONE, Vol. 4: e4226, (2009)], and CB-SCs have been shown to modulate the immune function of T1D patient-derived islet cell-specific pathogenic T cell clones in co-culture [Zhao Y. et al., "Human cord blood stem cells and the journey to a cure for type 1 diabetes", Autoimmun Rev., Vol. 10: 103-107, (2010)).

Studies in animal models substantiate these findings, and suggest that CB-SC treatment may allow regeneration of the native population of islet β-cells without stem cell transplantation [Zhao Y. et al., "Human cord blood stem cell-modulated regulatory T lymphocytes reverse the autoimmune-caused type 1 diabetes in nonobese diabetic (NOD) mice", PLoS ONE, Vol. 4: e4226, (2009)]; [Zhao Y. et al., "Human cord blood stem cells and the journey to a cure for type 1 diabetes", Autoimmun Rev., Vol. 10: 103-107, (2010].

Zhao et al developed a procedure in which a patient's blood is circulated through a continuous closed loop system termed a bioreactor device that separates lymphocytes from the whole blood, briefly co-cultures the lymphocytes in the presence of adherent CB-SCs, and then returns the "educated" lymphocytes to the patient's circulation [Zhao Y. et al., "Reversal of type 1 diabetes via islet beta cell regeneration following immune modulation by cord blood-derived multipotent stem cells", BMC Med, Vol. 10:3, (2012]. In an open-label phase 1/2 study, twelve (12) patients of Asian descent with T1D received a single treatment with the bioreactor device, and three patients of Asian descent received a single treatment with the bioreactor device without adherent CB-SCs (i.e., process only control). A 16-gauge IV needle was placed in the left (or right) median cubital vein, and the patient' blood was passed through a Blood Cell Separator MCS+(Haemonetics®, Braintree, MA) at 35 mL/min for 6 to 7 hours to isolate lymphocytes in accordance with the manufacturer's recommended protocol. The collected lymphocytes were transferred into the device for exposure to allogeneic CB-SCs (or process control without CB-SCs), and other blood components were returned to the patient. After 2 to 3 hours in the device, lymphocytes were returned to the patient's circulation via a dorsal vein in the hand under gravity flow control (2 to 3 mL/min) with physiological saline. Approximately 10,000 mL of blood was processed during the procedure resulting in approximately two repeated educations for the lymphocyte fraction. Patients were hospitalized for two days to monitor temperature and to conduct routine laboratory blood tests for adverse reactions following treatments.one such treatment.

Initial results based on a small group of Asian participants showed that the therapy was well tolerated in all participants with minimal pain from two venipunctures and no adverse events, and can markedly improve C-peptide levels, reduced median glycated hemoglobin A1C (HbA1C) values, and decrease the median daily dose of insulin in patients with some residual R-cell function (n=6).

The percentage of CD4+CD25+ Foxp3+ Tregs in peripheral blood of participants was significantly increased 4 weeks after bioreactor device therapy, whereas the percentage of Tregs in peripheral blood of participants receiving sham therapy was unchanged from baseline. Participants in the treatment group exhibited significant increases in plasma level of TGFβ1 at the 4-week follow-up, but did not exhibit changes in the plasma level of IL-10, compared to sham control. Flow cytometry revealed an increase in CD28 and inducible costimulatory (ICOS) which are essential for the establishment, maintenance and efficacy of Tregs [Bour-Jourdan H. et al., "Intrinsic and extrinsic control of peripheral T-cell tolerance by co stimulatory molecules of the CD28/B7 family", Immunol. Rev., Vol 241: 180-205, (2011)]; [Hornbach A. A. et al., "Effective proliferation of human regulatory T cells requires a strong costimulatory CD28 signal that cannot be substituted by IL-2", J. Immunol., Vol. 179: 7924-7931, (2007)]; [Hori S., "Effective proliferation of human regulatory T cel s requires a strong costimulatory CD28 signal that cannot be substituted by IL-2", Eur. J. Immunol., Vol. 40: 664-667, (2010)]; [Tang Q et al., "CTLA4 Expression Is an Indicator and Regulator of Steady-State CD4+FoxP3+ T Cell Homeostasis", J. Immunol., Vol., 171: 3348-3352, (2003)]; [Vang K. B., et al., "Cutting edge: CD28 and c-Rel-dependent pathways initiate regulatory T cell development", J. Immunol., Vol. 184: 4074-77, (12010)]; [Herman A. E. et al., "CD4+CD25+T regulatory cells dependent on ICOS promote regulation of effector cells in the prediabetic lesion", J. Expt Med. Vol. 199: 1479-1489, (2004)]; [Gotsman I. et al., "Impaired regulatory T-cell response and enhanced atherosclerosis in the absence of inducible costimulatory molecule", Circulation, Vol. 114: 2047-2055, (2006)]; [Nurieva R. L. et al., "Molecular mechanisms for T cell tolerance", Immunol. Rev. Vol, 241: 133-144, (2014)]; [Rudensky A. Y., "Regulatory T cells and Foxp3", Immunol. Rev., Vol. 241: 260-268, (2011)] in lymphocytes 4 weeks after bioreactor device therapy, but levels of both molecules were unchanged in sham controls. Expression of IL-4 and IL-12 was significantly increased, and expression of IL-5 and IL-13 was decreased. The production of pro-inflammatory IL-17A was also decreased 4 weeks after treatment. No changes were observed in levels of these cytokines after sham therapy.

Treatment with the continuous closed loop system, while suggestive, is impractical for commercial use, in that the efficiency of incubation is limited because it requires a human attendant for the duration of its use, and is expensive to employ.

The described invention provides a practical discontinuous system employing a processing facility for preparing an educated mononuclear cell product. The treatment only requires two venipunctures, carries a lower risk of infection than a typical blood transfusion, and does not introduce stem cells or used reagents into patients. In addition, since CB-SCs have very low immunogenicity, it eliminates the need for human leukocyte antigen (HLA) matching prior to treatment. This approach may provide CB-SC-mediated immune modulation therapy for multiple autoimmune diseases, while mitigating the safety and ethical concerns associated with other approaches. The relative simplicity of the approach may also provide cost and time savings relative to other approaches.

SUMMARY OF THE INVENTION

According to one aspect, the described invention provides a method for treating a disease characterized by lymphocyte autoreactivity, comprising, in order: (1) acquiring under sterile conditions a whole blood sample containing mononuclear cells from a subject diseased with the disease characterized by lymphocyte autoreactivity; (2) transporting the whole blood sample of (1) to a processing facility (3) sterilely purifying the mononuclear cells (MNC) from the whole blood sample to for a mononuclear cell preparation; (4) introducing the mononuclear cell preparation into a bioreactor device comprising a viable population of adherent umbilical cord blood stem cells (UC-SCs), wherein the adherent UC-SCs are at least 80% confluent; (5) co-culturing the mononuclear cell preparation with the CB-SCs so that the mononuclear cells in the mononuclear cell preparation and the CB-SCs can interact for at least 0.1 hour, at least 0.2 hour, at least 0.3 hour, at least 0.4 hour, at least 0.5 hour, a: least 0.6 hour, at least 0.7 hour, at least 0.8 hour, at least 0.9 hour, at least 1.0 hour, at least 1.5 hours, at least 2 hours, at least 2.5 hours, at least 3 hours, at least 3.5 hours, at least 4 hours, at least 4.5 hours, at least 5 hours, at least 5.5 hours, at least 6 hours, at least 6.5 hours, at least 7 hours, at least 7.5 hours, or at least 8 hours under sterile conditions to form an educated mononuclear cell product; (6) harvesting the educated mononuclear cell product under sterile conditions from the bioreactor device; (7) Confirming purity, sterility, and percent viability of the educated mononuclear cell product having at least $10^4$, at least $10^5$, at least $10^6$, at least $10^7$, at least $10^8$, at least $10^9$, or at least $10^{10}$ mononuclear cells; (8) transporting the educated mononuclear cell product to a clinical facility for intravascular infusion into the subject; and (9) infusing a therapeutically effective amount of the educated mononuclear cell product intravascularly into the subject; and (10) repeating steps (1) through (9) in order, at a plurality of infusion dates as needed over a subject's lifetime, wherein the therapeutically effective amount of the educated mononuclear cell product may be effective to modulate autoreactivity in a T cell compartment of the subject, and to reduce symptoms of the disease characterized by lymphocyte autoreactivity. According to one embodiment, the subject is of Caucasian ethnicity. According to another embodiment, the disease characterized by lymphocyte autoreactivity is an autoimmune disease. According t another embodiment, the autoimmune disease is diabetes. According to another embodiment, the autoimmune disease is type 1 diabetes. According to another embodiment, the autoimmune disease is type 2 diabetes. According to another embodiment, the umbilical cord blood mononuclear stem cells are allogeneic to the isolated mononuclear cells. According to another embodiment, the method further comprises preparing the biomedical device comprising UC-SCs by a process comprising, in order: (a) obtaining a fresh cord blood unit obtained from healthy donors; (b) isolating a mononuclear cell fraction from the umbilical cord blood by density gradient centrifugation; (c) removing red blood cells; (d) washing the UC-mononuclear cells with a physiological buffered saline; (e) seeding the UC mononuclear cells in the bioreactor in a serum-free culture medium at a seeding density of at least $1 \times 10^6$ cells; (f) culturing the UC mononuclear cells in a serum-free culture medium, changing half/the medium every 2-3 days to remove non-adherent cells, for at least 10 days to grow to at least 80% confluence; and (g) confirming sterility and viability of a sample of the confluent adherent UC-SCs in (f).

According to another aspect, the described invention provides a pharmaceutical comprising a therapeutic amount of an educated mononuclear cell product, wherein the educated mononuclear cell product is produced by a process comprising: (1) acquiring under sterile conditions a whole blood sample containing mononuclear cells from a subject diseased with the disease characterized by lymphocyte autoreactivity; (2) transporting the whole blood sample of (1) to a processing facility; (3) sterilely purifying the mononuclear cells (MNC) from the whole blood sample to form a mononuclear cell preparation; (4) introducing the mononuclear cell preparation into a bioreactor device comprising a viable population of adherent umbilical cord blood stem cells (UC-SCs), wherein the adherent C-SCs are at least 80% confluent; (5) co-culturing the mononuclear cell preparation with the CB-SCs so that the mononuclear cells in the mononuclear cell preparation and the CB-SCs can interact for at least 0.1 hour, at least 0.2 hour, at least 0.3 hour, at least 0.4 hour, at least 0.5 hour, at least 0.6 hour, at least 0.7 hour, at least 0.8 hour, at least 0.9 hour, at least 1.0 hour, at least 1.5 hours, at least 2 hours, at least 2.5 hours, at least 3 hours, at least 3.5 hours, at least 4 hours, at least 4.5 hours, at least 5 hours, at least 5.5 hours, at least 6 hours, at least 6.5 hours, at least 7 hours, at least 7.5 hours, or at least 8 hours under sterile conditions to form the educated mononuclear cell product, wherein the therapeutically effective amount of the educated mononuclear cell product is effective to modulate autoreactivity in a T cell compartment of the subject, and to reduce symptoms of the disease characterized by lymphocyte autoreactivity, and wherein the educated mononuclear cell product comprises: at least $1 \times 10^8$, t least $1 \times 10^9$, or at least $1 \times 10^{10}$ mononuclear cells; and (ii) a modulated population of T cells selected from the group consisting of $T_{EM}$ CD4$^+$, $T_{EM}$ CD8*, $T_{CM}$ CD4+CD4 RA-CCR7*, $T_{CM}$ CD8+CCR7*, $T_{CM}$ CD45RO$^+$ CCR7*, $T_{EM}$ CD45RO$^+$ CCR7$^-$, $T_{CM}$ CD4$^+$, $T_{CM}$ CD8+, naïve CD4$^+$ CCR7+, naïve CD8$^+$CCR7+, naïve CD4$^+$ CD45RA$^+$ CCR7+, $T_{EM}$ CCR7+CD4+, $T_{EM}$ CCR7+CD8+, $T_{EM}$ CD45RO$^+$CD62L$^-$, $T_{EM}$ CD8+CCR7+, CD4+HLA-DR+ and CD8+HLA-DR+cells. According to one embodiment, the educated mononuclear cell product comprises a reduced subpopulation of $T_{EM}$ CD4$^+$ cells and the subpopulation of $T_{EM}$ CD8$^+$ cells compared to an untreated control. According to another embodiment, the educated mononuclear cell product comprises an increased subpopulation of $T_{CM}$ CD4+ CD45RA-CCR7$^+$ cells and an increased subpopulation of $T_{CM}$ CD8$^+$CCR7$^+$ cells compared to an untreated control. According to another embodiment, the educated mononuclear cell product comprises an increased subpopulation of $T_{CM}$ CD45RO+CCR7$^+$ cells compared to an untreated control. According to another embodiment, the educated mononuclear cell product comprises a reduced subpopulation of $T_{EM}$ CD45RO$^+$ CCR7$^-$ cells compared to an untreated control. According to another embodiment, the educated mononuclear cell product comprises an increased subpopulation of $T_{CM}$ CD4$^+$ cells and subpopulation of $T_{CM}$ CD8$^+$ cells compared to an untreated control. According to another embodiment, the educated mononuclear cell product comprises an increased subpopulation of naïve CD4+CC 7+ T cells and subpopulation of naïve CD8*CCR7*T cells compared to an untreated control.

According to another embodiment, the educated mononuclear cell product comprises an increased subpopulation of naive CD4+CD45RA+CCR7+ T cells compared to an untreated control. According to another embodiment, the educated mononuclear cell product comprises a reduced subpopulation of $T_{EM}$ CD4$^+$ cells and subpopulation of $T_{EM}$ CD8$^+$ cells compared to an untreated control. According to another embodiment, the educated mononuclear cell product comprises an increased subpopulation of $T_{EM}$ CCR7$^+$ CD4$^+$ cells and subpopulation of $T_{EM}$ CCR7+CD8$^+$ cells compared to an untreated control. According to another embodiment, the educated mononuclear cell product comprises a reduced subpopulation of CD4+HLA$^-$DR$^+$ T cells and subpopulation of CD8+HLA$^-$DR$^+$ T cells compared to an untreated control. According to another embodiment, the educated mononuclear cell product comprises an increased subpopulation of $T_{EM}$ CD45RO$^-$ CD62L-cells compared to an untreated control.

According to another embodiment, the disease characterized by lymphocyte autoreactivity is type 1 diabetes, and the modulated autoreactivity in a T cell compartment of the subject comprises an improvement of β-cell function. According to another embodiment, the improvement of β-bell function comprises an increase in serum C-peptide levels. According to another embodiment, the composition further comprises a therapeutic agent selected from the group consisting of insulin, an insulin analog, a biguanide, a thiazolidinedione, a secretagogue, a sulfonylurea, a non-sulfonylurea secretagogue, a glinide, metformin, an alpha-glucosidase inhibitor, a meglitinide, an alpha-glucosidase inhibitor, a glucagon-like peptide 1 (GLP-1) mimetic, a glucagon-like peptide 1 (GLP-1) agonist, an amylin analogue, a dipeptidyl peptidase-4 Inhibitor, an incretin mimetic, a gastric inhibitory peptide analog, an amylin analog, a glycosuric, a finasteride, dutasteride, minoxidil, ketoconazole, spironolactone, flutamide, a cyclosporin, clobetasol, an anti-CD3 antibody, a small molecule activator of the insulin receptor, fluocinonide or a combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3a shows 12-week follow-up HbA1C levels in T2D subjects. FIG. 3b shows analysis of insulin sensitivity by HOMA-IR C-peptide at 4 weeks post treatment.

FIG. 3c depicts 56-week follow-up C-peptide levels in Group C T2D subjects with impaired islet β-cell function. FIG. 3d shows analysis of islet β-cell function by HOMA-B C-peptide at 12-week follow-up post treatment.

FIG. 4a shows up-regulation of plasma level of TGF-β1 in T2D patients at baseline and 4 weeks after treatment. FIG. 4b shows flow analysis of intra-cellular cytokines demonstrating differential effects on key interleukins at 4 weeks post treatment.

FIG. 4c shows down-regulation percentage of CD86+ CD14$^+$ monocytes in T2D patients at baseline and 4 weeks after treatment. FIG. 4d depicts flow analysis of CD4+ CD25+ Foxp3+ Tregs demonstrating no change in the percentage of Tregs at 4 weeks post treatment.

FIG. 5a shows the co-culture of CB-SC with monocytes (bottom left panel) for 18 hrs by phase contrast microscopy. CB-SCs co-culture with lymphocytes (top right panel) served as control. The impaired CB-SCs after co-culture with monocytes were restored to expansion and became 90~100% confluent after 7-10 days (bottom right). Original magnification, ×100. FIG. 5b shows apoptotic analysis of floating cells from the co-culture of CB-SCs with monocytes for 18 hrs. FIG. 5c shows expression of the cellular inhibitor of apoptosis protein (cIAP) 1, not cIAP2, in four preparations of CB-SCs as determined by Western blot. FIG. 5d Western blotting shows the expression of tumor necrosis factor receptor II (TNF R II), not TNF-RI, in four preparations of CB-SCs. FIG. 5e TNF-α suppresses the proliferation of CB-SCs in a dose-response manner. Cell proliferation was evaluated using CyQUANTR Cell Proliferation Assay Kit (Millipore, OR). FIG. 5f shows blocking experiment with iNOS inhibitor 1400W demonstrates that CB-SC-derived nitric oxide (NO) contributes to the immune modulation of CB-SCs on monocytes. Monocytes were initially stimulated with lipopolysaccharide (LPS, 10 μg/mL) for 8 hours, and then co-cultured with CB-SCs at ratio 1:5 of CB-SCs:monocytes for 48 hrs in the presence or absence of 1400W (100 nM), followed by real time PCR analysis by using Human Th17 for Autoimmunity & Inflammation PCR Array kit (SABiosciences, Valencia, CA).

FIGS. 7a-g show changes in immune markers in Caucasian T1D patients after treatment with the continuous SCE system in a phase 1/2 clinical trial. All subjects received two treatments with the discontinuous SCE system. At time 0, patients received a first treatment; all subjects received a second treatment after three months. Follow-up visits were scheduled 2, 8, 12, 26, 40 and 56 weeks after treatment for clinical assessments and laboratory tests. Patient lymphocytes were isolated from peripheral blood by Ficoll-Hypaque (γ=1.077) for flow cytometry analyses in T1D patients at baseline and different time-points after treatment. Isotype-matched IgG served as control. FIG. 7a demonstrates immune cell quantification in peripheral blood.

FIG. 7b shows percentage of CD4+ and CD8$^+$ T cells in peripheral blood. FIG. 7c displays flow analysis of naive CD4$^+$ and CD8$^+$ T cells in peripheral blood, demonstrating an increase in the percentage of naive CD4+ T cells at 26 weeks post treatment. FIG. 7d shows flow analysis of CD4+$T_{CM}$ and CD8$^+$ $T_{CM}$ cells in peripheral blood, demonstrating an increase in the percentage of CD4$^+$ $T_{CM}$ cells at 18 weeks post treatment. FIG. 7e depicts flow analysis of CD4+$T_{EM}$ and CD8$^+$ $T_{EM}$ cells in peripheral blood, demonstrating a decline in the percentage of CD4+$T_{EM}$ an CD8$^+$ $T_{EM}$ cells at 18 weeks and 26 weeks respectively post treatment. FIG. 7f shows flow analysis of CD4$^+$ HLA$^-$DR$^+$ in peripheral blood, demonstrating a decline in their percentages at 26 weeks post treatment. FIG. 7g shows flow analysis of CD8*HLA$^-$DR$^+$ T cells in peripheral blood, demonstrating a decline in their percentages at 26 weeks post treatment. Data are shown as mean±SD for all statistical analysis (FIGS. 7a-g), paired Student's t test (FIGS. 7a-g).

FIG. 8*a* shows up-regulation of CCR7 expression on Naïve CD4$^+$ T cells. FIG. 8*b* depicts up-regulation of CCR7 expression on Naïve CD8$^+$ T cells. FIG. 8*c* demonstrates up-regulation of CCR7 expression on CD4+T$_{CM}$ cells. FIG. 8*d* shows up-regulation of CCR7 expression on CD8+T$_{CM}$ cells. FIG. 8*e* depicts modulation of CCR7 expression on CD4$^+$ and CD8$^+$ T$_{EM}$ cells. Data are shown as mean±SD for all statistical analyses (FIGS. 8*a-e*), paired Student's t test (FIGS. 8*a-e*).

FIGS. 9*a-c* show confirmation of the up-regulation of CCR7 expression on T cells by ex vivo studies. FIG. 9*a* shows phase contrast micrographs showing the formation of cell clusters with different sizes in a mixed leukocyte reaction (MLR), in absence (left panel) of CB-SCs, but the cell clusters disappeared in the presence (right panel) of CB-SCs. (b and c) Cells from the mixed leukocyte reactions were collected for flow analysis after co-culture for 5 days. Responder cells (R) were co-cultured with allogeneic stimulator cells (S) in the presence of CB-SCs. The ratio of R:S was 1:2; the ratio of CB-SCs:R was 1:10. FIG. 9*b* shows flow cytometry of CCR7 expression on the gated CD4$^+$ T cells and CD8$^+$ T cells. The untreated CD4$^+$ lymphocytes showed two populations: one was positive for CCR7 expression; another was negative (or very dim) for CCR7 expression (Top left panel). The mean fluorescence intensities of both populations were increased after treatment with CB-SCs (bottom left panel). FIG. 9*c* demonstrates by flow cytometry CCR7 expression on Naïve CD4$^+$ T cells, CD45RO$^+$CCR7$^+$ T$_{CM}$ and CD45RO$^+$CCR7$^-$ T$_{EM}$ in the gated CD4$^+$ T cells. The data showed the increase of the percentage of Naïve CD4$^+$ T cells and CD4+T$_{CM}$ in the presence of CB-SCs. The percentages of CD4$^+$ T$_{EM}$ were decreased after treatment with CB-SCs FIGS. 10 *a-f* show effects of SCE treatment on β-cell function in Caucasian T1D subjects in the phase 1/2 clinical trial. All subjects received two treatments with SCE device therapy (FIGS. 10 *a-f*). T1D subjects received two treatments with SCE device therapy at the beginning and 3rd month respectively. Fasting (blue) and glucagon-stimulated C-peptide levels (brown) were examined at different time points according to the protocol. For glucagon-stimulated C-peptide production, glucagon (1 mg, i.v.) was administrated within 30 seconds, and six minutes later, plasma samples were collected for the C-peptide test by Ultrasensitive C-peptide ELISA kit. These data were from six T1 D subjects with some residual islet β-cell function (Group A) (FIGS. 10*a-f*). Recovered fasting and glucagon-stimulated C-peptide levels were retained in subjects 1-4 through the final follow-up at 56 weeks post treatment (FIGS. 10*a-d*). FIGS. 10*e-f* show Subjects 5 and 6 displayed some residual islet β-cell function beyond 10 years after diagnosis of T1D. After receiving SCE therapy, fasting C-peptide levels in Subject 5 initially decreased, but increased later at 40 weeks; fasting C-peptide levels in Subject 6 initially declined to 0.09 ng/mL at 26 weeks but improved to 0.21 ng/mL at 40 weeks. Their glucagon-stimulated C-peptide showed the similar tendencies as the fasting C-peptide levels.

FIGS. 12*a-c* show a schematic illustration of the steps for preparation and use of a discontinuous SCE device. FIG. 12*a* illustrates steps for cGMP production of the SCE devicey. FIG. 12*b* depicts steps for ex vivo treatment of a subject's Mononuclear Cells (MNCs) by overnight co-culture with Cord Blood Stem Cells (CB-SCs) in a cGMP processing facility. FIG. 12*c* depicts an overview of the process.

DETAILED DESCRIPTION OF THE INVENTION

Figure 1:
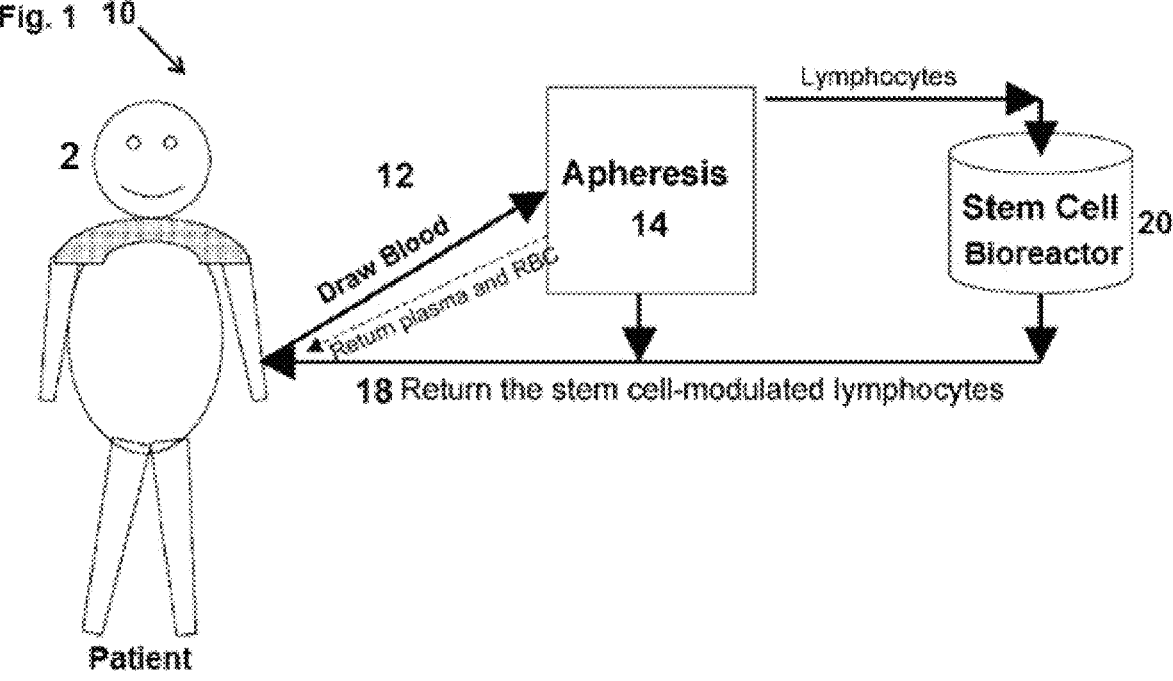
FIG. 1 is a schematic illustration of a method for treating autoimmune disorders according to an embodiment of the described invention.

The terms "alpha cell" or "α-cell" are used interchangeably herein to refer to a type of cell in the pancreas that makes and releases the hormone glucagon when blood glucose level falls too low. Glucagon stimulates the liver to release glucose into the blood for energy.

The terms "A1C, glycated hemoglobin, glycosylated hemoglobin, hemoglobin A1C, HgA1c, and HbA1c" are used interchangeably herein to describe a diagnostic test that measures the percentage of hemoglobin coated with sugar (glycated), which reflects average blood glucose for the past 2 to 3 months. The higher the A1C level, the poorer the blood sugar control and the higher the risk of diabetes complications. Diabetes is diagnosed at an A1C of ≥6.5%.

The term "administer" as used herein means to give or to apply. The term "administering" as used herein includes in vivo administration, as well as administration directly to tissue ex vivo.

The term "adult" or "adult human" refers to a mature organism or a mature cell such as mature human or mature human cell, regardless of age.

The term "allogeneic" as used herein refers to being genetically different although belonging to or obtained from the same species.

The term "ameliorate" as used herein means to make something better or become better, or to improve a disease condition. The disease condition can be an inflammatory condition such as but not limited to type I diabetes or type II diabetes.

As used herein, "analogue" refers to a chemical compound that is structurally similar to another but differs slightly in composition (as in the replacement of one atom by an atom of a different element or in the presence of a particular functional group), but may or may not be derivable from the parent compound. A "derivative" differs from an "analogue" in that a parent compound may be the starting material to generate a "derivative," whereas the parent compound may not necessarily be used as the starting material to generate an "analogue".

The term "anergy" as used herein refers to a lack of reaction by the body's defense mechanisms to foreign substances, and consists of a direct induction of peripheral lymphocyte tolerance.

The term "apheresis" as used herein refers to a medical technology in which the blood of a donor or patient is passed through an apparatus that separates out one particular constituent and returns the remainder back to the donor or patient's circulation.

The term "apply" as used herein refers to placing in contact with or to lay or spread on.

The term "area under the curve (AUC)" as used herein refers to the area under a plot of plasma concentration of a drug against time after drug administration.

The area is determined by the trapazoidal rule: the data points are connected by straight line segments, perpendiculars are erected from the abscissa to each data point, and the sum of the areas of the triangles and trapazoids so constructed is computed. Typically, the area is computed starting at the time the drug is administered and ending when the concentration in plasma is negligible. In practice, the drug concentration is measured at certain discrete points in time and the trapezoidal rule is used to estimate the AUC. The AUC is of use in estimating bioavailability of a drug and in estimating total clearance of a drug.

The term "autocrine signaling" refers to a type of cell signaling in which a cell secretes signal molecules that act on itself or on other adjacent cells of the same type.

The terms "autoimmune disorder" and "autoimmune disease" are used interchangeably to refer to a condition that occurs when the immune system mistakenly attacks and destroys self-components of healthy body tissue. An autoimmune disorder may affect one or more organ or tissue types. Organs and tissue commonly affected by autoimmune disorders include: blood vessels, connective tissues, endocrine glands such as the thyroid or pancreas, joints, muscles, red blood cells, and skin.

The term "Beta cells" or "β-cells" as used herein refers to a pancreatic cell that makes insulin.

The term "blood glucose level" as used herein refers to the amount of glucose in a given amount of blood. It is noted in milligrams in a deciliter, or mg/dL.

The term "blood glucose monitoring" as used herein refers to checking blood glucose level on a regular basis in order to manage diabetes.

The term cell "culture" as used herein refers to providing a cell within a defined boundary space and growth conditions typically compatible with cell growth or for sustaining its viability. Likewise, the term "culture," used as a verb, refers to the process of providing space and growth conditions suitable for growth of the cell or sustaining its viability.

The term "CD3" (TCR complex) as used herein refers to a protein complex composed of four distinct chains. In mammals, the complex contains a CD3γ chain, a CD36 chain, and two CD3E chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

The term "CD4" as used herein refers to a glycoprotein found on the surface of immune cells such as T helper cells, monocytes, macrophages, and dendritic cells. CD4 is a co-receptor that assists the T cell receptor (TCR) in communicating with an antigen-presenting cell. CD4 interacts directly with major histocompatibility complex (MHC) II molecules on the surface of the antigen-presenting cell

[Dalgleish A. G. et al., "The CD4 (T4) antigen is an essential component of the receptor for the AIDS retrovirus", Nature, Vol. 312: 763-768, (1984)].

The term "CD8" as used herein refers to a transmembrane glycoprotein that serves as a co-receptor for the T cell receptor (TCR). Like the TCR, CD8 binds to a major histocompatibility complex (MHC) molecule, but is specific for the class I MHC protein [Leahy D. J. et al., "Crystal structure of a soluble form of the human T cell coreceptor CD8 at 2.6 A resolution", Cell, Vol. 68(6): 1145-62, (1992)].

The term "CD13" as used herein refers to a type II transmembrane protein found on myeloid cells that acts as a zinc-binding metalloprotease catalyzing removal of NH2-terminal amino acids from peptides expressed in some type of acute nonlymphocytic leukemia [Xu W. et al., "Progress in the development of aminopeptidase N (APN/CD13) inhibitors", Curr Med Chem Anticancer Agents., Vol. 5(3): 281-301, (2005)].

The term "CD20" as used herein refers to B-lymphocyte antigen CD20 and is an activated-glycosylated phosphoprotein expressed on the surface of all B-cells beginning at the pro-B phase (CD45R$^+$) and progressively increasing in concentration until maturity [Tedder T. F. et al., "Isolation and structure of a cDNA encoding the B1 (CD20) cell-surface antigen of human B lymphocytes", Proc Natl Acad Sci USA, Vol. 85(1): 208-212, (1998)].

The term "CD25" as used herein refers to a type I transmembrane protein present on activated T cells, activated B cells, some thymocytes, myeloid precursors, and oligodendrocytes that associates with CD122 to form a heterodimer that can act as a high-affinity receptor for IL-2 [Triplett, T. A. et al., European Journal of Immunology, Vol. 42(7): 1893-1898, (2012)].

The term "CD34" as used herein refers to hematopoietic progenitor cell antigen CD34, also known as CD34 antigen, which is a protein that in humans functions as a cell-cell adhesion factor. It may also mediate the attachment of stem cells to bone marrow extracellular matrix or directly to stromal cells [Simmons D. L. et al.," Molecular cloning of a cDNA encoding CD34, a sialomucin of human hematopoietic stem cells", J. Immunol, Vol. 148(1): 267-271, (1992)].

The term "CD38" as used herein refers to a protein marker present on macrophages, dendritic cells, and activated B and NK cells, which may mediate the adhesion between lymphocytes and endothelial cells [Orciani M. et al., "CD38 is constitutively expressed in the nucleus of human hematopoietic cells", J. Cell. Biochem., Vol. 105(3): 905-912, (2008)].

The term "CD45" as used herein refers to a leucocyte common antigen, a type I transmembrane protein present on all hematopoietic cells except erythrocytes that assists in cell activation; expressed in lymphomas, B-cell chronic lymphocytic leukemia, hairy cell leukemia, and acute nonlymphocytic leukemia. It refers to a protein tyrosine phosphatase (PTP) located in all hematopoietic cells, except erythrocytes and platelets [Kaplan R. et al., "Cloning of three human tyrosine phosphatases reveals a multigene family of receptor-linked protein-tyrosine-phosphatases expressed in brain", Proc. Natl. Acad. Sci. U.S.A, Vol. 87(18): 7000-7004, (1990)].

The term "CD59" as used herein refers to a glycosylphosphatidylinositol (GPI)-linked membrane glycoprotein, which protects human cells from complement-mediated lysis [Huang Y. et al., "Defining CD59-C9 binding interaction", J. Biol. Chem., Vol. 281(37): 27398-27404, (2006)].

The term "CD62L (L-selectin)" as used herein refers to a cell marker commonly found on the surface of Naïve T cells [Kohn L. A. et al. "Lymphoid priming in human bone marrow begins before expression of CD10 with upregulation of L-selectin", Nat. Immunol., Vol. 13(10): 963-971, (2012)].

The term "CD69 (Cluster of Differentiation 69)" as used herein refers to a human transmembrane C-Type lectin protein encoded by the CD69 gene. The activation of T lymphocytes and Natural Killer (NK) Cells, both in vivo and in vitro, induces expression of CD69 [Cambiaggi C. et al., "Constitutive expression of CD69 in interspecies T-cell hybrids and locus assignment to human chromosome 12", Immunogenetics, Vol. 36(2): 117-120, (1992)].

The term "CD80" as used herein refers to a protein found on activated B cells and monocytes that provides a costimulatory signal necessary for T cell activation and survival [Zuccarino-Catania G. V. et al., "CD80 and PD-L2 define functionally distinct memory B cell subsets that are independent of antibody isotype", Nat Immunol., Vol. 15(7):631-637, (2012)].

The term "CD86" as used herein refers to a protein expressed on antigen-presenting cells that provides costimulatory signals necessary for T cell activation and survival [Jellis C. L. et al., "Genomic organization of the gene coding for the costimulatory human B-lymphocyte antigen B7-2 (CD86)", Immunogenetics, Vol. 42: 85-89, (1995)].

The term "CD90" (Cluster of Differentiation 90) as us d herein refers to a 25-35 kDa heavily N-glycosylated, glycophosphatidylinositol (GP) anchored conserved cell surface protein with a single V-like immunoglobulin domain, originally discovered as a thymocyte antigen [Wetzel A. et al., "Human Thy-1 (CD90) on activated endothelial cells is a counterreceptor for the leukocyte integrin Mac-1 (CD11b/CD18)", J. Immunol., 172: 3850-3857, (2004)].

The term "CD100" as used herein refers to a protein of the semaphorin family. Semaphorins are a class of secreted and membrane proteins that act as axonal growth cone guidance molecules. They primarily act as short-range inhibitory signals and signal through multimeric receptor complexes [Elhabazi A., "Structure and function of the immune semaphorin CD100/SEMA4D", Crit Rev Immunol., Vol. 23(1-2): 65-81, (2003)].

The term "CD223" as used herein refers to a cell surface molecule with diverse biologic effects on T cell function one of them being an immune checkpoint receptor [Castelli C., "Lymphocyte activation gene-3 (LAG-3, CD 23) in plasmacytoid dendritic cells (pDCs): a molecular target for the restoration of active antitumor immunity", Oncoimmunology, Vol. 3(11): 1-4, (2014)].

The term "chemokine" as used herein refers to a class of chemotactic cytokines that signal leukocytes to move in a specific direction. Chemokines are a family of small cytokines, or signaling proteins secreted by cells. Their name is derived from their ability to induce directed chemotaxis in nearby responsive cells, and as such, they are chemotactic cytokines.

The term "chemokine receptor 7" as used herein refers to a cytokine receptor found on the surface on for example T cells that interact with a type of cytokine called a chemokine. There have been 20 distinct chemokine receptors described in mammals. Each has a 7-transmembrane (7TM) structure and couples to G-protein for signal transduction within a cell, making them members of a large protein family of G protein-coupled receptors [Griffith J. W., "Chemokines and chemokine receptors: positioning cells for host defence and immunity", Annual Review f Immunology, Vol. 32: 659-702, (2014)].

The term "chemotactic" as used herein refers to movement or orientation of a cell along a chemical concentration gradient either toward or away from a chemical stimulus.

The term "chemotaxis" as used herein refers to the directed motion of a motile cell or part towards environmental conditions it deems attractive and/or away from surroundings it finds repellent.

The term "colony stimulating factor" as used herein refers to a cytokine responsible for controlling the production of white blood cells. Types include granulocyte colony stimulating factor (G-CSF), macrophage colony stimulating factor (M-CSF), and granulocyte macrophage colony stimulating factor (GM-CSF).

The term "compatible" as used herein means that components of a composition are capable of being combined with each other in a manner such that there is no interaction that would substantially reduce the efficacy of th composition under ordinary use conditions.

The term "component" as used herein refers to a constituent part, element or ingredient.

The term "condition" as used herein, refers to a variety of health states and is meant to include disorders or diseases caused by any underlying mechanism, disorder, or injury The term "consequence" as used herein refers to an effect, result or outcome of something that occurred earlier.

The term "contact" and all its grammatical forms as used herein refers to a state or condition of touching or of being in immediate or local proximity.

The term "connecting peptide" or "C-peptide" as used herein refers to a short 31-amino-acid polypeptide that connects insulin's A-chain to its B-chain in the proinsulin molecule. It is used as a marker in autoimmune diseases like diabetes. Increased levels are an indication for insulin release as they are released at equimolar quantities and a better outcome for a patient. A very low C-peptide confirm type 1 diabetes and insulin dependence and is associated with high glucose variability, lack of glucose homeostasis and increased complications with poor outcome. Measurement of C-peptide levels is clinically validated by assessment of proper β-cell function [Wahren J. et al., "The clinical potential of C-peptide in replacement in type 1 diabetes", Diabetes, Vol. 61(4), 761-772, (2012)].

The terms "cord blood-derived stem cells (CB-SCs)" and "cord blood mononuclear cells" are used interchangeably with the term "cord blood mononuclear stem cell" and with the term "umbilical cord stem cells (UC-SCs)."

The term "culture medium" as used herein refers generally to any preparation used for the cultivation of living cells. A "cell culture" refers to cells cultivated in vitro.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNF and lymphotoxin; immuoglobulin superfamily members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and rigger cascades of other cytokines. Nonlimiting examples of cytokines include e.g., IL-1.alpha., IL-beta., IL-2, IL-3, IL-4, IL-5, IL-6, IL-7, IL-8, IL-9, IL-10, IL-11, IL-12/IL-23 P40, IL13, IL-17, IL-18, TGF-beta., IFN-gamma, GM-CSF, Gro-alpha., MCP-1 and TNF-alpha.

The term "cytometry" as used herein refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and collect cells (or other small particles) with measured characteristics that fall within a user-selected range of values.

The term "differentiation" as used herein refers to the process by which a cell or cells change to a different and phenotypically distinct cell type. The term "differentiation inducer" as used herein refers to a compound that is a direct, or indirect, causative agent of the process of cell differentiation. A "differentiation inducer" while sufficient to cause differentiation is not essential to differentiation.

The term "disease" or "disorder" as used herein refers to an impairment of health or a condition of abnormal functioning.

The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, E-Cy5 Tandem, propidium iodem, EGFP, EYGP, ECF, DsRed, allophycocyanin (PC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy$^7$, Hoechst 33342, DAPI, Hoechst 33258, SYTOX Blue, chromomycin A3, mithramycin, YOYO-1, S TOX Orange, ethidium bromide, 7-AAD, acridine orange, TOTO-1, TO-PRO-1, hiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyanl, Y77W, S65A, S65C, S65L, S65T, ZsGreenl, ZsYellowl, DsRed2, DsRed monomer, AsRed2, mRFP1, HcRedl, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, GFP [Prendergast F. G. et al, "Chemical and physical properties of aequorin and the green fluorescent protein isolated from Aequorea forskalea". Biochemistry, Vol. 17(17): 3448-53, (1978)], and derivatives thereof.

The term "educated" as used herein refers to a result of co-culturing patient mononuclear cells and UC-SCs under conditions so that the two cell populations can interact, meaning to have a reciprocal effect or influence on each other.

The term "enrich" as used herein refers to increasing the proportion of a desired substance, for example, to increase the relative frequency of a subtype of cell compared to its natural frequency in a cell population.

The term "flow cytometry" as used herein refers to a tool for interrogating the phenotype and characteristics of cells. It senses cells or particles as they move in a liquid stream through a laser (light amplification by stimulated emission of radiation)/light beam past a sensing area. The relative light-scattering and color-discriminated fluorescence of the microscopic particles is measured. Analysis and differentiation of the cells is based on size, granularity, and whether the cells is carrying fluorescent molecules in the form of either antibodies or dyes. As the cell passes through the laser beam, light is scattered in all directions, and the light scattered in the forward direction at low angles (0.5-10°) from the axis is proportional to the square of the radius of a sphere and so to the size of the cell or particle. Light may enter t e cell; thus, the 90° light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population [Marion G. Macey, Flow cytometry: principles and applications, Humana Press, 2007].

The term "FOXP3 (forkhead box P3; or scurfin) as used herein refers to a protein involved in immune system responses. A member of the FOX protein family, FOXP3 functions as a transcription factor regulator in the development and function of regulatory T cells. Regulatory T cells generally turn down the immune response thereby has a role in controlling autoreactive T cells [Kornete M. et al., "Th1-Like ICOS+ Foxp3+ Treg Cells Preferentially Express CXCR3 and Home to β-Islets during Pre-Diabetes in BDC2.5 NOD Mice", PLoS One., Vol. 10(5): 1-16, (2015)].

The term "fresh" as used herein refers to a biological material that is collected within at least 1 hour from a patient, or stored at 4° C., but the biological material is not frozen and thawed. The biological material can be the following but without limitation, leukocytes, mononuclear cells or stem cells isolated from peripheral blood, cord blood, buffy coat, bone marrow etc.

The term "graft" as used herein, refers to any tissue or organ for transplantation. It includes, but is not limited to, a self-tissue transferred from one body site to another in the same individual ("autologous graft"), a tissue transferred between genetically identical individuals or sufficiently immunologically compatible to allow tissue transplant ("syngeneic graft"), a tissue transferred between genetically different members of the same species ("allogeneic graft" or "allograft"), and a tissue transferred between different species ("xenograft").

The term "growth" as used herein refers to the expansion of a cell population and/or cell size. The term "growth factor" as used herein refers to a substance that induces, or modifies the rate or extent of cell growth.

The term "hematopoietic stem cell" as used herein refers to a cell isolated from the blood or from the bone marrow that can renew itself, differentiate to a variety of specialized cells that mobilize out of the bone marrow into the circulating blood, and can undergo programmed cell death (apoptosis). According to some embodiments of the described invention, hematopoietic stem cells derived from human subjects express at least one type of cell surface marker, including, but not limited to, CDS34, CD38, HLA-DR, c-kit, CD59, Sca-1, Thy-1, and/or CXCR-4, or a combination thereof.

The term "HLA-DR" as used herein refers to a human class II histocompatibility antigen present on several cell types, including antigen-presenting cells, B cells, monocytes, macrophages, and activated T cells.

The term "hormone" as used herein refers to a chemical produced in one part of the body and released into the blood to trigger or regulate particular functions of the body.

The term "immune disorder-related disease" as used herein refers to a disease in which a derangement of the immune system contributes to the pathogenesis of disease.

The terms "Immune tolerance" or "immunological tolerance" as used herein refer to a state of unresponsiveness of the immune system to substances that normally have the capacity to elicit an immune response.

The term "immunomodulatory cell(s)" as used herein refer(s) to cell(s) that are capable of augmenting or diminishing immune responses by expressing chemokines, cytokines and other mediators of immune responses.

The term "impaired glucose tolerance (IGT)" as used herein refers to a condition in which blood glucose levels are higher than normal but are not high enough for a diagnosis of diabetes. IGT, also called pre-diabetes, is a level of 140 mg/dL to 199 mg/dL 2 hours after the start of an oral glucose tolerance test (OGTT). Most individuals with pre-diabetes are at increased risk for developing type 2 diabetes.

The term "inflammatory cytokines" or "inflammatory mediators" as used herein refers to molecular mediators of the inflammatory process, which may modulate being either pro- or anti-inflammatory in their effect. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, pro-inflammatory cytokines, including, but not limited to, interleukin-1-beta (IL-1P), interleukin-4 (IL-4), interleukin-6 (IL-6), interleukin-8 (IL-8), tumor necrosis factor-alpha (TNF-$\alpha$), interferon-gamma (IF-$\gamma$), and interleukin-12 (IL-12).

The term "infuse" and its other grammatical forms as used herein refers to the introduction of a fluid other than blood into a blood vessel of a subject, including humans, for therapeutic purposes.

The term "infusion solution" as used herein refers to a solution containing phosphate buffered saline (PBS) supplemented with 25 USP units/mL of heparin and 1% human serum albumin (HSA) and that is serum-free.

The term "inflammation" as used herein refers to a physiologic response to infection and injury in which cells involved in detoxification and repair are mobilized to the compromised site by inflammatory mediators. The term "acute inflammation" as used herein, refers to inflammation, usually of sudden onset, characterized by the classical signs, with predominance of the vascular and exudative processes. The term "chronic inflammation" as used herein refers to inflammation of slow progress and marked chiefly by the formation of new connective tissue. It may be a continuation of an acute form or a prolonged low-grade form, and usually causes permanent tissue damage.

Regardless of the initiating agent, the physiologic changes accompanying acute inflammation encompass four main features: (1) vasodilation, which results in a net increase in blood flow, is one of the earliest physical responses to acute tissue injury; (2) in response to inflammatory stimuli, endothelial cells lining the venules contract, widening the intracellular junctions to produce gaps, leading to increased vascular permeability which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The terms "inflammatory" or "immuno-inflammatory" as used herein with respect to mediators refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, pro-inflammatory cytokines, including, but not limited to, interleukin-1, interleukin-4, interleukin-6, interleukin-8, tumor necrosis factor (TNF), interferon-gamma, and interleukin 12.

The term "inhibit" and its various grammatical forms, including, but not limited to, "inhibiting" or "inhibition", as used herein refers to reducing the amount or rate of a process, to stopping the process entirely, or to decreasing, limiting, or blocking the action or function thereof. Inhibition can include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a second molecule that binds to a first molecule thereby decreasing the first molecule's activity. Inhibitors often are evaluated by their specificity and potency.

The term "insulin resistance" as used herein refers to a condition in which the body's normal response to a given amount of insulin is reduced. s a result, higher levels of insulin are needed for it to have its proper effects. The pancreas produces more and more insulin until it no longer can produce sufficient insulin for the body's demands. Blood sugar then rises. Insulin resistance is a risk factor for development of type 2 diabetes.

The term "interleukin" as used herein refers to a cytokine secreted by white blood cells as a means of communication with other white blood cells. Interleukins regulate cell growth, differentiation, and motility, and stimulates immune responses, such as inflammation. Examples of interleukins include without limitation interleukin-1 (IL-1), interleukin-1β (IL-1β), interleukin-6 (IL-6), interleukin-8 (IL-8), and interleukin-12 (IL-12).

The term "isolated" as used herein refers to a material, such a, but not limited to, a cell or cell population, which is substantially or essentially free from components that normally accompany or interact with it as found in its naturally occurring environment.

The term "leukocyte" or "white blood cell (WBC)" as used herein refers to a type of immune cell. Most leukocytes are made in the bone marrow and are found in the blood and lymph tissue. Leukocytes help the body fight infections and other diseases. Granulocytes, monocytes, and lymphocytes are leukocytes.

The term "lymphocytes" as used herein refers to a small white blood cell (leukocyte) that plays a large role in defending the body against disease. There are two main types of lymphocytes: B cells and T cells. The B cells make antibodies that attack bacteria and toxins while the T cells attack body cells themselves. Lymphocytes secrete products (lymphokines) that modulate the functional activities of many other types of cells and are often present at sites of chronic inflammation.

The term "macrophage" as used herein refers to a mononuclear, actively phagocytic cell arising from monocytic stem cells in the bone marrow. These cells are widely distributed in the body and vary in morphology and motility. Phagocytic activity is typically mediated by serum recognition factors, including certain immunoglobulins and components of the complement system, but also may be non-specific. Macrophages also are involved in both the production of antibodies and in cell-mediated immune responses, particularly in presenting antigens to lymphocytes. They secrete a variety of immuno-regulatory molecules.

The term "major histocompatibility complex (MHC)" as used herein refers to a set of genes that encodes cell surface molecules which control an essential part of the immune system in all vertebrates by determining histocompatibility. The main function of MHC molecules is to bind to peptide fragments derived from pathogens and display them on the cell surface for recognition by the appropriate T-cells.

The term "mimetic" as used herein refers to a compound containing chemical moieties that mimic the activity of a peptide. For example, if a peptide contains two charged chemical moieties having functional activity, a mimetic places two charged chemical moeities in a spatial orientation and constrained structure so that the charged chemical function is maintained in three-dimensional space. Mimetics may themselves be peptides. Mimetics may also be non-peptides and/or may comprise amino acids linked by non-peptide bonds, e.g., without limitation, psi bonds [Benkirane, N., et al. J. Biol. Chem., Vol. 271: 33218-33224, (1996)], U.S. Pat. No. 5,637,677 and its parent applications contain detailed guidance on the production of mimetics.

The term "mitogenic compound" as used herein refers to a compound capable of affecting the rate of cell division for at least one cell type under at least one set of conditions suitable for growth or culture.

The term "modulate" as used herein means to regulate, alter, adapt, or adjust to a certain measure or proportion.

The term "multipotent" as used herein, refers to a cell that can develop into more than one cell type, but that is more limited than a pluripotent cell. Adult stem cells and umbilical cord blood stem cells are considered multipotent.

The term "negative selection" as used herein refers to depletion or removal all cell types except for a cell type of interest, which remains.

The term "oral glucose tolerance test (OGTT)" as used herein refers to a test to diagnose pre-diabetes and diabetes given by a health care professional after an overnight fast. A blood sample is taken, then the patient drinks a high-glucose beverage. Blood samples are taken at intervals for 2 to 3 hours. Test results are compared with a standard and show how the body uses glucose over time. Diabetes is diagnosed when a two-hour blood glucose is greater than or equal to 200 mg/dL.

The term "paracrine signaling" as used herein refers to short-range cell-cell communication via secreted signal molecules that act on adjacent cells.

The term "pre-diabetes" as used herein refers to a condition in which blood glucose levels are higher than normal but are not high enough for a diagnosis of diabetes. People with pre-diabetes are at increased risk for developing Type 2 diabetes and for heart disease and stroke. Results indicating prediabetes include: an A1C of 5.7%-6.4%. Fasting blood glucose of 100 mg/dL-125 mg/dL, and an oral glucose tolerance test (OGTT) 2 hour blood glucose of 140 mg/dL-199 mg/dL.

The term "pluripotent" refers to a cell that can give rise to all the cell types that make up the body. For example, embryonic stem cells are considered pluripotent. Induced pluripotent stem cells (iPSCs) are adult cells that have been genetically reprogrammed to an embryonic stem cell-like state by being forced to express genes and factors important for maintaining the defining properties of embryonic stem cells. Pluripotent markers include, without limitation, Oct-4, Nanog, and Sox-2.

The term "positive selection" as used herein refers to the isolation of a target cell population.

The term "progenitor cell" as used herein refers to an early descendant of a stem cell that can only differentiate, but can no longer mature itself. Progenitor cells mature into precursor cells that mature into mature phenotypes. Progenitor cells are referred to as colony-forming units (CFU) or colony-forming cells (CFC). The specific lineage of a progenitor cell is indicated by a suffix, such as, but not limited to, CFU-E (erythrocytic), CFU-F (fibroblastic), CFU-GM (granulocytic/macrophage), and CFU-GEMM (pluripotent hematopoietic progenitor.

The term "proliferate" and its various grammatical form as used herein refers to an increase in number. The terms "proliferate" and "expand" are used interchangeably herein.

The term "propagate" or "propagation" refers to causing to reproduce, to increase in number or amount.

The term "purify" as used herein refers to freeing from foreign or extraneous elements.

The term "reduced" or "to reduce" as used herein refers to a diminution, a decrease, an attenuation or abatement of the degree, intensity, extent, size, amount, density or number.

The term "regulatory T cells (Tregs)", formerly known as suppressor T cells, as used herein refers to a subpopulation of T cells which modulate the immune system to maintain tolerance to self-antigens and abrogate autoimmune disease.

The term "repair" as used herein as a noun refers to an correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch, or to otherwise restore function.

The term "stem cell" as used herein refers to undifferentiated cells having high proliferative potential with the ability to self-renew that can generate daughter cells that can undergo terminal differentiation into more than one distinct cell phenotype.

The terms "subject" or "individual" or "patient" are used interchangeably to refer to a member of an animal species of mammalian origin, including, without limitation, humans, nonhuman primates; farm animals such as cattle, sheep, pigs, goats and horses; domestic mammals such as dogs and cats; laboratory animals including rodents such as mice, rats and guinea pigs, and the like.

The term "subject in need of such treatment" as used herein refers to a patient who (i) will suffer from an disorder with an autoimmune component (ii) is suffering from a disorder with an autoimmune component; or (iii) has suffered from a disease with an autoimmune component. According to some embodiments, the phrase also is used to refer to a patient who (i) will receive the described stem cell educator (SCE) treatment; (b) is receiving the described SCE treatment; or (c) has received the described SCE treatment, unless the context and usage of the phrase indicates otherwise.

The terms "substantial", "substantially", "essential" or "essentially" as used herein indicate that the feature which is described by these terms is present in an amount or has an impact which provides for a technical effect with relevance for the exercise of the presently claimed invention. For instance, a "substantial amount" of a substance in a composition is an amount which provides for a technical effect attributable to the substance. Likewise, if a composition is indicated as comprising "substantially no" of a particular substance, this means that the composition is allowed to include insignificant amounts of the substance, as long as these amounts do not have any technical impact on the other ingredients in the composition end does not in itself "make a difference" or put in other words, "substantially no" and "essentially no" means that e.g. trace amounts or effects may be present as long as they do not have an overall technical influence. The terms, "essentially free" or "substantially free" as used herein refer to being considerably or significantly free of a contaminating substance, impurity or material, e.g., the contaminating substance, impurity or material is present in an amount less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% as determined by an analytical protocol.

As used herein, the term "substantially homogeneous" when applied to cells, refers to a population of cells, wherein at least about 70% of the cells in the population are of the same cell type as determined by an assay for one or m re markers of differentiation.

The term "suppress" as used herein means to inhibit, mask or abolish a biological event.

The term "surface antigen" means a substance that is typically localized to an external surface of a cell, such as by association with a cell membrane. A cell "marker," is a detectable element sufficiently associated with a cell, so as to be characteristic of that cell or cell type. A cell-surface marker, for example, can be detected with minimal disruption of cellular activity, and can facilitate the characterization of a cell type, its identification, and eventually its isolation. Cell sorting techniques are based on cellular biomarkers where a cell surface marker may be used for either positive selection or negative selection, i.e., for inclusion or exclusion, from a cell population.

The term "T cell compartment" as used herein refers to a cooperative assembly of T lymphocytes embedded in a complex network of secreted extracellular macromolecules within which cells of the compartment can migrate and interact with one another. Exemplary members of the T-cell compartment include a naïve T cell population, an antigen-experienced T cell population, regulatory T cell population (Tregs), a helper T cell population, a cytotoxic T cell population, a memory T cell population ($T_{CM}$), an effector T cell population ($T_{EM}$).

The terms "therapeutic amount", "therapeutically effective amount", an "amount effective", "effective amount", or "pharmaceutically effective amount" are used interchangeably to refer to an amount that is sufficient to provide the intended benefit of treatment. However, exposure levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutically effective amounts" and "pharmaceutically effective amounts" include prophylactic or preventative amounts. In prophylactic or preventative applications of the described invention, the SCE device and treatment are used to treat a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "therapeutic window" refers to a concentration range that provides therapeutic efficacy without unacceptable toxicity. Following administration of a dose of a drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations with in the therapeutic window for the desired response with a minimum of toxicity. Drug response below the MEC for the desired effect will be sub-therapeutic, whereas for a adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

Instead, another dose of drug should be given to maintain concentrations within the therapeutic window. In general, the lower limit of the therapeutic range of a drug appears to be approximately equal to the drug concentration that produces about half of the greatest possible therapeutic effect, and the upper limit of the therapeutic range is such that no more than about 5% to about 10% of patients will experience a toxic effect. These figures can be highly variable, and some patients may benefit greatly from drug concentrations that exceed the therapeutic range, while others may suffer significant toxicity at much lower values. The therapeutic goal is to maintain steady-state drug levels within the therapeutic window. For most drugs, the actual concentrations associated with this desired range are not and need not be known, and it is sufficient to understand that efficacy and toxicity are generally concentration-dependent, and how drug dosage and frequency of administration affect the drug level.

For a small number of drugs where there is a small (two- to three-fold) difference between concentrations resulting in efficacy and toxicity, a plasma-concentration range associated with effective therapy has been defined.

In this case, a target level strategy is reasonable, wherein a desired target steady-state concentration of the drug (usually in plasma) associated with efficacy and minimal toxicity is chosen, and a dosage is computed that is expected to achieve this value. Drug concentrations subsequently are measured and dosage is adjusted if necessary to approximate the target more closely.

In most clinical situations, drugs are administered in a series of repetitive doses or as a continuous infusion to maintain a steady-state concentration of drug associated with the therapeutic window. To maintain the chosen steady-state or target concentration ("maintenance dose"), the rate of drug administration is adjusted such that the rate of input equals the rate of loss. If the clinician chooses the desired concentration of drug in plasma and knows the clearance and bioavailability for that drug in a particular patient, the appropriate dose and dosing interval can be calculated.

As used herein, the term "totipotent cell" refers to a cell that has the potential to give rise to any and all cell types in a body plus the extraembryonic, or placental, cells. Embryonic cells within the first couple of cell divisions after fertilization are totipotent cells.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "Type 1 diabetes" as used herein refers to a condition characterized by high blood glucose levels caused by a total lack of insulin that occurs when the body's immune system attacks the insulin-producing beta cells in the pancreas and destroys them. The pancreas then produces little or no insulin. Type 1 diabetes develops most often in young people but can appear in adults.

The term "Type 2 diabetes" as used herein refers to a condition characterized by high blood glucose levels caused by either a lack of insulin or the body's inability to use insulin efficiently. Type 2 diabetes develops most often in middle-aged and older adults but can appear in young people.

The term "umbilical cord (UC) mononuclear cell (MNC)", "(UC-MNC)", as used herein refers to cells of hematopoietic lineage, such as lymphocytes, monocytes, stem and progenitor cells, and mesenchymal stromal cells derived from umbilical cord blood (CB).

The term "undifferentiated" as used herein refers to a cell that has not developed a characteristic of a more specialized cell. A cell that is "differentiated" is one that has a characteristic of a more specialized cell. The terms "undifferentiated" and "differentiated" are relative with respect to each other. Differentiated and undifferentiated cells are distinguished from each other by, for example, morphological characteristics such as relative size and shape, ratio of nuclear volume to cytoplasmic volume; and expression characteristics such as detectable presence of known markers of differentiation. Exemplary markers of differentiation include a protein, a carbohydrate, a lipid, a nucleic acid, a functional characteristic and a morphological characteristic.

Method for Treating a Disease Characterized by Lymphocyte Autoreactivity

According to one aspect, the described invention provides a method for treating a disease characterized by lymphocyte autoreactivity, comprising:

(1) acquiring under sterile conditions a whole blood sample containing mononuclear cells from a subject diseased with the disease characterized by lymphocyte autoreactivity;

(2) transporting the whole blood sample of (1) to a processing facility;

(3) sterilely purifying the mononuclear cells (MNC) from the whole blood sample to form a mononuclear cell preparation;

(4) introducing the mononuclear cell preparation into a bioreactor device comprising a viable population of adherent umbilical cord blood stem cells (UC-SCs), wherein the adherent UC-SCs are at least 80% confluent;

(5) co-culturing the mononuclear cell preparation with the CB-SCs so that the mononuclear cells in the mononuclear cell preparation and the CB-SCs can interact for at least 0.1 hour, at least 0.2 hour, at least 0.3 hour, at least 0.4 hour, at least 0.5 hour, at least 0.6 hour, at least 0.7 hour, at least 0.8 hour, at least 0.9 hour, at least 1.0 hour, at least 1.5 hours, at least 2 hours, at least 2.5 hours, at least 3 hours, at least 3.5 hours, at least 4 hours, at least 4.5 hours, at least 5 hours, at east 5.5 hours, at least 6 hours, at least 6.5 hours, at least 7 hours, at least 7.5 hours, or at least 8 hours under sterile conditions to form an educated mononuclear cell product;

(6) harvesting the educated mononuclear cell product under sterile conditions from the bioreactor device;

(7) Confirming purity, sterility, and percent viability of the educated mononuclear cell product having at least $10^4$ at least $10^5$, at least $10^6$, at least $10^7$, or at least $10^8$ mononuclear cells;

(8) transporting the educated mononuclear cell product to a clinical facility for intravascular infusion into the subject; and (9) infusing a therapeutically effective amount of the educated mononuclear cell product intravascularly into the subject;

(10) repeating steps (1) through (9) in order, at a plurality of infusion dates as needed over a subject's lifetime, wherein the therapeutically effective amount of the educated mononuclear cell product is effective to modulate autoreactivity in a T cell compartment of the subject, and to reduce symptoms of the immune disease.

According to some embodiments the disease characterized by lymphocyte autoreactivity is selected from the group consisting of Type 1 diabetes (T1D) or Type 2 diabetes (T2D). According to some embodiments, the disease characterized by lymphocyte autoreactivity is diabetes. According to some embodiments, the disease characterized by lymphocyte autoreactivity is type 1 diabetes. According to some embodiments, the disease characterized by lymphocyte autoreactivity is type 2 diabetes.

According to some embodiments, the mononuclear cell population comprises a population of immunomodulatory cells. According to some embodiments, the population of immunomodulatory cells comprises a population of leukocytes. According to some embodiments, the population of leukocytes comprises a population of lymphocytes, a population of granulocytes, a population of basophils, a population of monocytes, or a combination thereof. According to some embodiments, the population of immunomodulatory cells comprises a population of antigen-capturing cells, a population of antigen presenting cells, or both. According to some embodiments, the population of antigen presenting cells expresses CD80, CD86, or both. According to some embodiments, the population of antigen presenting cells comprises macrophages, dendritic cells or both. According to some embodiments, the population of lymphocytes comprises a population of T lymphocytes, a population of B lymphocytes, a population of natural killer (NK) cells, or a combination thereof.

According to some embodiments, the population of T lymphocytes comprises one or more populations of T cells. According to some embodiments, the population of T cells comprise activated T cells. According to some embodiments, the population of activated T cells is selected from the group consisting of naive T cells, primed T-cells, activated T cells, effector T cells, cytotoxic T cells, T helper cells, memory T cells, NK cells, and Treg cells. According to some embodiments the population of T cells comprises T cells expressing one or more inflammatory mediators (lymphokines).

According to some embodiments, the inflammatory mediators are selected from the group consisting of interleukin-1-beta (IL-1P), IL-2, interleukin-4 (IL-4), IL-5, interleukin-6 (IL-6), interleukin-8 (II-8), IL-10, tumor necrosis factor-alpha (TNF-$\alpha$), interferon-gamma (IFN-$\gamma$), interleukin-12 (IL-12), and Lymphotoxin. According to some embodiments the population of T lymphocytes comprises T cells expressing one or more markers selected from the group consisting of T cell receptor (TCR)/CD3, CD4, CD8, CD25, CD28, CD40 ligand (CD40L), Fox3, fas, MHC I, MHCII, immunoreceptor tyrosine-based activation motif (ITAM), ZAP70 (zeta associated protein.

According to some embodiments, the population of B lymphocytes comprises one or more populations of B cells. According to some embodiments, the population of B cells comprise activated B cells. According to some embodiments, the population of B cells is selected from the group consisting of naive B cells, activated B cells, plasmaplasts, and memory B cells. According to some embodiments the population of B lymphocytes comprises B cells expressing one or more marker selected from the group consisting of MHC class II, CD40, an immunoglobulin.

Methods for purifying mononuclear cells from whole blood samples are well known. According to one embodiment, red blood cells are removed by density gradient centrifugation, e.g., using Ficoll Paque fractionation, to separate the buffy coat from red blood cells. The term "buffy coat" refers to a thin grayish white fraction of a blood sample that contains most of the leukocytes.

According to some embodiments, purification of mononuclear cells from the whole blood sample is by apheresis using an automated apheresis separator. In brief, whole blood is taken from the patient and then passed through an apparatus containing a spinning chamber. The blood separates into its components (plasma, platelet-rich plasma, leukocytes and red blood cells) by gravity along the wall of the chamber. Mononuclear cells are sorted out and the remaining blood components are re-introduced back into the bloodstream of the patient.

According to some embodiments, magnetic bead activated cell sorting is a positive selection technique used for purifying a specific cell population from peripheral blood mononuclear cells. Because the quantity and activity of the desired cells may decrease after such protocols, some prefer gentler substrate adhesion and negative selection protocols.

According to some embodiments, the bioreactor device comprises one or more surfaces comprising a viable population of adherent umbilical cord blood stem cells (UC-SC's). The method for preparing the bioreactor comprising the UC-SCs by a process comprising, in order:

(a) obtaining a fresh cord blood unit obtained from healthy donors;

(b) isolating a mononuclear cell fraction from the umbilical cord blood by density gradient centrifugation;

(c) removing red blood cells;

(d) washing the UC-mononuclear cells with a physiological buffered saline solution;

(e) seeding the UC mononuclear cells in the bioreactor in a serum-free culture medium at a seeding density of at least $1\times10^6$ cells;

(f) culturing the UC mononuclear cells in a serum-free culture medium, changing half/the medium every 2-3 days to remove nonadherent cells, and for at least 10 days to grow to at least 80% confluence; and (g) confirming sterility and viability of a sample of the CB-SC cultures.

The cultures of CB-SCs are round and are attached in the bottom surface of the bioreactor device. According to some embodiments, the surface of the bioreactor device is an uncoated plastic. According to some embodiments the surface of the bioreactor device is a positively charged surface. According to some embodiments, the surface of the bioreactor device is a hydrophobic surface, for example, polystyrene or glass. According to some embodiments, the surface of the bioreactor device is coated According to some embodiments, the surface of the bioreactor device does not comprise a cell feeder layer.

According to some embodiments, the umbilical cord blood mononuclear cells are grown to at least 80% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing.

According to some embodiments of the invention, the umbilical cord blood mononuclear cells are grown to at least 85% confluence for at least 10 days, at least 11 days, at least 12 days, at least 13 days, at least 14 days, at least 5 days, at least 16 days, at least 17 days, at least 18 days, at least 19 days, at least 20 days or at least 21 days prior to co-culturing. According to some embodiments of the invention, the umbilical cord blood mononuclear cells are grown to at least 90% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 95% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 96% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing According to some embodiments of the invention, the umbilical cord blood mononuclear cells are grown to at least 97% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 99% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 99% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing.

The mononuclear cell preparation from the patient is introduced into the bioreactor for co-cultivating the patient's mononuclear cells and the UC-SC cells. According to some embodiments, the mononuclear preparation is separated from the UC-SC layer. According to some embodiments, the patient's mononuclear cells are nonadherent. According to some embodiments the patient's mononuclear cells contact the cells in the UC-SC layer. According to some embodiments the culture medium comprises growth factors, soluble inflammatory mediators, and the like. According to some embodiments, the culture medium is effective to support both the patient's mononuclear cells and the UC-SC cell layer. According to some embodiments, the culture medium comprises immunomodulatory mediators and soluble factors produced by the patient's mononuclear cells and by the UC-SC cells.

According to some embodiments the interacting conditions comprise gentle rocking of the bioreactor. According to some embodiments, the gentle rocking of the bioreactor is intermittent. According to some embodiments, the medium is circulated through the bioreactor.

The patient's mononuclear preparation and the CB-SCs are co-cultivated under interacting conditions for at least 2 hours under sterile conditions. The patient's mononuclear preparation and the CB-SCs are co-cultivated under interacting conditions for at least 3 hours under sterile conditions. The patient's mononuclear preparation and the CB-SCs are co-cultivated under interacting conditions for at least 4 hours under sterile conditions. The patient's mononuclear preparation and the CB-SCs are co-cultivated under interacting conditions for at least 5 hours under sterile conditions. The patient's mononuclear preparation and the CB-SCs are co-cultivated under interacting conditions for at least 6 hours under sterile conditions. The patient's mononuclear preparation and the CB-SCs are co-cultivated under interacting conditions for at least 7 hours under sterile conditions. The patient's mononuclear preparation and the CB-SCs are co-cultivated under interacting conditions for at least 8 hours tinder sterile conditions. The patient's mononuclear preparation and the CB-SCs are co-cultivated under interacting conditions for at least 9 hours under sterile conditions. The patient's mononuclear preparation and the CB-SCs are co-cultivated under interacting conditions for at least 10 hours under sterile conditions. The patient's mononuclear preparation and the CB-SCs are co-cultivated under interacting conditions for at least 11 hours under sterile conditions. The patient's mononuclear preparation and the CB-SCs are co-cultivated under interacting conditions for at least 12 hours under sterile conditions.

The patient's mononuclear preparation and the CB-SCs are co-cultivated under interacting conditions for at least 13 hours under sterile conditions. The patient's mononuclear preparation and the CB-SCs are co-cultivated under interacting conditions for at least 14 hours under sterile conditions. The patient's mononuclear preparation and the CB-SCs are co-cultivated under interacting conditions for at least 15 hours under sterile conditions. The patient's mononuclear preparation and the CB-SCs are co-cultivated under interacting conditions for at least 16 hours under sterile conditions.

The patient's mononuclear preparation and the CB-SCs are co-cultivated under interacting conditions for at least 17 hours under sterile conditions. The patient's mononuclear preparation and the CB-SCs are co-cultivated under interacting conditions for at least 18 hours under sterile conditions. The patient's mononuclear preparation and the CB-SCs are co-cultivated under interacting conditions for at least 19 hours under sterile conditions. The patient's mononuclear preparation and the CB-SCs are co-cultivated under interacting conditions for at least 20 hours under sterile conditions.

The patient's mononuclear preparation and the CB-SCs are co-cultivated under interacting conditions for at least 21 hours under sterile conditions. The patient's mononuclear preparation and the CB-SCs are co-cultivated under interacting conditions for at least 22 hours under sterile conditions. The patient's mononuclear preparation and the CB-SCs are co-cultivated under interacting conditions for at least 23 hours under sterile conditions. The patient's mononuclear preparation and the CB-SCs are co-cultivated under interacting conditions for at least 24 hours under sterile conditions.

According to some embodiments, the umbilical cord blood mononuclear stem cells and patient mononuclear cells are co-cultivated at a ratio of at least 1:2. According to some embodiments, the umbilical cord blood mononuclear stem cells and patient mononuclear cells are co-cultivated at a ratio of at least 1:5. According to some embodiments, the umbilical cord blood mononuclear stem cells a d patient mononuclear cells are co-cultivated at a ratio of at least 1:10. According to some embodiments, the umbilical cord blood mononuclear stem cells and patient mononuclear cells are co-cultivated at a ratio of at least 1:20. According to some embodiments, the umbilical cord blood mononuclear stem cells and patient mononuclear cells are co-cultivated at a ratio of at least 1:50. According to some embodiments, the umbilical cord blood mononuclear stem cells and patient mononuclear cells are co-cultivated at a ratio of at least 1:60. According to some embodiments, the umbilical cord blood mononuclear stem cells and patient mononuclear cells are co-cultivated at a ratio of at least 1:70. According to some embodiments, the umbilical cord blood mononuclear stem cells and patient mononuclear cells are co-cultivated at a ratio of at least 1:80. According to some embodiments, the umbilical cord blood mononuclear stem cells and patient mononuclear cells are co-cultivated at a ratio of at least 1:90. According to some embodiments, the umbilical cord blood mononuclear stem cells and patient mononuclear cells are co-cultivated at a ratio of at least 1:100.

The result of this interaction is an educated mononuclear cell product.

The educated mononuclear cell product is harvested under sterile conditions from the bioreactor device.

Assays for confirming purity, sterility, and viability of the educated mononuclear cell product; percent viability include the following.

According to some embodiments, endotoxin levels of the educated mononuclear cell product are less than about 0.5 endotoxin units mL, and the educated mononuclear cell product is Gram stain negative. The educated mononuclear cell product is also tested for *Mycoplasma* and sterility, e.g., by real-time PCR in compliance with the requirements of US FDA Good Laboratory Practice Regulations.

A "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection rea ent may comprise a marker.

Markers can be assayed by any of various established methods. Antibody-based techniques include, without limitation, fluorescence activated cell sorting (FACS) immuno-fluorescence, enzyme immunohistochemistry, and immuno-blotting. Further assays may include assays for detection of cytokine levels or mRNAs or "Western blot" techniques detecting the encoding of a particular marker. The term, "Western blot" refers to a method for identifying proteins in a complex mixture; proteins are separated electrophoreti-cally in a gel medium; transferred from the gel to a protein binding sheet or membrane containing the separated proteins exposed to specific antibodies which bind to, locate, and enable visualization of protein(s) of interest. Further assays may include polymerase chain reaction, blot hybridization (also known as Northern blots) and in situ hybridization.

Details of these and other such assays are described in e.g., U.S. Pat. Nos. 5,656,493; 5,333,675; 5,234,824; 5,187,083 each of which is incorporated herein by reference and in standard references including J. Sambrook and D. W. Rus-sell, Molecular Cloning: A Laboratory Manual, Cold Spring Harbor Laboratory Press; 3rd ed., 2001; F. M. Ausubel, Ed., Short Protocols in Molecular Biology, Current Protocols; 5th ed., 2002; and E. Harlow and D. Lane, Antibodies: A Laboratory Manual, Cold Spring Harbor Laboratory Press, 1988.

According to some embodiments, detectable markers include, without limitation, autoimmune regulator (Aire), CD3+, CD4$^+$, CD8+, CD14, CD16+, CD19+, CD25+, CD45+, CD56+, CD80+, CD86+, CD270, Foxp3+, IL-$\gamma$, IL-$\beta$, IL-1, IL-2, IL-4, IL-5, IL-6, IL-8, IL-10, IL-12, IL-13, IL-15, IL-17, IL-18, IL-21, IL-22, IL-23, IL-27, TGF-31, nitric oxide (NO), PD-L1, BTLA, TNF-$\alpha$, Th1/Th2, C-pep-tide, CCR-7, OCT-4, Nanog, stage-specific embryonic anti-gen (SSEA)-3, and SSEA-4.

Cell viability is determined by excluding the dying cells which take up the intercalating DNA dye 7-aminoactinomy-cin D (7AAD). According to some embodiments, the edu-cated mononuclear cell product is at least about 70% viable by 7-AAD. According to some embodiments, the educated mononuclear cell product is at least about 75% viable by 7-AAD. According to some embodiments, the educated mononuclear cell product is at least about 80% viable by 7-AAD. According to some embodiments, the educated mononuclear cell product is at least about 90% viable by 7-AAD. According to some embodiments the educated mononuclear cell product is at least about 95% viable by 7-AAD.

To determine cell number by flow cytometry, cells obtained from peripheral blood samples are incubated with mouse with mouse anti-human mAbs (BioLegend, San Diego, CA), including PerCP/Cy5.5-conjugated anti-CD3, PerCP/Cy5.5-conjugated anti-CD4, PE-conjugated anti-CD8, FITC-conjugated anti-CD45RA, PE-conjugated anti-CD45RO, PE-conjugated anti-CD56, APC-conjugated anti-CCR7. Cells are immunostained with BD MultiTEST reagents CD3 FITC/CD8 PE/CD45 PerCP/CD4 APC and CD3 FITC/CD16+CD56 PE/CD45 PerCP/CD19 APC (BD Biosciences, San Jose, CA). Isotype-matched mouse anti-human IgG antibodies (Beckman Coulter) serve as a nega-tive control for all fluorescein-conjugated IgG mAb. After staining, the cells are collected and analyzed using a BD FACScalibur™ Cytometer. The final data are analyzed using the CellQuest Pro Software (Becton Dickinson, MD).

For ex vivo studies, cells are stained for 30 minutes at room temperature and then washed with PBS prior to flow analysis. Cells are stained with mouse anti-human mono-clonal Abs (mAbs), including APC-AF 750-conjugated anti-CD4, APC-AF 750- or Krome Orange-conjugated anti-CD8, PE- or FITC-conjugated anti-CD45RA, FITC-conjugated anti-CD45RO, ECD-conjugated anti-CD62L, and PE-Cy7-conjugated anti-CCR7. Isotype-matched mouse anti-human IgG antibodies (Beckman Coulter) serve as a negative control for all fluorescein-conjugated IgG mAb. After stain-ing, cells are collected and analyzed using a Gallios Flow Cytometer (Beckmar Coulter), equipped with 3 lasers (488 nm blue, 638 red, and 405 violet lasers) for co current reading of up to 10 colors. The final data are analyzed using the Kaluza Flow Cytometry Analysis Software (Beckman Coulter).

According to some embodiments, UC-SCs present in the educated mononuclear cell product will be detected by flow cytometry using biomarkers including, without limitation, OCT-4, Nanog, stage-specific embryonic antigen (SSEA)-3, and SSEA-4. According to some embodiments the educated mononuclear cell product contains less than 2% umbilical cord blood mononuclear stem cel s. According to some embodiments the educated mononuclear cell product contains less than 1% umbilical cord blood mononuclear stem cells. According to some embodiments the educated mononuclear cell product contains less than 0.9% umbilical cord blood mononuclear stem cells. According to some embodiments the educated mononuclear cell product contains less than 0.8% umbilical cord blood mononuclear stem cells. According to some embodiments the educated mononuclear cell product contains less than 0.7% umbilical cord blood mononuclear stem cells. According to some embodiments the educated mononuclear cell product contains less than 0.6% umbilical cord blood mononuclear stem cells. According to some embodiments the educated mononuclear cell product contains less than 0.5% umbilical cord blood mononuclear stem cells.

According to some embodiments the educated mononuclear cell product contains less than 0.4% umbilical cord blood mononuclear stem cells. According to some embodiments the educated mononuclear cell product contains less than 0.3% umbilical cord blood mononuclear stem cells. According to some embodiments the educated mononuclear cell product contains less than 0.2% umbilical cord blood mononuclear stem cells. According to some embodiments the educated mononuclear cell product contains less than 0.1% umbilical cord blood mononuclear stem cells. According to some embodiments the educated mononuclear cell product contains less than 0.009% umbilical cord blood mononuclear stem cells. According to some embodiments the educated mononuclear cell product contains less than 0.008% umbilical cord blood mononuclear stem cells. According to some embodiments the educated mononuclear cell product contains less than 0.007% umbilical cord blood mononuclear stem cells. According to some embodiments the educated mononuclear cell product contains less than 0.006% umbilical cord blood mononuclear stem cells. According to some embodiments the educated mononuclear cell product contains less than 0.005% umbilical cord blood mononuclear stem cells. According to some embodiments the educated mononuclear cell product contains less than 0.004% umbilical cord blood mononuclear stem cells. According to some embodiments the educated mononuclear cell product contains less than 0.003% umbilical cord blood mononuclear stem cells. According to some embodiments the educated mononuclear cell product contains less than 0.002% umbilical cord blood mononuclear stem cells. According to some embodiments the educated mononuclear cell product contains less than 0.001% umbilical cord blood mononuclear stem cells.

According to some embodiments, the therapeutically effective amount of the educated mononuclear cell product infused intravascularly into the subject comprises at least $10^4$, at least 105, at least $10^6$, at least 107, at least $10^8$, at least $10^9$, or at least $10^{10}$ mononuclear cells.

According to some embodiments, the minimum time from obtaining the whole blood sample from the subject and infusing the educated mononuclear cell product back to the same subject is about 24 hours. According to some embodiments, the minimum time from obtaining the whole blood sample from the subject and infusing the educated mononuclear cell product back to the same subject is about 25 hours. According to some embodiments, the minimum time from obtaining the whole blood sample from the subject and infusing the educated mononuclear cell product back to the same subject is about 26 hours. According to some embodiments, the minimum time from obtaining the whole blood sample from the subject and infusing the educated mononuclear cell product back to the same subject is about 27 hours. According to some embodiments, the minimum time from obtaining the whole blood sample from the subject and infusing the educated mononuclear cell product back to the same subject is about 28 hours. According to some embodiments, the minimum time from obtaining the whole blood sample from the subject and infusing the educated mononuclear cell product back to the same subject is about 29 hours. According to some embodiments, the minimum time from obtaining the whole blood sample from the subject and infusing the educated mononuclear cell product back to the same subject is about 30 h curs. According to some embodiments, the minimum time from obtaining the whole blood sample from the subject and infusing the educated mononuclear cell product back to the same subject is about 31 hours. According to some embodiments, the minimum time from obtaining the whole blood sample from the subject and infusing the educated mononuclear cell product back to the same subject is about 32 hours. According to some embodiments, the minimum time from obtaining the whole blood sample from the subject and infusing the educated mononuclear cell product back to the same subject is about 33 hours. According to some embodiments, the minimum time from obtaining the whole blood sample from the subject and infusing the educated mononuclear cell product back to the same subject is about 34 hours. According to some embodiments, the minimum time from obtaining the whole blood sample from the subject and infusing the educated mononuclear cell product back to the same subject is about 35 hours. According to some embodiments, the minimum time from obtaining the whole blood sample from the subject and infusing the educated mononuclear cell product back to the same subject is about 36 hours. According to some embodiments, the minimum time from obtaining the whole blood sample from the subject and infusing the educated mononuclear cell product back to the same subject is about 37 hours. According to some embodiments, the minimum time from obtaining the whole blood sample from the subject and infusing the educated mononuclear cell product back to the same subject is about 38 hours. According to some embodiments, the minimum time from obtaining the whole blood sample from the subject and infusing the educated mononuclear cell product back to the same subject is about 39 hours. According to some embodiments, the minimum time from obtaining the whole blood sample from the subject and infusing the educated mononuclear cell product back to the same subject is about 40 hours. According to some embodiments, the minimum time from obtaining the whole blood sample from the subject and infusing the educated mononuclear cell product back to the same subject is about 41 hours. According to some embodiments, the minimum time from obtaining the whole blood sample from the subject and infusing the educated mononuclear cell product back to the same subject is about 42 hours. According t some embodiments, the minimum time from obtaining the whole blood sample from the subject and infusing the educated mononuclear cell product back to the same subject s about 43 hours. According to some embodiments, the minimum time from obtaining the whole blood sample from the subject and infusing the educated mononuclear cell product back to the same subject is about 44 hours. According to some embodiments, the minimum time from obtaining the whole blood sample from the subject and infusing the educated mononuclear cell product back to the same subject is about 45 hours. According to some embodiments, the minimum time from obtaining the whole blood sample from the subject and infusing the educated mononuclear cell product back to the same subject is about 46 hours. According to some embodiments, the minimum time from obtaining the whole blood sample from the subject and infusing the educated mononuclear cell product back to the same subject is about 49 hours. According to some embodiments, the minimum time from obtaining the whole blood sample from the subject and infusing the educated mononuclear cell product back to the same subject is about 50 hours. According to some embodiments, the minimum time from obtaining the whole blood sample from the subject and infusing the educated mononuclear cell product back to the same subject is about 51 hours. According to some embodiments, the minimum time from obtaining the whole blood sample from the subject and infusing the educated mononuclear cell product back to the same subject is about 52 hours. According to some embodiments, the minimum time from obtaining the whole blood sample from the subject and infusing the educated mononuclear cell product back to the same subject is about 53 hours. According to some embodiments, the minimum time from obtaining the whole blood sample from the subject and infusing the educated mononuclear cell product back to the same subject is about 54 hours. According to some embodiments, the minimum time from obtaining the whole blood sample from the subject and infusing the educated mononuclear cell product back to the same subject s about 55 hours. According to some embodiments, the minimum time from obtaining the whole blood sample from the subject and infusing the educated mononuclear cell product back to the same subject is about 56 hours. According to some embodiments, the minimum time from obtaining the whole blood sample from the subject and infusing the educated mononuclear cell product back to the same subject is about 57 hours. According to some embodiments, the minimum time from obtaining the whole blood sample from the subject and infusing the educated mononuclear cell product back to the same subject is about 58 hours. According to some embodiments, the minimum time from obtaining the whole blood sample from the subject and infusing the educated mononuclear cell product back to the same subject is about 59 hours. According to some embodiments, the minimum time from obtaining the whole blood sample from the subject and infusing the educated mononuclear cell product back to the same subject is about 60 hours. According to some embodiments, the minimum time from obtaining the whole blood sample from the subject and infusing the educated mononuclear cell product back to the same subject is about 61 hours. According to some embodiments, the minimum time from obtaining the whole blood sample from the subject and infusing the educated mononuclear cell product back to the same subject is about 62 hours. According to some embodiments, the minimum time from obtaining the whole blood sample from the subject and infusing the educated mononuclear cell product back to the same subject is about 63 hours. According to some embodiments, the minimum time from obtaining the whole blood sample from the subject and infusing the educated mononuclear cell product back to the same subject is about 64 hours. According to some embodiments, the minimum time from obtaining the whole blood sample from the subject and infusing the educated mononuclear cell product back to the same subject is about 65 hours. According to some embodiments, the minimum time from obtaining the whole blood sample from the subject and infusing the educated mononuclear ell product back to the same subject is about 66 hours. According to some embodiments, the minimum time from obtaining the whole blood sample from the subject and infusing the educated mononuclear cell product back to the same subject is about 67 hours. According to some embodiments, the minimum time from obtaining the whole blood sample from the subject and infusing the educated mononuclear cell product back to the same subject is about 68 hours. According to some embodiments, the minimum time from obtaining the whole blood sample from the subject and infusing the educated mononuclear cell product back to the same subject is about 69 hours. According to some embodiments, the minimum time from obtaining the whole blood sample from the subject and infusing the educated mononuclear cell product back to the same subject is about 70 hours. According to some embodiments, the minimum time from obtaining the whole blood sample from the subject and infusing the educated mononuclear ell product back to the same subject is about 71 hours. According to some embodiment, the minimum time from obtaining the whole blood sample from the subject and infusing the educated mononuclear cell product back to the same subject is about 72 hours.

According to some embodiments, the therapeutically effective amount of the educated mononuclear cell product is effective to modulate autoreactivity in a T cell compartment of the subject, and to reduce symptoms of the immune disease. According to some embodiments, the biological effect, i.e., reducing autoreactivity in a T cell compartment, is measurable by measuring a suitable biomarker. The term "biomarker" (or "biosignature") refers to a peptide, protein, nucleic acid, antibody, gene, metabolite, or any other substance used as an indicator of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). According to some embodiments, in evaluating the described therapy, one or more biomarker may be used as a surrogate for a natural endpoint, such as survival or irreversible morbidity. If the treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

According to some embodiments, the therapeutic amount of the educated mononuclear product is effective to delay onset, to delay progression, to modulate autoreactivity in a T cell compartment of the subject, to reduce symptoms of the immune disease, or a combination thereof. According to some embodiments, a result of the modulating comprises an increase in growth, proliferation, or both of functional β-cells in the pancreas of the subject that has some residual β cell function. According to some embodiments, the modulating comprises reducing secretion of a proinflammatory cytokine, e.g., IL-4, IL-5, IL-12 and IL-17. According to some embodiments, the modulating comprises altering a population of mononuclear cells in the educated mononuclear product graft.

According to some embodiments, the duration of the modulation of autoreactivity persists for at least 1 month. According to some embodiments, the duration of the modulation of autoreactivity persists for at least 2 months. According to some embodiments, the duration of the modulation of autoreactivity persists for at least 3 months. According to some embodiments, the duration of the modulation of autoreactivity persists for at least 4 months. According to some embodiments, the duration of the modulation of autoreactivity persists for at least 5 months. According to some embodiments, the duration of the modulation of autoreactivity persists for at least 6 months. According to some embodiments, the duration of the modulation of autoreactivity persists for at least 7 months. According to some embodiments, the duration of the modulation of autoreactivity persists for at least 8 months. According to some embodiments, the duration of the modulation of autoreactivity persists for at least 9 months. According to some embodiments, the duration of the modulation of autoreactivity persists for at least 10 months. According to some embodiments, the duration of the modulation of autoreactivity persists for at least 11 months. According to some embodiments, the duration of the modulation of autoreactivity persists for at least 12 months.

According to some embodiments, the steps of the method are repeated in order at a plurality of infusion dates over the subject's lifetime as needed.

According to some embodiments, the method may be effective to maintain and improve islet β-cell function in individuals with residual B-cell function. According to some embodiments, the method may be effective to alter Tmemory populations. According to some embodiments, the method may be effective to convert some of the cells in the educated mononuclear cell product into tolerizing agents.

Compositions

According to another aspect, the described invention provides a pharmaceutical composition for treating a disease characterized by lymphocyte autoreactivity, comprising a therapeutic amount of an educated mononuclear cell product, wherein the therapeutic amount of the educated mononuclear cell product is effective to modulate autoreactivity in a T cell compartment of the subject, and to reduce symptoms of the immune disease, and wherein the educated mononuclear cell product is produced by a process comprising:

(1) acquiring under sterile conditions a whole blood sample containing mononuclear cells from a subject diseased with the disease characterized by lymphocyte autoreactivity;

(2) transporting the whole blood sample of (1) to a processing facility;

(3) sterilely purifying the mononuclear cells (MNC) from the whole blood sample to form a mononuclear cell preparation;

(4) introducing the mononuclear cell preparation into a bioreactor device comprising a viable population of adherent umbilical cord blood stem cells (UC-SCs), wherein the adherent UC-SCs are at least 80% confluent;

(5) co-culturing the mononuclear cell preparation with the UC-SCs so that the mononuclear cells in the mononuclear cell preparation and the UC-SCs can interact for at least 0.1 hour, at least 0.2 hour, at least 0.3 hour, at least 0.4 hour, at least 0.5 hour, at least 0.6 hour, at least 0.7 hour, at least 0.8 hour, at least 0.9 hour, at least 1.0 hour, at least 1.5 hours, at least 2 hours, at least 2.5 hours, at least 3 hours, at least 3.5 hours, at least 4 hours, at least 4.5 hours, at least 5 hours, at least 5.5 hours, at least 6 hours, at least 6.5 hours, at least 7 hours, at least 7.5 hours, or at least 8 hours under sterile conditions to form the educated mononuclear cell product, and wherein the therapeutically effective amount of the educated mononuclear cell product is effective to modulate autoreactivity in a T cell compartment of the subject, and to reduce symptoms of the immune disease, wherein the educated mononuclear cell product comprises:

(i) at least at least $1 \times 10^8$, at least $1 \times 10^9$, $1 \times 10^{10}$ mononuclear cells; and (ii) a modulated population of T cells selected from the group consisting of $T_{EM}$ CD4$^+$, $T_{EM}$ CD8$^+$, $T_{CM}$ CD4$^+$CD45RA$^-$CCR7$^+$, $T_{CM}$ CD8$^+$CCR7$^+$, $T_{CM}$ CD45RO$^+$ CCR7$^+$, $T_{EM}$ CD45RO$^+$ CCR7$^-$, $T_{CM}$ CD8$^+$, naïve CD4+CCR7$^+$, naïve CD8$^+$CCR7$^+$, $T_{EM}$ CD4$^+$CCR7$^+$, $T_{EM}$ CD45RO$^+$CD62L$^-$, $T_{EM}$ CD8$^+$ CCR7$^+$, $T_{CM}$ CD4$^+$, naïve CD4$^+$CD45RA$^+$CCR7$^+$, $T_{CM}$CD4$^+$CCR7$^+$, CD4$^+$HLA$^-$DR+ and CD8$^+$HLA$^-$DR$^+$ cells;

wherein $T_{CM}$ are central memory T cells and $T_{FM}$ are effector memory T cells.

According to some embodiments, the mononuclear cell population comprises a population of immunomodulatory cells. According to some embodiments, the population of immunomodulatory cells comprises a population of eukocytes. According to some embodiments, the population of leukocytes comprises a population of lymphocytes, a population of granulocytes, a population of basophils, a population of monocytes, or a combination thereof. According to some embodiments, the population of immunomodulatory cells comprises a population of antigen-capturing cells, a population of antigen presenting cells, or both. According to some embodiments, the population of antigen presenting cells expresses CD80, CD86, or both. According to some embodiments, the population of antigen presenting cells comprises macrophages, dendritic cells or both. According to some embodiments, the population of lymphocytes comprises a population of T lymphocytes, a population of B lymphocytes, a population of natural killer (NK) cells, or a combination thereof.

According to some embodiments, the population of T lymphocytes comprises one or more populations of T cells. According to some embodiments, the population of T cells comprises activated T cells. According to some embodiments, the population of activated T cells is selected from the group consisting of naive T cells, primed T-cells, activated T cells, effector T cells, cytotoxic T cells, T helper cells, memory T cells, NK cells, and Treg cells. According to some embodiments the population of T cells comprises T cells expressing one or more inflammatory mediator (lymphokines). According to some embodiments, the inflammatory mediators are selected from the group consisting of interleukin-1-beta (IL-13), IL-2, interleukin-4 (IL-4), IL-5, interleukin-6 (IL-6), interleukin-8 (II-8), IL-10, tumor necrosis factor-alpha (TNF-α), interferon-gamma (IFN-γ), interleukin-12 (IL-12), and Lymphotoxin. According to some embodiments the population of T lymphocytes comprises T cells expressing one or more marker selected from the group consisting of T cell receptor (TCR)/CD3, CD4, CD8, CD25, CD28, CD40 ligand (CD40L), Fox3, fas, MHC I, MHCII, immunoreceptor tyrosine-based activation motif (ITAM), ZAP70 (zeta associated protein.

According to some embodiments, the population of B lymphocytes comprises one or more populations of B cells. According to some embodiments, the population of B cells comprises activated B cells. According to some embodiments, the population of B cells is selected from the group consisting of naive B cells, activated B cells, plasmaplasts, and memory B cells. According to some embodiments the population of B lymphocytes comprises B cells expressing one or more marker selected from the group consisting of MHC class II, CD40, an immunoglobulin.

Methods for purifying mononuclear cells from whole blood samples are well known. According to one embodiment, red blood cells are removed by density gradient centrifugation, e.g., using Ficoll Paque fractionation, to separate the buffy coat from red blood cells. The term "buffy coat" refers to a thin grayish white fraction of a blood sample that contains most of the leukocytes.

According to some embodiments, purification of mononuclear cells from the whole blood sample is by apheresis using an automated apheresis separator. In brief, whole blood is taken from the patient and then passed through an apparatus containing a spinning chamber. The blood separates into its components (plasma, platelet rich plasma, leukocytes and red blood cells) by gravity along the wall of the chamber. Mononuclear cells are sorted out and the remaining blood components are re-introduced back into the bloodstream of the patient.

According to some embodiments, magnetic bead activated cell sorting is a positive selection technique used for purifying a specific cell population from peripheral blood mononuclear cells. Because the quantity and activity of the desired cells may decrease after such protocols, some prefer gentler substrate adhesion and negative selection protocols.

According to some embodiments, the bioreactor device comprises one or more surfaces comprising a viable population of adherent umbilical cord blood stem cells (UC-SC's). The method for preparing the bioreactor comprising the UC-SCs comprises:

(a) obtaining a fresh cord blood unit obtained from healthy donors;

(b) separating the mononuclear cell fraction from the umbilical cord blood by density gradient centrifugation using Ficoll HISTOPAQUE;

(c) removing red blood cells;

(d) washing the UC-mononuclear cells with a physiological buffered saline;

(e) seeding mononuclear cells in the bioreactor in a serum-free culture medium; wherein the seeding density is at least $1 \times 10^6$ cells;

(f) culturing the mononuclear cells in a serum-free culture medium, changing half/the medium every 2-3 days to remove nonadherent cells, for at least 10 days to grow to at least 80% confluence; and (g) Incubating the bioreactor at 37° C.; and (h) confirming sterility and viability of a sample of the CB-SC cultures.

The cultures of CB-SCs are round and are attached in the bottom surface of the bioreactor device. According to some embodiments, the surface of the bioreactor device is an uncoated plastic. According to some embodiments the surface of the bioreactor device is a positively charged surface. According to some embodiments, the surface of the bioreactor device is a hydrophobic surface, for example, polystyrene or glass. According to some embodiments, the surface of the bioreactor device is coated. According to some embodiments, the surface of the bioreactor de ice does not comprise a cell feeder layer.

According to some embodiments, the umbilical cord blood mononuclear cells are grown to at least 80% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 85% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 90% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 95% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 96% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing According to some embodiments of the invention, the umbilical cord blood mononuclear cells are grown to at least 97% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing. According to some embodiments of the invention, the umbilical cord blood mononuclear cells are grown to at least 99% confluence for at least 10 days, at least 11 days, at least 12 days, at least 13 days, at least 14 days, at least 15 days, at least 16 days, at least 17 days, at least 18 days, at least 19 days, at least 0 days or at least 21 days prior to co-culturing. According to some embodiments of th invention, the umbilical cord blood mononuclear cells are grown to at least 99% confluence for at least 10 days, at least 11 days, at least 12 days, at least 13 days, at least 14 days, at least 15 days, at least 16 days, at least 17 days, at least 18 days, at least 19 days, at least 20 days or at least 21 days prior to co-culturing.

The mononuclear cell preparation from the patient is introduced into the bioreactor for co-cultivating the patient's mononuclear cells and the UC-SC cells. According to some embodiments, the mononuclear preparation is separated from the UC-SC layer. According to some embodiments, the patient's mononuclear cells are nonadherent. According to some embodiments the patient's mononuclear cells contact the cells in the UC-SC layer. According to some embodiments the culture medium comprises growth factors, soluble inflammatory mediators, and the like. According to some embodiments, the culture medium is effective to support both the patient's mononuclear cells and the UC-SC cell layer. According to some embodiments, the culture medium comprises immunomodulatory mediators and soluble factors produced by the patient's mononuclear cells and by the UC-SC cells.

According to some embodiments the interacting conditions comprise gentle rocking of the bioreactor. According to some embodiments, the gentle rocking of the bioreactor is intermittent. According to some embodiments, the medium is circulated through the bioreactor.

The patient's mononuclear preparation and the CB-SCs are co-cultivated under interacting conditions for at least 2 hours under sterile conditions. The patient's mononuclear preparation and the CB-SCs are co-cultivated under interacting conditions for at least 3 hours under sterile conditions. The patient's mononuclear preparation and the CB-SCs are co-cultivated under interacting conditions for at least 4 hours under sterile conditions. The patient's mononuclear preparation and the CB-SCs are co-cultivated under interacting conditions for at least 5 hours under sterile conditions. The patient's mononuclear preparation and the CB-SCs are co-cultivated under interacting conditions for at least 6 hours under sterile conditions. The patient's mononuclear preparation and the CB-SCs are co-cultivated under interacting conditions for at least 7 hours under sterile conditions. The patient's mononuclear preparation and the CB-SCs are co-cultivated under interacting conditions for at least 8 hours under sterile conditions. The patient's mononuclear preparation and the CB-SCs are co-cultivated under interacting conditions for at least 9 hours under sterile conditions. The patient's mononuclear preparation and the CB-SCs are co-cultivated under interacting conditions for at least 10 hours under sterile conditions. The patient's mononuclear preparation and the CB-SCs are co-cultivated under interacting conditions for at least 11 hours under sterile conditions. The patient's mononuclear preparation and the CB-SCs are co-cultivated under interacting conditions for at least 12 hours under sterile conditions. The patient's mononuclear preparation and the CB-SCs are co-cultivated under interacting conditions for at least 13 hours under sterile conditions. The patient's mononuclear preparation and the CB-SCs are co-cultivated under interacting conditions for at least 14 hours under sterile conditions. The patient's mononuclear preparation and the CB-SCs are co-cultivated under interacting conditions for at least 15 hours under sterile conditions. The patient's mononuclear preparation and the CB-SCs are co-cultivated under interacting conditions for at least 16 hours under sterile conditions. The patient's mononuclear preparation and the CB-SCs are co-cultivated under interacting conditions for at least 17 hours under sterile conditions. The patient's mononuclear preparation and the CB-SCs are co-cultivated under interacting conditions for at least 18 hours under sterile conditions. The patient's mononuclear preparation and the CB-SCs are co-cultivated under interacting conditions for at least 19 hours under sterile conditions. The patient's mononuclear preparation and the CB-SCs are co-cultivated under interacting conditions for at least 20 hours under sterile conditions. The patient's mononuclear preparation and the CB-SCs are co-cultivated under interacting conditions for at least 21 hours under sterile condition. The patient's mononuclear preparation and the CB-SCs are co-cultivated under interacting conditions for at least 22 hours under sterile conditions. The patient's mononuclear preparation and the CB-SCs are co-cultivated under interacting conditions for at least 23 hours under sterile conditions. The patient's mononuclear preparation and the CB-SCs are co-cultivated under interacting conditions for at least 24 hours under sterile conditions.

According to some embodiments, the umbilical cord blood mononuclear stem cells and patient mononuclear cells are co-cultivated at a ratio of at least 1:2. According to some embodiments, the umbilical cord blood mononuclear stem cells and patient mononuclear cells are co-cultivated at a ratio of at least 1:5. According to some embodiments, the umbilical cord blood mononuclear stem cells and patient mononuclear cells are co-cultivated at a ratio of at least 1:10. According to some embodiments, the umbilical cord blood mononuclear stem cells and patient mononuclear cells are co-cultivated at a ratio of at least 1:20. According to some embodiments, the umbilical cord blood mononuclear stem cells and patient mononuclear cells are co-cultivated at a ratio of at least 1:50. According to some embodiments, the umbilical cord blood mononuclear stem cells and patient mononuclear cells are co-cultivated at a ratio of at least 1:60. According to some embodiments, the umbilical cord blood mononuclear stem cells and patient mononuclear cells are co-cultivated at a ratio of at least 1:70. According to some embodiments, the umbilical cord blood mononuclear stem cells and patient mononuclear cells are co-cultivated at a ratio of at least 1:80. According to some embodiments, the umbilical cord blood mononuclear stem cells and patient mononuclear cells are co-cultivated at a ratio of at least 1:90. According to some embodiments, the umbilical cord blood mononuclear stem cells and patient mononuclear cells are co-cultivated at a ratio of at least 1:100.

The result of this interaction is an educated mononuclear cell product.

The educated mononuclear cell product is harvested under sterile conditions from the bioreactor device.

Assays for confirming purity, sterility, and viability of the educated mononuclear cell product; percent viability include the following.

According to some embodiments, endotoxin levels of the educated mononuclear cell product are less than about 0.5 endotoxin units/mL, and the educated mononuclear cell product is Gram stain negative. The educated mononuclear cell product is also tested for *Mycoplasma* and sterility, e.g., by real-time PCR in compliance with the requirements of US FDA Good Laboratory Practice Regulations.

A "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

Markers can be assayed by any of various established methods. Antibody-based techniques include, without limitation, fluorescence activated cell sorting (FACS) immunofluorescence, enzyme immunohistochemistry, and immunoblotting. Further assays may include assays for detection of cytokine levels or mRNAs or "Western blot" techniques detecting the encoding of a particular marker. The term, "Western blot" refers to a method for identifying proteins in a complex mixture; proteins are separated electrophoretically in a gel medium; transferred from the gel to a protein binding sheet or membrane containing the separated proteins exposed to specific antibodies which bind to, locate, and enable visualization of protein(s) of interest. Further assays may include polymerase chain reaction, blot hybridization (also known as Northern blots) and in situ hybridization. Details of these and other such assays are described in e.g., U.S. Pat. Nos. 5,656,493; 5,333,675; 5,234,824; 5,187,083 each of which is incorporated herein by reference and in standard references including J. Sambrook and D. W. Russell, Molecular Cloning: A Laboratory Manual, Cold Spring Harbor Laboratory Press; 3rd ed., 2001; F. M. Ausubel, Ed., Short Protocols in Molecular Biology, Current Protocols; 5th ed., 2002; and E. Harlow and D. Lane, Antibodies: A Laboratory Manual, Cold Spring Harbor Laboratory Press, 1988.

According to some embodiments, detectable markers include, without limitation, autoimmune regulator (Aire), CD3+, CD4+, CD8+, CD14, CD16+, CD19+, CD25+, CD45+, CD56+, CD80+, CD86+, CD270, Foxp3+, IL-γ, IL-β, IL-1, IL-2, IL-4, IL-5, IL-6, IL-8, IL-10, IL-12, IL-13, IL-15, IL-17, IL-18, IL-21, IL-22, IL-23, IL-27, TGF-31, nitric oxide (NO), PD-L1, BTLA, TNF-α, Th1/Th2, C-peptide, CCR-7, OCT-4, Nanog, stage-specific embryonic antigen (SSEA)-3, and SSEA-4.

Cell viability is determined by excluding the dying cells which take up the intercalating DNA dye 7-aminoactinomycin D (7AAD). According to some embodiments, the educated mononuclear cell product is at least bout 70% viable by 7-AAD. According to some embodiments, the educated mononuclear cell product is at least about 75% viable by 7-AAD. According to some embodiments, the educated mononuclear cell product is at least about 80% viable by 7-AAD. According to some embodiments, the educated mononuclear cell product is at least about 90% viable by 7-AAD. According to some embodiments the educated mononuclear cell product is at least about 95% viable by 7-AAD.

To determine cell number by flow cytometry, cells obtained from peripheral blood samples are incubated with mouse with mouse anti-human mAbs (BioLegend, San Diego, CA), including PerCP/Cy5.5-conjugated anti-CD3, PerCP/Cy5.5-conjugated anti-CD4, PE-conjugated anti-CD8, FITC-conjugated anti-CD45RA, PE-conjugated anti-CD45RO, PE-conjugated anti-CD56, APC-conjugated anti-CCR7. Cells are immunostained with BD MultiTEST reagents CD3 FITC/CD8 PE/D45 PerCP/CD4 APC and CD3 FITC/CD16+CD56 PE/CD45 PerCP/CD19 APC (BD Biosciences, San Jose, CA). Isotype-matched mouse anti-human IgG antibodies (Beckman Coulter) serve as a negative control for all fluorescein-conjugated IgG mAb. After staining, cells are collected and analyzed using a BD FACScalibur™ Cytometer. The final data are analyzed using the CellQuest Pro Software (Becton Dickinson, MD).

For ex vivo studies, cells are stained for 30 minutes at r om temperature and then washed with PBS prior to flow analysis. Cells are stained with mouse anti-human monoclonal Abs (mAbs), including APC-AF 750-conjugated anti-D4, APC-AF 750- or Krome Orange-conjugated anti-CD8, PE- or FITC-conjugated anti-CD45RA, FITC-conjugated anti-CD45RO, ECD-conjugated anti-CD62L, and PE-Cy7-conjugated anti-CCR7. Isotype-matched mouse anti-human IgG antibodies (Bec man Coulter) serve as a negative control for all fluorescein-conjugated IgG mAb. After staining, cells are collected and analyzed using a Gallios Flow Cytometer (Beckman Coulter), equipped with 3 lasers (488 nm blue, 638 red, and 405 violet lasers) for concurrent reading of up to 10 colors. The final data are analyzed using the Kaluza Flow Cytometry Analysis Software (Beckman Coulter).

According to some embodiments, UC-SCs present in the educated mononuclear cell product are detectable by flow cytometry using biomarkers, including, without limitation, OCT-4, Nanog, stage-specific embryonic antigen (SSEA)-3, and SSEA-4. According to some embodiments the educated mononuclear cell product contains less than 2% umbilical cord blood mononuclear stem cells. According to some embodiments the educated mononuclear cell product contains less than 1% umbilical cord blood mononuclear stem cells. According to some embodiments the educated mononuclear cell product contains less than 0.9% umbilical cord blood mononuclear stem cells. According to some embodiments the educated mononuclear cell product contains less than 0.8% umbilical cord blood mononuclear stem cells. According to some embodiments the educated mononuclear cell product contains less than 0.7% umbilical cord blood mononuclear stem cells. According to some embodiments the educated mononuclear cell product contains less than 0.6% umbilical cord blood mononuclear stem cells. According to some embodiments the educated mononuclear cell product contains less than 0.5% umbilical cord blood mononuclear stem cells. According to some embodiments the educated mononuclear cell product contains less than 0.4% umbilical cord blood mononuclear stem cells. According to some embodiments the educated mononuclear cell product contains less than 0.3% umbilical cord blood mononuclear stem cells. According to some embodiments the educated mononuclear cell product contains less than 0.2% umbilical cord blood mononuclear stem cells. According to some embodiments the educated mononuclear cell product contains less than 0.1% umbilical cord blood mononuclear stem cells. According to some embodiments the educated mononuclear cell product contains less than 0.009% umbilical cord blood mononuclear stem cells. According to some embodiments the educated mononuclear cell product contains less than 0.008% umbilical cord blood mononuclear stem cells. According to some embodiments the educated mononuclear cell product contains less than 0.007% umbilical cord blood mononuclear stem cells. According to some embodiments the educated mononuclear cell product contains less than 0.006% umbilical cord blood mononuclear stem cells. According to some embodiments the educated mononuclear cell product contains less than 0.005% umbilical cord blood mononuclear stem cells. According to some embodiments the educated mononuclear cell product contains less than 0.004% umbilical cord blood mononuclear stem cells. According to some embodiments the educated mononuclear cell product contains less than 0.003% umbilical cord blood mononuclear stem cells. According to some embodiments the educated mononuclear cell product contains less than 0.002% umbilical cord blood mononuclear stem cells. According to some embodiments the educated mononuclear cell product contains less than 0.001% umbilical cord blood mononuclear stem cells.

According to some embodiments, the therapeutically effective amount of the educated mononuclear cell product infused intravascularly into the subject comprises at least $10^4$, at least $10^5$, at least $10^6$, at least $10^7$, at least $10^8$, at least $10^9$, or at least $10^{10}$ educated mononuclear cells.

According to some embodiments, the minimum time from obtaining the whole blood sample from the subject and infusing the educated mononuclear cell product back to the same subject is about 24 hours. According to some embodiments, the minimum time from obtaining the whole blood sample from the subject and infusing the educated mononuclear cell product back to the same subject is about 25 hours. According to some embodiments, the minimum time from obtaining the whole blood sample from the subject and infusing the educated mononuclear cell product back to the same subject is about 26 hours. According to some embodiments, the minimum time from obtaining the whole blood sample from the subject and infusing the educated mononuclear cell product back to the same subject is about 27 hours. According t some embodiments, the minimum time from obtaining the whole blood sample from the subject and infusing the educated mononuclear cell product back to the same subject is about 28 hours. According to some embodiments, the minimum time from obtaining the whole blood sample from the subject and infusing the educated mononuclear cell product back to the same subject is about 29 hours. According to some embodiments, the minimum time from obtaining the whole blood sample from the subject and infusing the educated mononuclear cell product back to the same subject is about 30 hours. According to some embodiments, the minimum time from obtaining the whole blood sample from the subject and infusing the educated mononuclear cell product back to the same subject is about 31 hours. According to some embodiments, the minimum time from obtaining the whole blood sample from the subject and infusing the educated mononuclear cell product back to the same subject is about 32 hours. According to some embodiments, the minimum time from obtaining the whole blood sample from the subject and infusing the educated mononuclear cell product back to the same subject is about 33 hours. According to some embodiments, the minimum time from obtaining the whole blood sample from the subject and infusing the educated mononuclear cell product back to the same subject is about 34 hours. According to some embodiments, the minimum time from obtaining the whole blood sample from the subject and infusing the educated mononuclear cell product back to the same subject is about 35 hours. According to some embodiments, the minimum time from obtaining the whole blood sample from the subject and infusing the educated mononuclear cell product back to the same subject is about 36 hours. According to some embodiments, the minimum time from obtaining the whole blood sample from the subject and infusing the educated mononuclear cell product back to the same subject is about 37 hours. According to some embodiments, the minimum time from obtaining the whole blood sample from the subject and infusing the educated mononuclear cell product back to the same subject is about 38 hours. According to some embodiments, the minimum time from obtaining the whole blood sample from the subject and infusing the educated mononuclear ell product back to the same subject is about 39 hours. According to some embodiments, the minimum time from obtaining the whole blood sample from the subject and infusing the educated mononuclear cell product back to the same subject is about 40 hours. According to some embodiments, the minimum time from obtaining the whole blood sample from the subject and infusing the educated mononuclear cell product back to the same subject is about 41 hours. According to some embodiments, the minimum t me from obtaining the whole blood sample from the subject and infusing the educated mononuclear cell product back to the same subject is about 42 hours. According to some embodiments, the minimum time from obtaining the whole blood sample from the subject and infusing the educated mononuclear cell product back to the same subject s about 43 hours. According to some embodiments, the minimum time from obtaining the whole blood sample from the subject and infusing the educated mononuclear cell product back to the same subject is about 44 hours. According to some embodiments, the minimum time from obtaining the whole blood sample from the subject and infusing the educated mononuclear cell product back to the same subject is about 45 hours. According to some embodiments, the minimum time from obtaining the whole blood sample from the subject and infusing the educated mononuclear cell product back to the same subject is about 46 hours. According to some embodiments, the minimum lime from obtaining the whole blood sample from the subject and infusing the educated mononuclear cell product back to the same subject is about 49 hours. According to some embodiments, the minimum time from obtaining the whole blood sample from the subject and infusing the educated mononuclear cell product back to the same subject is about 50 hours. According to some embodiments, the minimum time from obtaining the whole blood sample from the subject and infusing the educated mononuclear cell product back to the same subject is about 51 hours. According to some embodiments, the minimum time from obtaining the whole blood sample from the subject and infusing the educated mononuclear cell product back to the same subject is about 52 hours. According to some embodiments, the minimum time from obtaining the whole blood sample from the subject and infusing the educated mononuclear cell product back to the same subject is about 53 hours. According to some embodiments, the minimum time from obtaining the whole blood sample from the subject and infusing the educated mononuclear cell product back to the same subject is about 54 hours. According to some embodiments, the minimum time from obtaining the whole blood sample from the subject and infusing the educated mononuclear cell product back to the same subject is about 55 hours. According to some embodiments, the minimum time from obtaining the whole blood sample from the subject and infusing the educated mononuclear cell product back to the same subject is about 56 hours. According to some embodiments, the minimum time from obtaining the whole blood sample from the subject and infusing the educated mononuclear cell product back to the same subject is about 57 hours. According to some embodiments, the minimum time from obtaining the whole blood sample from the subject and infusing the educated mononuclear cell product back to the same subject is about 58 hours. According to some embodiments, the minimum time from obtaining the whole blood sample from the subject and infusing the educated mononuclear cell product back to the same subject is about 59 hours. According to some embodiments, the minimum time from obtaining the whole blood sample from the subject and infusing the educated mononuclear cell product back to the same subject is about 60 hours. According to some embodiments, the minimum time from obtaining the whole blood sample from the subject and infusing the educated mononuclear cell product back to the same subject is about 61 hours. According to some embodiments, the minimum time from obtaining the whole blood sample from the subject and infusing the educated mononuclear cell product back to the same subject is about 62 hours. According to some embodiments, the minimum time from obtaining the whole blood sample from the subject and infusing the educated mononuclear cell product back to the same subject is about 63 hours. According to some embodiments, the minimum time from obtaining the whole blood sample from the subject and infusing the educated mononuclear cell product back to the same subject is about 64 hours. According to some embodiments, the minimum time from obtaining the whole blood sample from the subject and infusing the educated mononuclear cell product back to the same subject is about 65 hours. According to some embodiments, the minimum time from obtaining the whole blood sample from the subject and infusing the educated mononuclear cell product back to the same subject is about 66 hours. According to some embodiments, the minimum time from obtaining the whole blood sample from the subject and infusing the educated mononuclear cell product back to the same subject is about 67 hours. According to some embodiments, the minimum time from obtaining the whole blood sample from the subject and infusing the educated mononuclear cell product back to the same subject is about 68 hours. According to some embodiments, the minimum time from obtaining the whole blood sample from the subject and infusing the educated mononuclear cell product back to the same subject is about 69 hours. According to some embodiments, the minimum time from obtaining the whole blood sample from the subject and infusing the educated mononuclear cell product back to the same subject is about 70 hours. According to some embodiments, the minimum time from obtaining the whole blood sample from the subject and infusing the educated mononuclear cell product back to the same subject is about 71 hours. According to some embodiments, the minimum time from obtaining the whole blood sample from the subject and infusing the educated mononuclear cell product back to the same subject is about 72 hours.

According to some embodiments, the therapeutic amount of the educated mononuclear product is effective to delay onset, to delay progression, to modulate autoreactivity in a T cell compartment of the subject, to reduce symptoms of the immune disease, or a combination thereof. According to some embodiments, the T cell compartment comprises one or more of CD4+$T_{CM}$ (CD45RA-CCR7$^+$), Tregs, CD4+HLA-DR+ or CD8+HLA$^-$DR+ T cells. According to some embodiments, result of the modulating comprises an increase in growth, proliferation, or both of functional β-cells in the pancreas of the subject. According to some embodiments, the modulating comprises reducing secretion of a proinflammatory cytokine, e.g., IL-4, IL-5, IL-12 and IL-17. According to some embodiments, the modulating comprises altering a population of mononuclear cells in the educated mononuclear product graft.

According to some embodiments, the duration of the modulation of autoreactivity persists for at least 1 month. According to some embodiments, the duration of the modulation of autoreactivity persists for at least 2 months. According to some embodiments, the duration of the modulation of autoreactivity persists for at least 3 months. According to some embodiments, the duration of the modulation of autoreactivity persists for at least 4 months. According to some embodiments, the duration of the modulation of autoreactivity persists for at least 5 months. According to some embodiments, the duration of the modulation of autoreactivity persists for at least 6 months. According to some embodiments, the duration of the modulation of autoreactivity persists for at least 7 months. According to some embodiments, the duration of the modulation of autoreactivity persists for at least 8 months. According to some embodiments, the duration of the modulation of autoreactivity persists for at least 9 months. According to some embodiments, the duration of the modulation of autoreactivity persists for at least 10 months. According to some embodiments, the duration of the modulation of autoreactivity persists for at least 11 months. According to some embodiments, the duration of the modulation of autoreactivity persists for at least 12 months.

According to some embodiments, the steps of the method are repeated in order at a plurality of infusion dates over the subject's lifetime as needed.

According to some embodiments, the method is effective to maintain and improve islet β-cell function in individuals with residual β-cell function. According to some embodiments, the method is effective to alter Tmemory populations. According to some embodiments, the method is effective to convert MNCs into tolerizing agents, which can tolerize cells.

According to some embodiments, the composition of the described invention may be formulated with an excipient, carrier or vehicle including, but not limited to, a solvent. The terms "excipient", "carrier", or "vehicle" as used herein refers to carrier materials suitable for formulation and administration of the composition described herein. Carriers and vehicles useful herein include any such materials know in the art which are nontoxic and do not interact with other components. As used herein the phrase "pharmaceutically acceptable carrier" refers to any substantially non-toxic carrier useable for formulation and administration of the composition of the present invention in which the chemotactic hematopoietic stem cell product of the present invention will remain stable and bioavailable.

The pharmaceutically acceptable carrier must be of sufficiently high purity and of sufficiently low toxicity to render it suitable for administration to the mammal being treated. It further should maintain the stability and bioavailability of the educated mononuclear cell product. Exemplary pharmaceutically acceptable carriers for the compositions of the described invention include, without limitation, buffers, diluents and other suitable additives. The term "buffer" as used herein refers to a solution or liquid whose chemical makeup neutralizes acids or bases without a significant change in pH. Examples of buffers envisioned by the present invention include, but are not limited to, Dulbecco's phosphate buffered saline (PBS), Ringer's solution, 5% dextrose in water (D5W), normal/physiologic saline (0.9% NaCl). According to some embodiments, the infusion solution is isotonic to subject tissues. According to some embodiments, the infusion solution is hypertonic to subject tissues. Compositions of the described invention can include pharmaceutically acceptable carriers such as sterile aqueous solutions, non-aqueous solutions in common solvents such as alcohols, or solutions in a liquid oil base.

According to some embodiments, the carrier of the composition of the present invention may include a release agent such as sustained release or delayed release carrier. According to such embodiments, the carrier can be any material capable of sustained or delayed release of the active to provide a more efficient administration, e.g., resulting in less frequent and/or decreased dosage of the composition, improve ease of handling, and extend or delay effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The compositions of the present invention may be administered parenterally in the form of a sterile injectable aqueous or oleaginous suspension. The term "parenteral" or "parenterally" as used herein refers to introduction into the body by way of an injection (i.e., administration by injection), including, but not limited to, infusion techniques. The composition of the present invention comprising a chemotactic hematopoietic stem cell product is delivered to the subject by means of a balloon catheter adapted for delivery of the fluid compositions (i.e., compositions capable of flow) into a selected anatomical structure.

The sterile pharmaceutical composition of the described invention may be a sterile solution or suspension in a nontoxic parenterally acceptable diluent or solvent. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it does not rapidly settle out. In everyday life, the most common suspensions are those of solids in liquid water. Exemplary vehicles and solvents that may be employed are water, Ringer's solution, and isotonic sodium chloride (saline) solution. According to some embodiments, hypertonic solutions are employed. In addition, sterile, fixed oils may be employed as a solvent or suspending medium. For parenteral application, exemplary vehicles consist of solutions, e.g., oily or aqueous solutions, as well as suspensions, emulsions, or implants. Aqueous suspensions may contain substances which increase the viscosity of the suspension and include, for example, sodium carboxymethyl cellulose, sorbitol and/ or dextran.

Additional compositions of the described invention can be readily prepared using technology which is known in the art such as described in Remington's Pharmaceutical Sciences, 18th or 19th editions, published by the Mack Publishing Company of Easton, Pa., which is incorporated herein by reference.

According to another aspect of the described invention, the pharmaceutical composition can further include one or more compatible active ingredients which are aimed at providing the composition with another pharmaceutical effect in addition to that provided by the educated mononuclear cell product. "Compatible" as used herein means that the active ingredients of such a composition are capable of being combined with each other in such a manner so that there is no interaction that would substantially reduce the efficacy of each active ingredient or the composition under ordinary use conditions. According to some embodiments, the combination therapy comprises administering to a subject in need thereof a pharmaceutical composition comprising a therapeutic amount of the educated mononuclear cell product, and a therapeutic agent effective for treating symptoms of the immune disease. For example, where the immune disease is diabetes, the therapeutic agent can be selected from the group consisting of insulin, an insulin analogue, a biguanide, a thiazolidipedione, a secretagogue, a sulfonylurea, a nonsulfonylurea secretagogue, a glinide, metformin, an alpha-glucosidase inhibitor, a meglitinide, an alpha-glucosidase inhibitor, a glucagon-like peptide 1 (GLP-1) mimetic, a glucagon-like peptide 1 (GLP-1) agonist, an amylin analogue, a dipeptidyl peptidase-4 Inhibitor, an incretin mimetic, a gastric inhibitory peptide analog, an amylin analog, a glycosuric, a finasteride, dutasteride, minoxidil, ketoconazole, spironolactone, flutamide, a cyclosporin, clobetasol, an anti-CD3 antibody, a small molecule activator of the insulin receptor, fluocinonide or a combination thereof.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which can independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although exemplary methods and materials have been described, any methods and materials similar or equivalent to those described herein can also be used in the practice or testing of the described invention. All publications mentioned herein are incorporated herein by reference to disclose and described the methods and/or materials in connection with which the publications are cited.

As used herein and in the appended claims, the singular form "a," "and," "the" include plural referents unless the context clearly dictates otherwise. The terms "comprises," "comprising," "includes," "including," "having" and their conjugates mean "including but not limited to." Terms and phrases used in this application, and variations thereof, unless otherwise expressly stated, should be construed as open ended as opposed to limiting. As examples of the foregoing, the term, "including" should be read as meaning "including, without limitation" or the like. The term, "e ample" is used to provide exemplary instances of the item in discussion, not an exhaustive or limiting list thereof. Adjectives such as e.g., "conventional," "traditional," "known" and terms of similar meaning should not be construed as limiting the item described to a given time period, or to an item available as of a given time, but, instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. The presence of broadening words and phrases such as "one or more," "at least," "such as but not limited to," or other like phrases in some instances shall not be read to mean that the narrower case is intended or required in instances, wherein such broadening phrases may be absent.

Additionally, for example any sequence(s) and/or temporal order of sequence of the system and method that are described herein this disclosure are illustrative and should not be interpreted as being restrictive in nature. Accordingly, it should be understood that the process steps may be shown and described as being in a sequence or temporal order, but they are not necessarily limited to being carried out in any particular sequence or order.

Although the described invention has been described aid illustrated herein with referred to some embodiments, it will be apparent to those of ordinary skill in the art that other embodiments may perform similar functions and/or achieve like results. Thus, it should be understood that various features and aspects of the disclosed of the disclosed embodiments can be combined with, or substituted for one another in order to form varying modes of the disclosed invention. Many different embodiments such as variations, adaptations, modifications, and equivalent arrangements thus fall within the scope and spirit of the described invention.

The publications discussed herein are provided solely for their disclosure prior to the filing date of the described invention. Nothing herein should be construed as an admission that the described invention is not entitled to antedate such publication by virtue of prior invention. Further, the dates of publication provided may be different from the actual publication dates, which may be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used but some experimental errors and deviations should be accounted for. Unless indicated otherwise, parts are by weight, molecular weight is weight average molecular weight, temperature is in degrees cent grade, and pressure is at or near atmospheric.

The Closed Loop Bioreactor Device

The closed loop bioreactor device was manufactured in a Class 100K clean room and gamma-irradiated prior to introducing the umbilical cord blood mononuclear cells. In the bioreactor device, lymphocytes separated from a patient's blood are slowly passed through the stacked discs of material with adherent umbilical cord blood mononuclear cells, and lymphocytes collected through a hole in the bottom plate are returned back to the patient. The materials used to produce the device are approved for in vivo use per the United States Pharmacopeia (i.e., Grade Class VI Plastic).

FIG. 1 illustrates a system 10 according to some embodiments of the described invention for treatment of autoimmune disorders having fluid conduit 12 for extracting blood from a patient 2, together with an apheresis apparatus 14, a stem cell bioreactor device 20 and a fluid return conduit 18. In use, blood is extracted from the subject 2 via the fluid conduit 12, e.g. with a hemodynamic pump and processed by an apheresis apparatus 14 to separate lymphocytes from the blood. The blood can be returned to the patient 2 via fluid return conduit 18. The separated lymphocytes are delivered to the bioreactor device 20, wherein portions of the lymphocyte population are modulated by interactions with the umbilical cord blood mononuclear cells within the bioreactor device 20.

Figure 2:
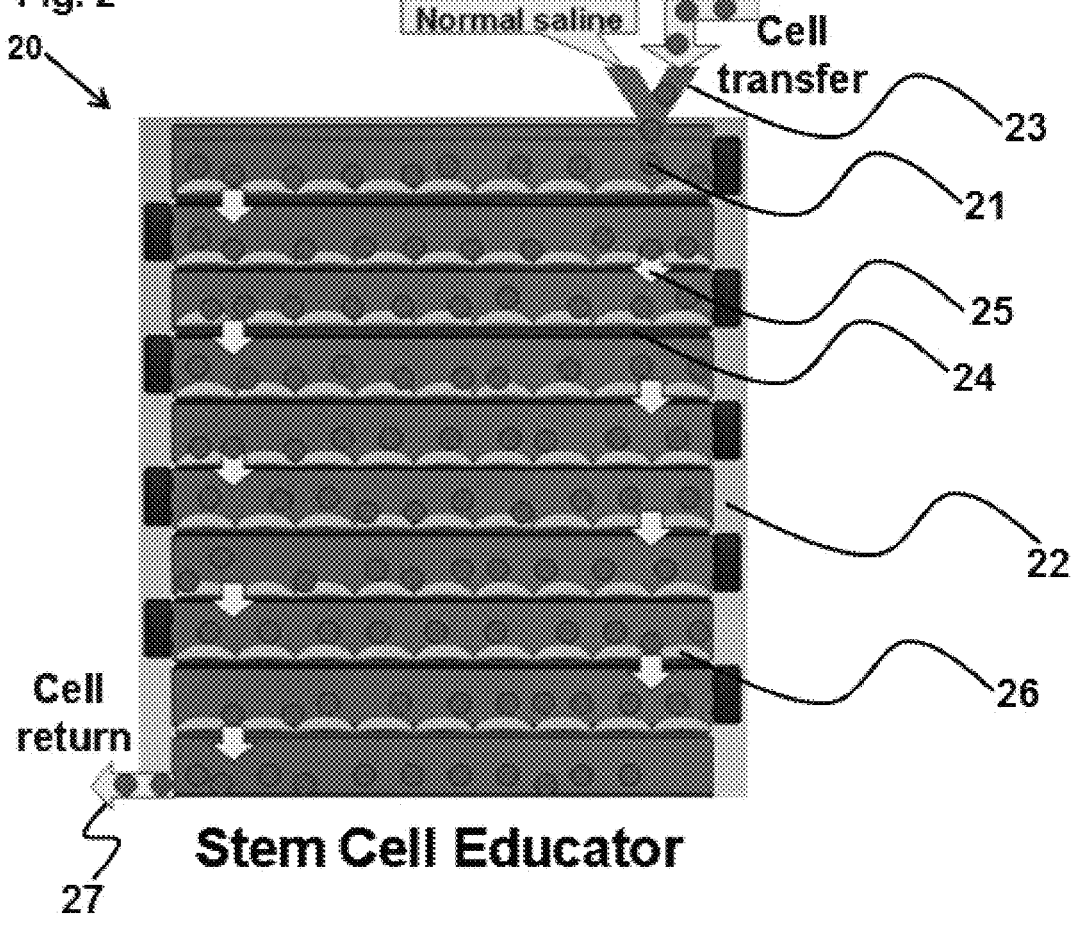
FIG. 2 is a schematic illustration of a bioreactor device for use in a system according to the invention.

FIG. 2 provides a schematic illustration of a bioreactor device 20 according to the invention including chamber 22, fluid inlet conduit 23, a plurality of substrate surface layers 24 seeded with umbilical cord blood mononuclear stem cells 26. Passage-ways 25 between the layers permit lymphocytes 21 to flow from inlet 23 to outlet 27. In use, the lymphocytes from the apheresis apparatus are fed into chamber 22 where the modulation/activation of the lymphocytes 21 occurs. After a suitable period of time, the activated and modulated lymphocytes 21 can be removed from the bioreactor device 20 and returned to the patient 2.

Example 1: Use of a Closed Loop Bioreactor Device Comprising Adherent UC-SC Cells for the Treatment of Type 1 Diabetes in Patients of Chinese Ethnicity In an open-label, phase1/phase 2 study, patients of Chinese ethnicity (N=36) with long-standing T2D were divided into three groups (Group A, oral medications, n=18; Group B, oral medications+ insulin injections, n=11; Group C having impaired s-cell function with oral medications+ insulin injections, n=7). All patients received one treatment with a device that circulates a patient's blood through a closed loop system that separates mononuclear cells from whole blood, briefly co-cultures them with adherent umbilical cord blood stem cells (UC-SCs), and returns the thus-educated autologous cells to the patient's circulation [Zhao et al., "Targeting insulin resistance in type 2 diabetes via immune modulation of cord blood-derived multipotent stem cells (CB-SCs) in stem cell educator therapy: phase I/II clinical trial", BMC Med., Vol. 11: 160, (2013)]

Clinical findings indicate that these T2D patients achieved improved metabolic control and reduced expression of inflammation markers after this treatment. Median HbA1C in Group A and B was significantly reduced from 8.61%±1.12 at baseline to 7.25%±0.58 at 12 weeks (p=2.62E-06), and 7.33%±1.02 at one year post treatment (p=0.0002). A homeostasis model assessment (HOMA) of insulin resistance (HOMA-IR) demonstrated that insulin sensitivity was improved post treatment. The islet $\beta$-cell function in Group C subjects was markedly recovered, as demonstrated by the restoration of C-peptide levels. Mechanistic studies revealed that this treatment reversed immune dysfunctions through immune modulation of monocytes and a balancing of Th1/Th2/Th3 cytokine production.

Thirty six Chinese patients with T2D have received treatment with this device in a safety study, and their results are similar to the safety evaluation with T1D participants [Zhao Y. et al., "Reversal of type 1 diabetes via islet @-cell regeneration following immune modulation by cord blood-derived multipotent stem cells", BMC Med., Vol. 10(3): 1-11, (2012)]. No participants experienced any significant adverse events during the course of treatment and post treatment for over a year. Patient complaints were limited to mild discomfort during venipunctures at the site of median cubital vein and some soreness of the arm that resolved quickly following apheresis.

Glycemic control was improved in T2D patients after treatment with this device. After receiving this therapy and being discharged from the hospital, patients continued their regular medications. Follow-up studies demonstrated that the median glycated hemoglobin (HbA1C) in Group A (n=18) and Group B (n=11) was significantly lowered from 8.61%±1.12 at baseline to 7.9%±1.2 at 4 weeks post treatment (p=0.0004), 7.25%±0.58 at 12 weeks post treatment (p=0.003) (FIG. 3a), and 7.33%±1.02 at one-year post treatment (p=0.036) in Group C patients (n=7). According to the A1C goal (<7%) recommended by the American Diabetes Association (ADA) for the treatment of adult diabetics, 28% (5/18) of subjects in Group A, 36% (4/11) of subjects in Group B, and 29% (2/7) of subjects in Group C achieved this goal at 12 weeks post treatment. More than 31% of total subjects achieved and maintained the <7% standard for over a year. Additionally, based on the efficacy criteria, 11 of 18 (61.1%) subjects in Group A, 8 of 11 (72.7%) subjects in Group B, and 4 of 7 (57.1%) subjects in Group C with reduction of A1C value (>0.5%) at 4 weeks post treatment. Thirteen of 18 (72.2%) subjects in Group A, 9 of 11 (81.8%) subjects in Group B, and 6 of 7 (85.7%) subjects in Group C with reduction of A1C value (>0.5%). A1C value in twenty eight of 36 (78%) of total subjects was reduced by 1.28±0.66 at 12 weeks post treatment.

To explore the change in insulin sensitivity, homeostasis model assessment (HOMA) of insulin resistance (HOMA-IR) the product of fasting plasma glucose and C-peptide (instead of insulin due to subjects receiving insulin injections) in Group A and B was determined. The data revealed that levels of HOMA-IR c-pep were markedly reduced at 4 weeks follow-up (FIG. 3b), which shows that insulin sensitivity had been improved post treatment. Consistent with the improved β-cell function, the median daily dose of metformin was reduced 33%-67%, and insulin was reduced 35% at 12 weeks post treatment.

Figure 3:
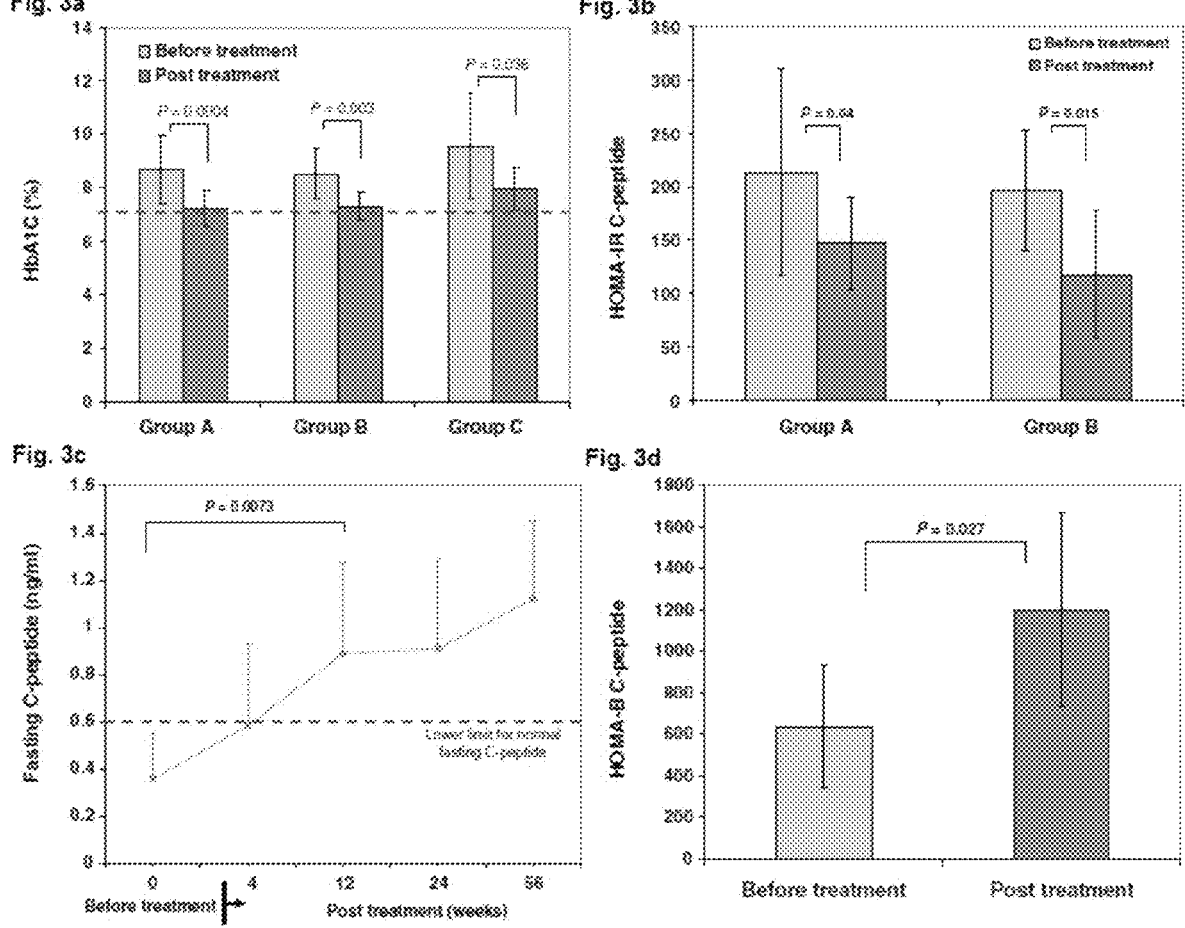
FIGS. 3a-d show improvement of metabolic control following treatment with a continuous closed loop device into which a patient's blood is circulated, mononuclear cells are separated from whole blood and briefly co-cultured in co tact with an adherent population of CB-SCs, and the educated autologous cells then returned to the patient's circulation.

Levels of fasting C-peptide were markedly increased in the long-standing T2D subjects with impaired islet β-cell function (Group C, diabetic dur tion 14±6 years, n=7, P=0.0073) (FIG. 3c). Twelve weeks after treatment, fasting C-peptide levels reached normal physiological levels and were maintained through the last follow-up for this measure (56 weeks) (0.36±0.19 ng/mL at baseline vs 1.12±0.33 ng/mL at one year post treatment, p=0.00045, FIG. 3c). β-cell functional analysis by using HOMA-B C-peptide demonstrates that the function of islet β-cells was markedly enhanced in group C subjects after receiving treatment (FIG. 3d). The data show that the restoration of C-peptide may be associated with the regeneration of islet β-cells as we demonstrated in our previous work in type 1 diabetes [Zhao Y. et al., "Reversal of type 1 diabetes via islet β-cell regeneration following immune modulation by cord blood-derived multipotent stem cells", BMC Med., Vol. 10(3): 1-11, (2012)].

Efficacy Outcomes in Correcting the Immune Dysfunction

Figure 4:
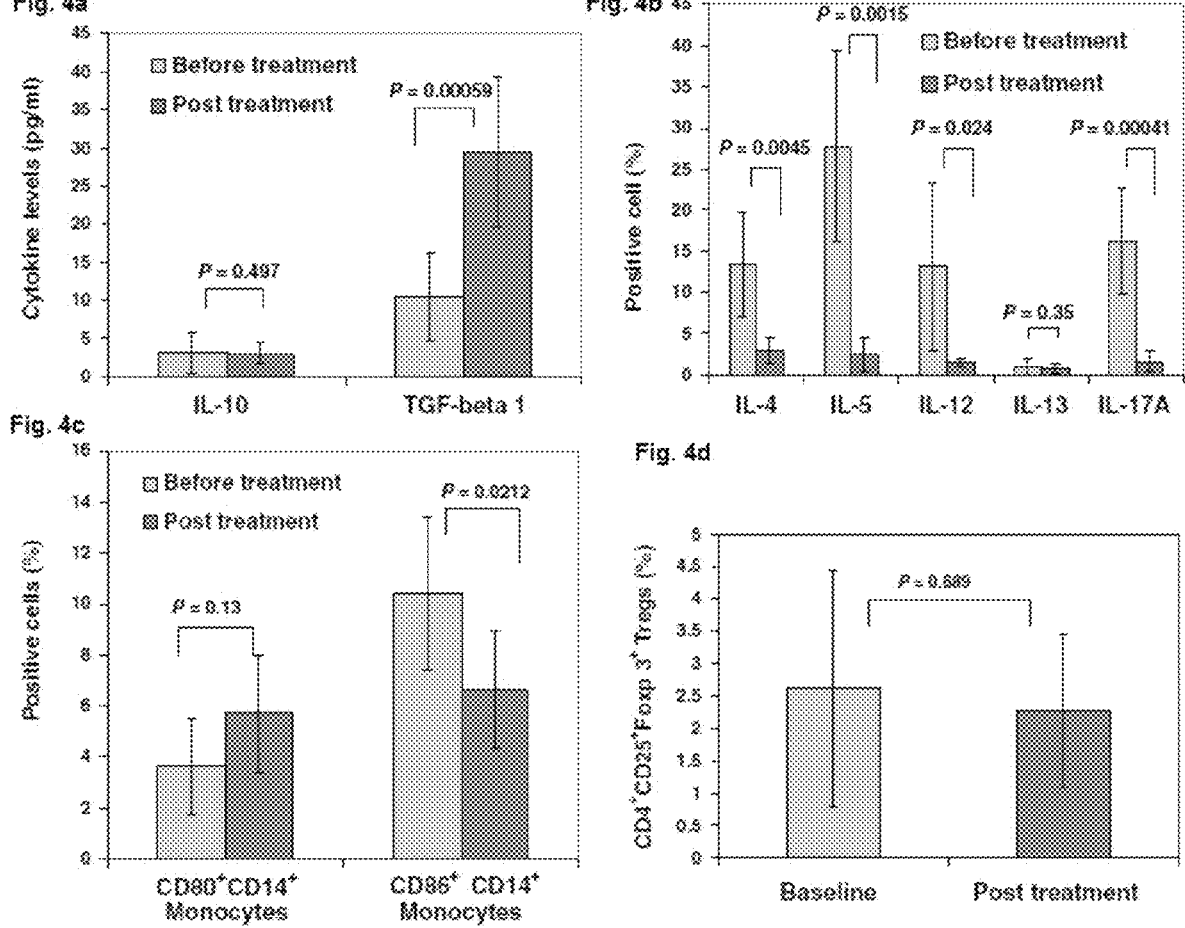
FIGS. 4a-d show anti-inflammatory effects of the treatment with the continuous closed loop device.

To determine the molecular and cellular mechanisms underlying the improvement of metabolic control, the effects of anti-inflammation and immune modulation of stem cell bioreactor device therapy in T2D were examined. ELISA was used to examine pro-inflammatory cytokines IL-1, IL-6, and TNF-α in the plasma, which are primarily involved in insulin resistance and T2D. IL-1, IL-6, a d TNF-α were all at background levels in these long-standing T2D subjects and failed to show changes after treatment (p=0.557, p=0.316, p=0.603 respectively), probably because metabolic inflammation is a chronic sub-degree inflammation [Shoelson S. E. et al., "Inflammation and insulin resistance", J Clin Invest, Vol. 116: 1793-1801, (2006)] and the serum samples which were directly collected from the blood of T2D patients, not from the lipopolysaccharide (LPS)-activated monocytes of T2D subjects [Devaraj S. et al., "Low-density lipoprotein postsecretory modification, monocyte function, and circulating adhesion molecules in type 2 diabetic patients with and without macrovascular complications: the effect of alpha-tocopherol supplementation", Circulation, Vol. 102: 191-196, (2000)]. Anti-inflammatory and immune suppressive cytokine TGF-β1 was markedly increased in the plasma of T2D subjects post treatment at 4 weeks relative to the baseline levels (FIG. 4a). However, IL-10 was unchanged in all participants (p=0.497). These findings show that up-regulation of TGF-31 is a potential mechanism contributing to the reversal of insulin resistance by this treatment.

Next, using a more sensitive intra-cellular flow cytometry analysis, interleukin-17 (IL-17, also known as IL-17A) and Th1/Th2 immune response-associated cytokines were examined in the peripheral blood of T2D subjects. IL-17A is a well-known proinflammatory cytokine involved in the auto-immune diseases. The production of IL-17, IL-12, and Th2-associated cytokine IL-4 and IL-5 were all markedly decreased after this treatment (FIG. 4b).

To explore the cellular mechanism underlying the modulation on the Th1/Th2 immune responses, we focused on the changes of co-stimulating molecules CD80/CD86 expressed on the monocytes/macrophages, the professional antigen-presenting cells that play a key role in the onset of chronic inflammation and obese-associated insulin resistance of T2D. Results demonstrated that the percentage of CD86+CD14+ monocytes was markedly decreased 4 weeks after treatment (FIG. 4c,P=0.0212). There was no significant change in the level of CD80+CD14+ monocytes (P=0.13). The ratio of CD86+CD14+ monocytes/CD80+CD14+ monocytes was reduced from 3.86±2.56 to 1.22±0.48 (P=0.01). Further flow analysis of the ligands of CD80/CD86, CD28/CTLA-4 expressed on lymphocytes revealed that the expression of CTLA-4 was markedly increased 4 weeks after receiving stem cell bioreactor device therapy (0.51%±0.5 before treatment vs 1.98%±0.51 post treat ent, P=9.02E-05). However, flow analysis failed to show differences in the expression of co-stimulating molecule CD28 (69.98%±14.17 before treatment vs 61.5%±10.89 post treatment, P=0.225). Additionally, changes in the CD4$^+$ CD25$^+$ Foxp3$^+$ Tregs population after receiving stem cell educator therapy were examined. Flow analysis did not identify any differences between baseline and 4- or 12-weeks post treatment (FIG. 4d, P=0.689). Therefore, these data show that this treatment modulates Th1/Th1 immune responses through the action of antigen-presenting cells monocytes rather than Tregs.

In Vitro Mechanistic Studies of the Immune Modulation of CB-SCs on Monocytes

Figure 5:
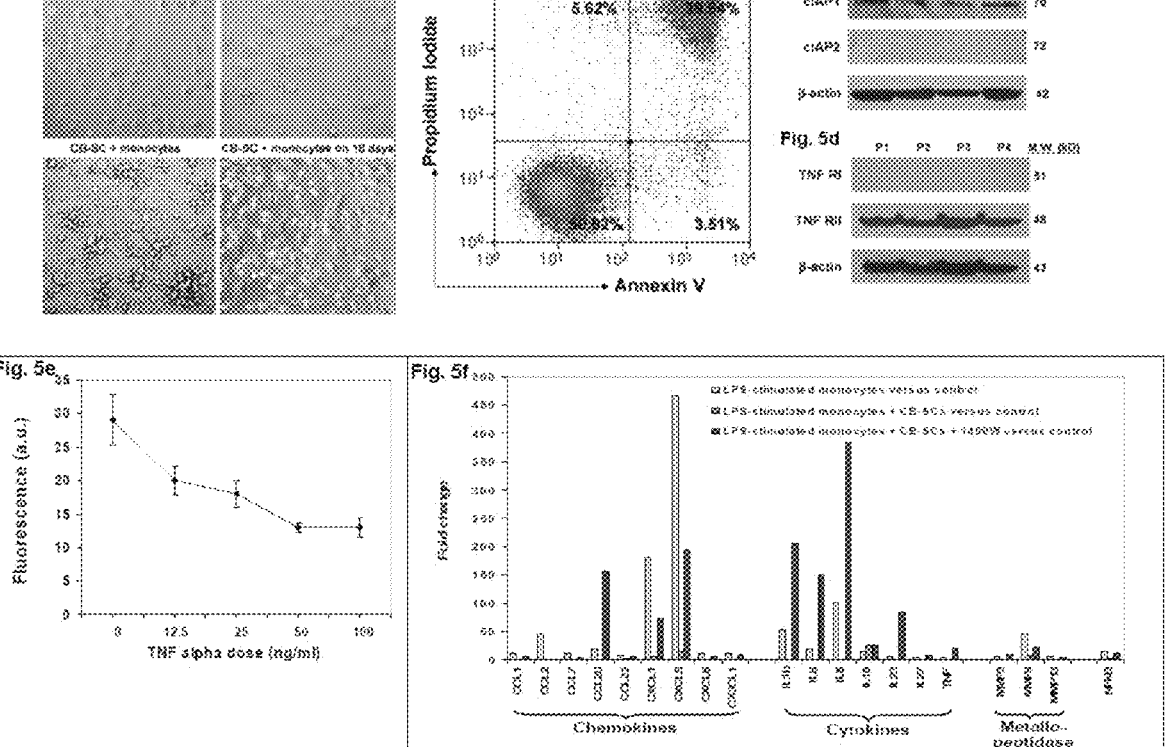
FIGS. 5a-f show in vitro study of the immune modulation of CB-SCs on monocytes.

To better understand the immune modulation effect of CB-SC on monocytes, in vitro co-culture experiments using CD14$^+$ monocytes purified from human peripheral blood were performed. Purified CD14$^+$ monocytes were co-cultured with CB-SCs at different ratios. There were strong reactions after adding the CD 4+ monocytes to CB-SCs (FIG. 5a, bottom left panel). Flow analysis demonstrated that co-culture with CB-SCs for 18 hours resulted in the significant apoptosis of monocytes at the ratio 1:5 of CB-SC: monocytes (FIG. 5b). Correspondingly, both cell viability and attachment of CB-SCs were also affected by the presence of apoptotic monocytes (FIG. 5a, bottom left panel). Structurally, the cellular processes of CB-SCs were reduced in length, but most were still attached to the bottom (FIG. 5a, bottom left panel). These impaired CB-SCs were restored after co-culture for 2-3 days; they continually expanded and became 90~100% confluent after 7-10 days (FIG. 5a, bottom right panel). Mechanistic studies revealed that CB-SCs displayed the cellular inhibitor of apoptosis protein (cIAP) 1 that protects CB-SCs against the cytotoxic effects of monocytes, allowing them to survive and proliferate (FIG. 5c). We found that CB-SCs expressed tumor necrosis factor receptor II (TNF R II) but not TNF R I (FIG. 5d). Recombinant TN showed cytotoxicity to CB-SCs at different doses (FIG. 5e). CB-SCs pre-treated with TNF RII mAb (20 µg/mL) at ratio of 1:10 markedly blocked the toxic action of monocytes and protect 50% of CB-SCs with good cell viability and morphology.

To further explore the immune modulation effect by CB-SCs on monocytes, lipopolyssacharide (LPS)-stimulated purified CD14$^+$ monocytes were co-cultured with CB-SCs. Real time PCR array showed that co-culture with CB-SC could significantly down-regulate numbers of LPS-stimulated, inflammation-related genes including chemokines, multiple cytokines, and matrix metallopeptidase, along with signaling pathway molecule NF-κB (FIG. 5f). These data demonstrate that in vitro co-culture of monocytes with CB-SCs causes substantial down-regulation of inflammation-associated gene expressions in monocytes.

Previous work had shown that CB-SCs function as immune modulators on lymphocytes via nitric oxide (NO)

production [Zhao Y. et al., "Immune regulation of T lymphocyte by a newly characterized human umbilical cord blood stem cell", Immunol Lett, Vol. 108: 78-87, (2007)]. To determine whether NO is involved in the immune modulation of CB-SCs on monocytes, the specific inducible nitric oxide synthase (iNOS) inhibitor 1400W was applied to the co-culture system. The data demonstrated that the inhibitory effects of CB-SC on LPS-stimulated monocytes could be significantly reversed in the presence of iNOS inhibitor 1400W (FIG. 5*f*). Blocking NO production in CB-SCs could markedly increase the expression of chemokine CCL20 and cytokines (e.g., IL-1α, IL-6, IL-8, IL-23, and TNF-α) in monocytes. These results show that CB-SC-derived NO plays an essential role in the immune modulating and anti-inflammatory effects of CB-SCs on monocytes.

Example 2: Use of a Closed Loop Bioreactor Device Comprising Adherent UC-SC Cells for the Treatment of Type 1 Diabetes in Patients of Caucasian Ethnicity To evaluate the immune modulating effects of the closed loop bioreactor device comprising adherent UC-SC cells for the treatment of type 1 diabetes in patients of Caucasian ethnicity, a phase 1/2 clinical trial was conducted in 15 subjects with established T1 D.

T1D patients receiving care at the Endocrinology and Nutrition Service, Hospital Universitario Central de Asturias (Oviedo, Spain) were enrolled in this phase 1/phase 2, open-label clinical trial conducted from Nov. 27, 2012 through Oct. 1, 2014. The principal investigator designed the clinical trial and received ethical approval for the clinical treatment protocol and consent form from Regional Committee for Clinical Research Ethics and the Comisión Permanente de Trasplantes del Consejo Interterritorial del Sistema Nacional de Salud. A signed informed consent was obtained from each participant. The clinical trial was conducted in 15 subjects with established T1D (Table 1A; Group A T1D patients with residual islet β-function and Table 1B; Group B T1D patients with no residual islet β-function). Subjects were qualified for recruitment, as shown in the Diagram flow chart 1 of the phase 1/2 clinical trial below, and if they met the 2012 diagnosis standards of the American Diabetes Association (ADA) and if a blood test indicated the presence of at least one autoantibody to pancreatic islet β-cells. Key exclusion criteria included clinically significant liver (AST or ALT 2≥x upper limit of normal), kidney (creatinine≥2.0 mg/dl), or heart disease; pregnancy or breastfeeding mothers; immunosuppressive medication; known active infection with viral diseases; or diseases associated with immunodeficiency; or hemoglobin<10 g/dL or platelets<100 k/mL; use of immunosuppressive medication within one month.

Table 1A shows the characteristics of the enrolled Caucasian type 1 diabetes patients before treatment in the phase 1/2 clinical trial. Group A: T1D patients with residual islet β-cell function.

| Patient No. | Age | Gender | History (Year) | Fasting C-peptide (ng/mL) | Post-glucagon C-peptide (ng/mL) | HbA$_1$C(%) | Insulin dose (U/kg body weight) |
|---|---|---|---|---|---|---|---|
| 1 | 36 | M | 1 | 0.77 | 1.06 | 7.1 | 0.28 |
| 2 | 27 | F | 1 | 0.54 | 0.57 | 6.3 | 0.32 |
| 3 | 31 | F | 10 | 0.25 | 0.4 | 9 | 0.52 |
| 4 | 20 | M | 3 | 1.05 | 2.18 | 6.2 | 0.18 |
| 5 | 37 | M | 14 | 0.26 | 0.36 | 7.8 | 0.4 |
| 6 | 52 | M | 10 | 0.23 | 0.27 | 9.2 | 0.61 |
| Mean (SD) | 33.8 (10.9) | | 6.5 (5.5) | 0.52 (0.34) | 0.81 (0.73) | 7.6 (1.3) | 0.38 (0.16) |

TABLE 1B shows the characteristics of the enrolled Caucasian type 1 diabetes patients before treatment in the phase 1/2 clinical trial. Group B: T1D patients with no residual islet β-cell function.

| Patient No. | Age | Gender | History (Year) | Fasting C-peptide (ng/mL) | Post-glucagon C-peptide (ng/mL) | HbA$_1$C(%) | Insulin dose (U/kg body weight) |
|---|---|---|---|---|---|---|---|
| 7 | 30 | M | 23 | <0.01 | <0.01 | 7.1 | 0.62 |
| 8 | 37 | M | 15 | <0.01 | <0.01 | 6.2 | 0.72 |
| 9 | 40 | F | 12 | <0.01 | <0.01 | 8.4 | 0.92 |
| 10 | 53 | F | 14 | <0.01 | <0.01 | 9.1 | 0.79 |
| 11 | 33 | M | 13 | <0.01 | <0.01 | 7.4 | 0.56 |
| 12 | 48 | F | 6 | <0.01 | 0.04 | 10.1 | 0.58 |
| 13 | 32 | M | 6 | <0.01 | 0.01 | 8.3 | 0.51 |
| 14 | 45 | M | 17 | <0.01 | <0.01 | 6.5 | 0.71 |
| 15 | 45 | M | 6 | 0.02 | 0.06 | 8.4 | 0.96 |
| Mean (SD) | 40.3 (7.9) | | 12.4 (5.8) | 0.01 (0.003) | 0.02 (0.02) | 7.9 (1.3) | 0.71 (0.16) |

Treatment and Follow-Up

All participants in this study received two treatments with the closed loop bioreactor comprising adherent UC-SC cells (Tianhe Stem Cell Biotechnology®, USA). The preparation of CB-SC cultures and the closed loop devices were performed as previously described [Zhao Y. et al., "Reversal of type 1 diabetes via islet beta cell regeneration following immune modulation by cord blood-derived multipotent stem cells", BMC Med, Vol. 10:3, (2012)]. Briefly, human cord blood units derived from healthy allogeneic donors were obtained from Centro Comunitario de Sangre y Tejidos de Asturias (CCST, Oviedo, Spain). All cord blood samples were screened for HIV I&II, HBsAg, HBcAg, HCV, HIVNAT, STS, HBVNAT, HCVNAT, HTLV I/II, West Nile, Chagas, and CMV, and only pathogen-free cord blood units were used for clinical treatment. The human CB-SCs were isolated from fresh cord blood unit (at least 100 mL/unit). This was done by taking 50 mL tubes and they were put in holders. Three mL HISTOPAQUE®-1077 was added to each tube, (20 mL conical centrifuge tubes) and brought to room temperature to isolate the CB-SCs. Three mL of whole blood was carefully layered onto the HISTOPAQUE®-1077. Centrifugation was done at 400×g for 30 minutes at room temperature. After centrifugation, the upper layer was aspirated to within 0.5 cm of the opaque interface containing the CB-SCs. The opaque interface was transferred in a new clean 20 mL conical tube. The cells were washed with 10 mL isotonic phosphate buffered saline solution. After washing which as done by mixing and centrifuging at 250×g for minutes, the supernatant was discarded and after washing two more times, the CB-SCs were resuspended in 0.5 mL isotonic phosphate buffered saline solution. Human CB-SCs were produced and the cord blood mononuclear cells were plated in 150×15 mm Petri dishes (Becton Dickinson Labware, Franklin Lakes, NJ, not tissue culture-treated dishes) at a density of at least $1×10^6$ cells/mL, 25 mL/dish in RPMI 1640 medium and incubated at 37° C. in 8% $CO_2$. Cord blood mononuclear cells were plated in bioreactor devices in serum-free culture medium (Lonza, Walkersville, MD) and incubated at 37° C., in 8% $CO_2$ for about 2-3 weeks. CB-SC cells were observed for being round and further verified for attachment on the bottom of the Petri dishes. After 2-3 weeks, the CB-SCs were co-cultured with isolated MNCs via apheresis. CB-SCs growing at 80% confluence (about $1×10^7$ cells/device) were prepared for the clinical trial. One bioreactor device was generated from one cord blood unit, and used for one subject at one treatment.

Figure 6:
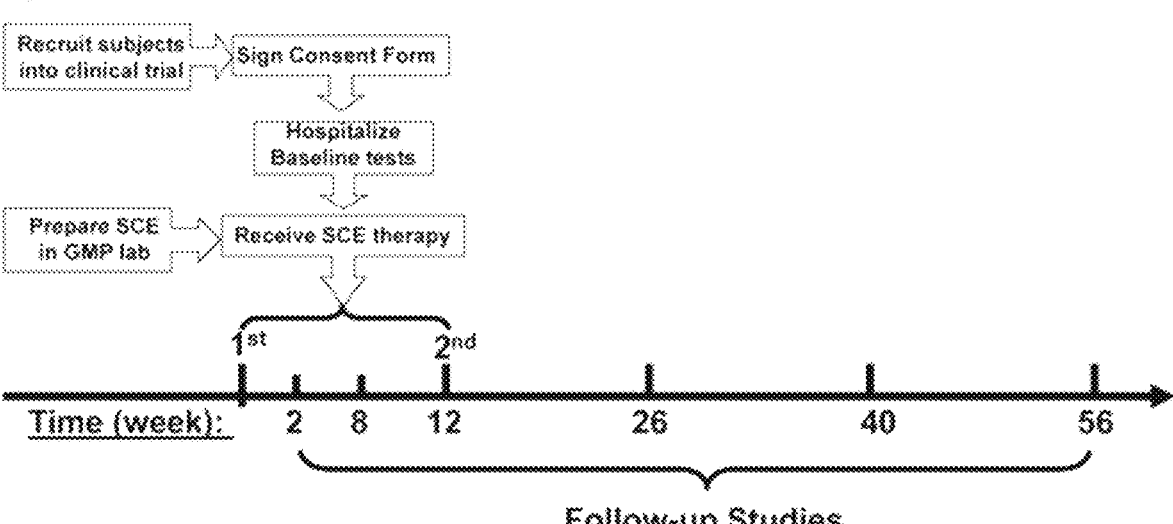
FIG. 6 illustrates the treatment regime for treatment with the discontinuous stem cell education (SCE) system and follow-up studies in Caucasian T1D subjects in a phase 1/2 clinical trial.

For the bioreactor device therapy a 16-gauge IV needle was placed in the left or right median cubital vein, and the patient's blood was passed through a Blood Cell Separator MCS+(Haemonetics®, Braintree, MA) to isolate the mononuclear cells. For a single session of MNC collection by apheresis, approximately 10 L of blood was processed from each enrolled subject within 6-7 hours, with the collection of about $1×10^{10}$ MNCs. The isolated mononuclear cells were transferred into the bioreactor device for continuous treatment with allogeneic CB-SCs, and other blood components were automatically returned to the patient's circulation. In the bioreactor device, MNC isolated from the patient's peripheral blood were slowly passed through the stacked discs with adherent CB-SCs at a CB-SC:MNC ratio of 1:20, at a ratio of 1:30, at a ratio of 1:40 or at a ratio of 1:50. After contact for 2-3 h, CB-SC-treated mononuclear cells were returned to the patient's blood circulation via a dorsal vein in the hand with physiological saline. It took 8-9 hours. Patients were hospitalized for one day to monitor temperature and conduct blood count tests for adverse reactions following treatment. After 3 months, all subjects received a 2nd treatment with bioreactor device therapy, as described above. Follow-up visits were scheduled 2, 8, 12, 18, 26, 40 and 56 weeks after treatment for clinical assessments and laboratory tests (FIG. 6).

To evaluate β-cell function, fasting and glucagon-stimulated C-peptide levels were examined at baseline and after treatment the closed loop bioreactor device comprising adherent UC-SC cells. The glucagon-stimulated C-peptide test was performed. A sample of 5-10 mL venous blood was withdrawn from each subject in the fasting state for baseline C-Peptide measurement. The glucagon test was performed by injecting 1 mg glucagon intravenously, followed 6 min later by a second blood-draw of 5-10 mL from a separate venous site. The selection of subjects for the glucagon test was based simply on their agreement to have the test done.

After centrifugation of the blood samples, the sera were isolated and then frozen at −20° C.

The primary study end points were feasibility and safety of the closed loop treatment through 56 weeks post-treatment and preliminary evaluation of the efficacy of the therapy for changing immune markers in T1D subjects. The secondary study end point was preliminary evidence for efficacy of the therapy in the improvement of β-cell function. Baseline blood samples were collected prior to closed loop treatment.

Mixed Lymphocyte Reactions (MLR) and Ex-Vivo Co-Cultures

Human buffy coat blood units were purchased from the Blood Center of New Jersey (East Orange, NJ). CB-SCs were harvested as previously described [Zhao Y. et al., "Reversal of type 1 diabetes via islet β-cell regeneration following immune modulation by cord blood-derived multipotent stem cells", BMC Med., Vol. 10(3), 1-11, (2012)]; [Zhao Y. et al., "Targeting insulin resistance in type 2 diabetes via immune modulation of cord blood-derived multipotent stem cells (CB-SCs) in stem cell educator therapy: phase I/II clinical trial", BMC Med., Vol. 11: 160, (2013)]. This was done by taking 50 mL tubes and they were put in holders. Three mL HISTOPAQUE®-1077 was added to each tube, (20 mL conical centrifuge tubes) and brought to room temperature to isolate the CB-SCs. Three mL of whole blood was carefully layered onto the HISTOPAQUE®-1077. Centrifugation was done at 400×g for 3 minutes at room temperature. After centrifugation, the upper layer was aspirated to within 0.5 cm of the opaque interface containing the CB-SCs. The opaque interface was transferred in a new clean 20 mL conical tube. The cells were washed with 10 mL isotonic phosphate buffered saline solution. After washing which was done by mixing and centrifuging at 250×g for minutes, the supernatant was discarded and after washing two more times, the CB-SCs were resuspended in 0.5 mL isotonic phosphate buffered saline solution. To examine the immune modulating effects of CB-SCs on T cells via the mixed leukocyte reactions (MLR), responder cells were co-cultured with allogeneic stimulator cells irradiated at 3000 rad at the R:S ratio of 1:2, in the presence or absence of CB-SCs. The ratio of CB-SCs: responder was 1:10. After 4-5 days of co-culture, cells were photographed with an Olympus IX71 inverted microscope and collected for flow analysis.

To analyze the CCR7 expression on CD45RO+CD62L− $T_{EM}$ cells, adult peripheral blood-mononuclear cells (PBMCs) were co-cultured with CB-SCs at the CB-SCs: PBMCs ratio of 1:10 in serum-free culture medium (Lonza, Walkersville, MD) and incubated at 37° C., in 8% $CO_2$. The untreated PBMCs served as control. The CB-SC-treated PBMCs were collected for flow cytometry at 24 and 48 hours respectively.

To perform ex vivo studies, human cord blood units were provided by Cord: Use Cord Blood Bank (Orlando, FL). Only pathogen-free cord blood units were used for isolating CB-SCs. The human CB-SCs were isolated from fresh cord blood unit (at least 100 mL/unit). This was done by taking 50 mL tubes and they were put in holders. Three mL HISTOPAQUE®-1077 was added to each tube, (20 mL conical centrifuge tubes) and brought to room temperature to isolate the CB-SCs. Three mL of whole blood was carefully layered onto the HISTOPAQUE®-1077. Centrifugation was done at 400×g for 30 minutes at room temperature. After centrifugation, the upper layer was aspirated to within 0.5 cm of the opaque interface containing the CB-SCs. The opaque interface was transferred in a new clean 20 mL conical tube. The cells were washed with 10 mL isotonic phosphate buffered saline solution. After washing which was done by mixing and centrifuging at 250×g for minutes, the supernatant was discarded and after washing two more times, the CB-SCs were resuspended in 0.5 mL isotonic phosphate buffered saline solution. Human CB-SCs were produced and the cord blood mononuclear cells were plated in 150×15 mm Petri dishes (Becton Dickinson Labware, Franklin Lakes, NJ, not tissue culture-treated dishes) at a density of at least $1\times10^6$ cells/mL, 25 mL/dish in RPMI 1640 medium and incubated at 37° C. in 8% $CO_2$. Cord blood mononuclear cells were plated in bioreactor devices in serum-free culture medium (Lonza, Walkersville, MD) and incubated at 37° C., in 8% $CO_2$ for about 2-3 weeks. CB-SCs were observed for being round and further verified for attachment on the bottom of the Petri dishes. CB-SCs growing at 80% confluence (about $1\times10^7$ cells/device) were prepared for co-culture with allogeneic lymphocytes.

In preparation for the clinical trial, peripheral blood samples (10 mL per subjects) were obtained from patients before the treatment and at 2, 8, 18, 26 and 56 weeks respectively post-treatment. Cells were incubated with mouse anti-human mAbs (BioLegend, San Diego, CA), including PerCP/Cy5.5-conjugated anti-CD3, PerCP/Cy5.5-conjugated anti-CD4, PE-conjugated anti-CD8, FITC-conjugated anti-CD45RA, PE-conjugated anti-CD45RO, PE-conjugated anti-CD56, APC-conjugated anti-CCR7. To test the percentage and absolute cell numbers of different subsets in peripheral blood, cells were immunostained with BD MultiTEST reagents CD3 FITC/CD8 PE/CD45 PerCP/CD4 APC and CD3 FITC/CD16+CD56 PE/CD45 PerCP/CD19 APC (BD Biosciences, San Jose, CA). Isotype-matched mouse anti-human IgG antibodies (Beckman Coulter) served as a negative control for all fluorescein-conjugated IgG mAb. After staining, cells were collected and analyzed using a BD FACScalibur™ Cytometer. The final data were analyzed using the CellQuest Pro Software (Becton Dickinson, MD).

For ex vivo studies, flow cytometric analyses, cells were stained for 30 minutes at room temperature and then washed with PBS prior to flow analysis. We used several mouse anti-human monoclonal Abs (mAbs), including APC-AF 750-conjugated anti-CD4, APC-AF 750- or Krome Orange-conjugated anti-CD8, PE- or FITC-conjugated anti-CD45RA, FITC-conjugated anti-CD45RO, ECD-conjugated anti-CD62L, and PE-Cy7-conjugated anti-CCR7. Isotype-matched mouse anti-human IgG antibodies (Beckman Coulter) served as a negative control for all fluorescein-conjugated IgG mAb. After staining, cells were collected and analyzed using a Gallios Flow Cytometer (Beckman Coulter), equipped with 3 lasers (488 nm blue, 638 red, and 405 violet lasers) for the concurrent reading of up to 10 colors. The final data were analyzed using the Kaluza Flow Cytometry Analysis Software (Beckman Coulter).

An intention-to treat approach was used, with 15 patients undergoing treatment with the closed loop bioreactor device comprising adherent UC-SC cells. All participants were included in safety analyses. The feasibility of the treatment was assessed by analyzing the number of the patients unable to complete the therapy and the number of patients who were lost to follow-up prior to the 12-month visit. The primary efficacy end points were the change in immune markers between baseline and follow-ups. Statistical analyses of data were performed by the two-tailed paired Student's t-test to determine statistical significance between baseline and follow-ups. Values were given as mean±SD (standard deviation).

Results

Safety Profile and Feasibility of Two Treatments with Bioreactor Device Therapy in Caucasian T1D Subjects In previous clinical trials, all subjects received one treatment [Zhao Y. et al., "Reversal of type 1 diabetes via islet R-cell regeneration following immune modulation by cord blood-derived multipotent stem cells", BMC Med., Vol. 10(3), 1-11, (2012)]; [Zhao Y. et al., "Targeting insulin resistance in type 2 diabetes via immune modulation of cord blood-derived multipotent stem cells (CB-SCs) in stem cell educator therapy: phase I/II clinical trial", BMC Med, Vol. 11: 160, (2013)]. Due to the likelihood that significant numbers of pathogenic autoimmune cells may have remained in lymph nodes and other tissues, failing to enter into the bloodstream during the procedure, and thus may have escaped the exposure to CB-SCs, a second treatment was added three months following the initial session in these T1D subjects (n=15). No participants experienced any significant adverse events during the course of the two treatments with bioreactor device therapy or during 56-week follow-up. During the procedure, only mild discomfort at the site of venipuncture (the median cubital vein) and some soreness of the arm were noted for some participants. No fever or rejection was noted during follow-up studies.

Clinical Efficacy of Closed Loop Treatment in the Modulation of Memory T Cell Compartment of Caucasian Subjects To evaluate the immune modulating effects of the closed loop treatment, flow cytometry was used to examine immune markers in the 15 participants following the closed loop treatment. Clinical data indicated no changes in total cell numbers of each cell population during one-year follow-up, including leukocyte common antigen CD45+ nuclearized cells, CD3$^+$ T cells, CD4$^+$ T cells, CD8$^+$ T cells, CD56+NK cells, and CD20$^+$ B cells (FIG. 7a). Quantification of the percentages of total CD4$^+$ and CD8$^+$ T cells in peripheral blood remained very stable over a year (FIG. 7b).

The modulating effect of closed loop treatment on different T-cell subpopulations was explored using the common surface markers for characterization of naive and memory T cells, such as CD45RA and CCR7. The percentage of naive CD4$^+$ T (CD45RA$^+$ CCR7$^+$) cells was significantly increased at 26 weeks after the closed loop treatment (P=0.0042), and maintained through the final follow-up (at 56 weeks post-treatment, P=0.0021) (FIG. 7c). The percentage of naive CD8+ T cells did not exhibit significant changes at any follow-ups (FIG. 7c). These findings suggested that SCE therapy restored the regeneration of naive CD4$^+$ T cells, an essential part of normal immune capacity.

To explore the effects of closed loop treatment on memory T cells, central memory T cells and effector memory T cells ($T_{CM}$ and $T_{EM}$, respectively) were examined by flow cytometry. Overall analysis in these subjects demonstrated that the percentage of CD4$^+$ $T_{CM}$ (CD45RA-CCR7$^+$) cells was markedly and constantly increased after receiving bioreactor device therapy at 18 weeks (P=0.018) (FIG. 7d). In contrast, the percentage of CD8+ T cells was only temporarily improved at 18 weeks (P=0.034), but return to baseline levels during continued follow-ups (FIG. 7d). In comparison with Group B subjects (4/9, 44%), the percentage of CD4+ $T_{CM}$ cells in Group A subjects (4/6, 67%) more efficiently increased to over 30% of positive cells at 18 weeks follow-up (data not shown). Overall analysis of $T_{EM}$ (CD45RA$^+$ CCR7$^-$) cells revealed that both CD4$^+$ cells and CD8$^+$ T cells were considerably decreased at 18 weeks (P=0.03) and 26 weeks (P=0.0024) respectively (FIG. 7e). The percentage of CD8+ T cells in Group A subjects (6/6, 100%) more efficiently decreased over 15% of positive cells compared to Group B subjects (7/9, 78%) at 26 weeks follow-up; 5/6 (83%) of Group A subjects vs 7/9 (78%) of Group B subjects for the reduction of CD4+ T cells at 26 weeks follow-up (data not shown). In addition, using HLA$^-$DR as an activation marker for T cells, clinical data demonstrated that the percentage of CD4$^+$ HLA$^-$DR$^+$ T cells and CD8*HLA$^-$DR$^+$ T cells were markedly declined at 26 weeks follow-up relative to the baseline levels (P=0.002 and P=0.006 respectively) (FIGS. 7f and g).

Figure 8A:
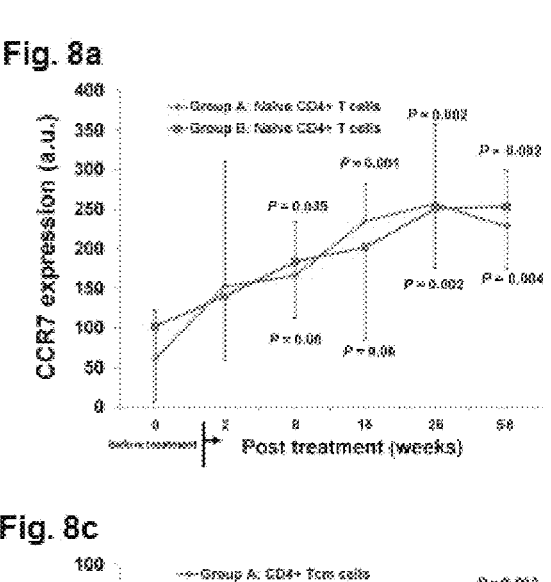
FIGS. 8*a-e* show up-regulation of CCR7 expression on Tcells in Caucasian T1D patients after SCE treatment in the phase 1/2 clinical trial. All subjects received two treatments with SCE device therapy: the first treatment was at t=0, with the second treatment after three months. Follow-up visits were scheduled 2, 8, 12, 18, 26, 40 and 56 weeks after treatment for clinical assessments and laboratory tests. Patient lymphocytes were isolated from peripheral blood by Ficoll-Hypaque ($\gamma$=1.077) for flow cytometry analyses in T1D patients at baseline and different time points after SCE device therapy. Isotype-matched IgG served as control. The lev Is of CCR7 expression were analyzed by Kaluza Flow Cytometry Analysis Software and present as arbitrary unit (a.u.).
Figure 8B:
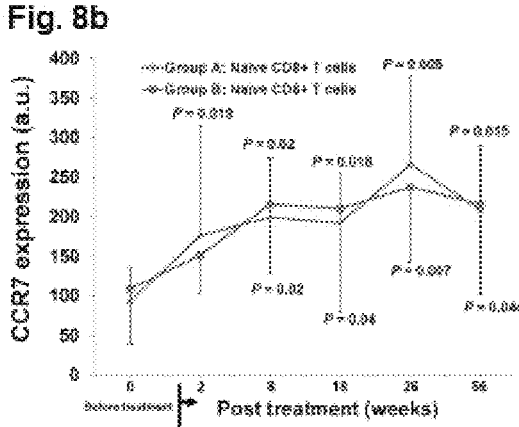
Figure 8C:
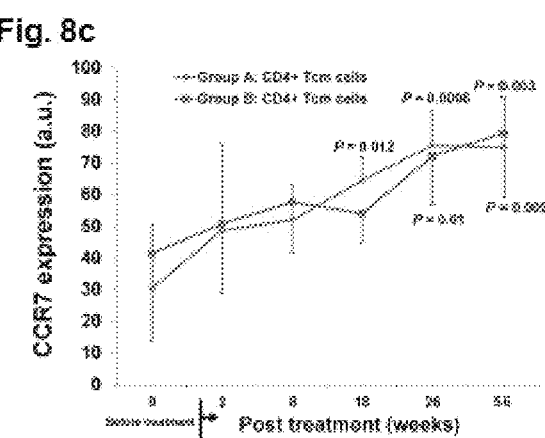
Figure 8D:
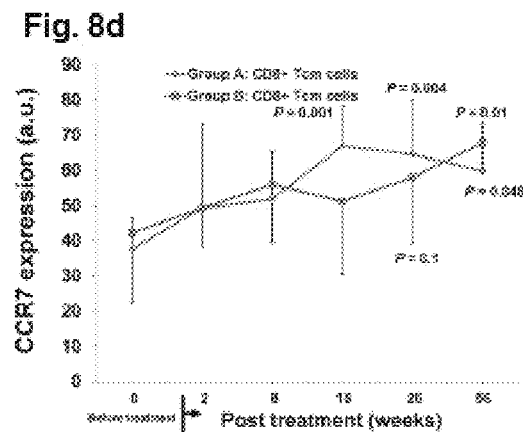
Figure 8E:
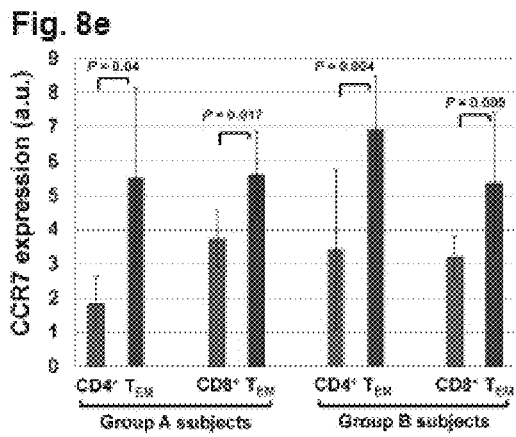

Up-Regulation of CCR7 Expression on T Cells after Closed Loop Treatment in Caucasian T1D Subjects C-C chemokine receptor 7 (CCR7) plays important roles in lymph-node homing of T cells via high endothelial venules and mediating T-cell homeostasis [Forster R. et al., "CCR7 and its ligands: balancing immunity and tolerance", Nat Rev Immunol, Vol. 8: 362-371, (2008)]; [Moschovakis G. L. et al., "Multifaceted activities of CCR7 regulate T-cell homeostasis in health and disease", Eur J Immunol, Vol. 42: 1949-1955, (2012)]. To further explore the immunomodulating effect of the closed loop treatment, the level of CCR7 expression on naïve T, $T_{CM}$, and $T_{EM}$ cells was analyzed by flow cytometry. Clinical data revealed that both Group A and B subjects significantly increased the expression of CCR7 on naïve CD4$^+$ T cells (FIG. 8a) naïve CD8+ T cells (FIG. 8b) and CD4$^+$ T cells (FIG. 8c). The marked responses of Naïve CD4+ T cells in Group A subjects happened as early as at 8 weeks post closed loop treatment, comparable to that of delayed responses in Group B subjects at 26 weeks (FIG. 8a). The up-regulation of CCR7 expression on naïve CD8+ T cells was shown simultaneously at 8 weeks follow-up in both Group A and B subjects (FIG. 8b). The expression of CCR7 on CD8+ T cells in Group A subjects was also improved and started at 18 weeks follow-up (FIG. 8d), but with a postponed response in Group B subjects at 56 weeks follow-up (P=0.046, FIG. 8d). The levels of CCR7 expression on both CD4+T and CD8+ T cells were markedly enhanced at 56 weeks follow-up after receiving stem cell bioreactor device therapy in both groups (FIG. 8e). The data show that the up-regulation of CCR7 expression on CD4+ and CD8$^+$ T cells may lead to the re-distribution of T cells in T1D subjects after the closed loop treatment.

Up-Regulation of CCR7 Expression on T Cells by Ex Vivo Studies after Closed Loop Treatment with CB-SCs CCR7 is a critical marker for the characterization of different T-cell subpopulations, which expression can be modulated by multiple factors (Britschgi et al., 2008). To further demonstrate the up regulation of CCR7 on naïve T, $T_{CM}$ and $T_{EM}$ cells, the mixed leukocyte reaction (MLR) was employed to in the presence or absence of CB-SCs. Phase contrast microscopy revealed significant numbers of cell clusters of varying sizes floating in the supernatant in the absence of CB-SC (FIG. 9a, left panel), but not in the presence of CB-SC (FIG. 9a, right panel). This indicated the suppressive activity of CB-SCs on the proliferation of T cells. Flow cytometry showed that the overall levels of CCR7 expression on CD4+ and CD8$^+$ T cells were increased after the treatment with CB-SCs (FIG. 9b).

CCR7 expression on gated CD4$^+$ T cells was further analyzed. In comparison with CB-SC-untreated groups (responder only or responder+stimulator), both percentage and mean fluorescence intensity (MFI) of CCR7 expression were enhanced on naïve T (CD45RA$^+$ CCR7$^+$) cells in the CB-SC-treated groups (responder+stimulator+CB-SCs or responder+CB-SCs) (FIG. 9c, left panels). The percentage of $T_{CM}$ cells (CD45RO$^+$ CCR7$^+$) was increased in the CB-SC-treated groups. By contrast, the percentage of $T_{EM}$ cells (CD45RO$^+$ CCR7$^-$) was decreased in the CB-SC-treated groups (FIG. 9c, right panels). The mean fluorescence intensity of CCR7 expression on $T_{EM}$ cells (CD45RO$^+$ CCR7$^-$) was up-regulated from 1.85±0.07 in the CB-SC-untreated groups to 2.24±0.01 in the CB-SC-treated groups (P=0.017).

To further confirm the up-regulation of CCR7 expression on $T_{EM}$ cells, another major lymph node homing receptor CD62L was applied as a marker for human $T_{EM}$ cells (CD45RO$^+$ CD62L$^-$) [Lefrancoi et al., Immunol. Rev., Vol. 211: 93-103, (2006)]. After treatment with CB-SCs, the level of CCR7 expression was analyzed on the gated CD45RO+ CD62L$^-$ $T_{EM}$ cells. The data demonstrated that the mean fluorescence intensity of CCR7 expression on CD45RO$^+$ CD62L$^-$ $T_{EM}$ cells was upregulated from the baseline level 1.87±0.04 to 2.09±0.07 after the treatment with CB-SCs (P=0.02).

Therefore, these data show that the CCR7 expression on $T_{EM}$ cells can be modulated by the treatment of CB-SCs.

Clinical Efficacy of Stem Cell Bioreactor Device Therapy in the Improvement of Pancreatic β-Cell Function of Caucasian Subjects To test the therapeutic potential of stem cell bioreactor device therapy in the metabolic control of Caucasian T1D subjects, islet β-cell function was examined through the measurement of fasting plasma C-peptide and glucagon-stimulated C-peptide levels. In Group A subjects, clinical results demonstrated up-regulation of both fasting and glucagon-stimulated C-peptide levels at 12 weeks in two recent-onset T1D subjects (i.e., those most likely to have residual β-cell populations) (FIGS. 10a and b). Recovered fasting and glucagon-stimulated C-peptide levels were retained in subject 1 through the final follow-up at 56 weeks post-treatments (FIG. 10a). Glucagon-stimulated C-peptide levels in subject 2 were stable during one-year follow-up, while fasting C-peptide levels declined slightly (FIG. 10b). Subject 3 who had T1D 10 years at the time of study, still achieved modest improvements including an increase in fasting C-peptide from 0.25 ng/mL at basal to 0.36 ng/mL at 56 weeks and an increase in glucagon-stimulated C-peptide level from 0.4 ng/mL at basal to 0.52 ng/mL at 26 weeks (FIG. 10c). Subject 4 who had T1D 3 years at the time of the study, retained normal β-cell function with no significant change over time in fasting C-peptide levels from 1.05 ng/mL at baseline to 0.88 ng/mL at 40 weeks and in glucagon-stimulate C-peptide levels from 2.18 ng/mL at baseline to 2.01 ng/mL at 40 weeks (FIG. 10d). Subjects 5 and 6 displayed some residual islet β-cell function beyond 10 years after diagnosis of T1D. After receiving closed loop treatment, fasting C-peptide levels in Subject 5 initially decreased from 0.23 ng/mL at baseline to 0.14 ng/mL at 26 weeks, but increased to 0.3 ng/mL at 40 weeks (FIG. 10e). Fasting C-peptide levels in Subject 6 initially declined from 0.26 ng/mL at baseline to 0.09 ng/mL at 26 weeks but improved to 0.21 ng/mL at 40 weeks (FIG. 10f). Their glucagon-stimulated C-peptide levels showed similar tendencies as the fasting C-peptide levels.

In summary, participants in Group A (that is, subjects with some residual islet β cell function) maintained their fasting C-peptide levels at 56 weeks post-treatment (0.46±0.33 ng/mL versus 0.52±0.34 ng/mL at baseline, P=0.7$) (Tables 2A and 2B). Consistently, the median daily doses of insulin (0.37±0.16 U/kg body weight versus 0.38±0.16 at baseline, P=0.84) and the median glycated hemoglobin (HbA1C) (7.8±1.48 versus 7.6±1.3 at baseline, P=0.81) were stabilized after 56 weeks post-treatment. The data demonstrate that the residual β-cell function in Group A patients was rescued and preserved after receiving closed loop treatment without a significant linear decline as the natural history of T1D. Additionally, no changes were observed in fasting C-peptide levels of severe long-standing Group B patients with no residual pancreatic islet β-cell function after receiving two SCE therapies ([Tables 2A and 2B). Their responses to SCE therapy were strikingly different from that reported in long-standing severe Chinese T1D subjects.

TABLE 2A shows the changes in the C-peptide levels of type 1 diabetes patients after treatment at 12 months in the phase 1/2 clinical trial. Group A: T1D patients with residual islet β-cell function.

Additionally, no changes were observed in fasting C-peptide levels of severe long-standing Group B patients with no residual pancreatic islet β-cell function after receiving two bioreactor device therapies (Tables 2A and 2B and Tables 3A and 3B). Their responses to closed loop treatment were strikingly different from that reported in long-standing severe Chinese T1D subjects [Zhao Y. et al., "Reversal of type 1 diabetes via islet β-cell regeneration following immune modulation by cord blood-derived multipotent stem cells", BMC Med., Vol. 10(3), 1-11, (2012)] and [Zhao Y., "Stem cell educator therapy and induction of immune balance", Curr Diab Rep., Vol., 12: 517-523, (2012)]. The potential mechanisms underlying this difference need to be further explored.

| Patient No. | HbA1C before treatment | HbA1C 12 months after treatment | Insulin dose (U/kg body weight) before treatment | Insulin dose (U/kg body weight) 12 months after treatment |
|---|---|---|---|---|
| 1 | 7.1 | 7.4 | 0.28 | 0.29 |
| 2 | 6.3 | 6.3 | 0.32 | 0.30 |
| 3 | 9 | 9.3 | 0.52 | 0.52 |
| 4 | 6.2 | 5.9 | 0.18 | 0.19 |
| 5 | 7.8 | 8.96 | 0.4 | 0.3 |
| 6 | 9.2 | 9 | 0.61 | 0.6 |
| Mean (SD) | 7.6 (1.3) | 7.8(1.48) | 0.38 (0.16) | 0.37 (0.16) |

| Patient No. | Before treatment Basal glycemia | Before treatment Basal C-peptide | Before treatment Post-glucagon C-peptide | 12 months after treatment Basal glycemia | 12 months after treatment Basal C-peptide | 12 months after treatment Post-glucagon C-peptide |
|---|---|---|---|---|---|---|
| 1 | 100 | 0.77 | 1.06 | 175 | 0.84 | 1.31 |
| 2 | 85 | 0.54 | 0.57 | 149 | 0.44 | 0.8 |
| 3 | 155 | 0.25 | 0.4 | 280 | 0.36 | 0.49 |
| 4 | 141 | 1.05 | 2.18 | 130 | 0.88 | 2.01 |
| 5 | 144 | 0.26 | 0.36 | 178 | 0.17 | 0.23 |
| 6 | 218 | 0.23 | 0.27 | 102 | 0.08 | 0.1 |
| Mean (SD) | 140.5 (46.8) | 0.52 (0.34) | 0.81 (0.73) | 169 (61.4) | 0.46 (0.33) | 0.82 (0.73) |

45

TABLE 2B shows the changes in the C-peptide levels of type 1 diabetes patients after treatment at 12 months in the phase 1/2 clinical trial. Group B: T1ID patients with no residual islet β-cell function.

TABLE 3A shows the changes in HbA1C levels and insulin doses of type 1 diabetes patients after treatment at 12 months in the phase 1/2 clinical trial. Group A: T1ID patients with residual islet β-cell function.

| Patient No. | Before treatment Basal glycemia | Before treatment Basal C-peptide | Before treatment Post-glucagon C-peptide | 12 months after treatment Basal glycemia | 12 months after treatment Basal C-peptide | 12 months after treatment Post-glucagon C-peptide |
|---|---|---|---|---|---|---|
| 7 | 230 | <0.01 | <0.01 | 232 | 0.01 | 0.01 |
| 8 | 128 | <0.01 | <0.01 | 135 | 0.01 | 0.01 |
| 9 | 144 | <0.01 | <0.01 | 244 | 0.01 | 0.01 |
| 10 | 198 | <0.01 | <0.01 | 173 | 0.01 | 0.01 |
| 11 | 211 | <0.01 | <0.01 | 182 | 0.01 | 0.01 |
| 12 | 111 | <0.01 | 0.04 | 195 | 0.01 | 0.01 |
| 13 | 165 | <0.01 | 0.01 | 174 | 0.01 | 0.02 |
| 14 | 69 | <0.01 | <0.01 | 123 | 0.01 | 0.01 |
| 15 | 243 | 0.02 | 0.06 | 151 | 0.02 | 0.01 |
| Mean (SD) | 166.56 (58.56) | <0.01 | 0.037 (0.025) | 178.78 (40.64) | 0.01 (0.003) | 0.01 (0.003) |

| Patient No. | HbA1C before treatment | HbA1C 12 months after treatment | Insulin dose (U/kg body weight) before treatment | Insulin dose (U/kg body weight) 12 months after treatment |
|---|---|---|---|---|
| 7 | 7.1 | 7.5 | 0.62 | 0.63 |
| 8 | 6.2 | 6 | 0.72 | 0.74 |
| 9 | 8.4 | 7.9 | 0.92 | 0.89 |
| 10 | 9.1 | 8.4 | 0.79 | 0.8 |
| 11 | 7.4 | 7.5 | 0.56 | 0.56 |
| 12 | 10.1 | 9.2 | 0.58 | 0.57 |
| 13 | 8.3 | 6.8 | 0.51 | 0.5 |
| 14 | 6.5 | 6.6 | 0.71 | 0.72 |
| 15 | 8.4 | 8.3 | 0.96 | 0.9 |
| Mean (SD) | 7.94(1.26) | 7.58(1) | 0.71 (0.16) | 0.7 (0.15) |

TABLE 3B shows the changes in HbA1C levels and insulin doses of type 1 diabetes patients after treatment at 12 months in the phase 1/2 clinical trial. Group B: T1ID patients with residual islet $\beta$-cell function.

Overcoming autoimmune memory is essential for eliminating auto-immunity in T1D and other autoimmune diseases. The described studies demonstrated the safety and feasibility of a two-treatment approach with closed loop treatment, without significantly changing the numbers and ratios of different cell compartments in the subjects' immune system. Both the percentage of CD4$^+$ T$_{EM}$ and CD8$^+$ T$_{EM}$ cells were substantially decreased in the peripheral blood of these Caucasian T1D subjects of European background after receiving SCE therapy, whereas the CD4+T$_{CM}$ appeared to be favored by closed loop treatment. Notably, the levels of CCR7 expression on naïve T and T$_{CM}$ cells were markedly increased after closed loop treatment, further confirmed by ex vivo studies. The percentage of CCR7$^+$ T$_{CM}$ increased at the expense of CCR7$^-$ T$_{EM}$. These findings provide a solution that alters the autoimmune memory compartment in T1D.

Naïve T cells constantly recirculate between secondary lymphoid tissue (SLT) using the blood and lymph as conduits. The present study revealed that the percentage of naive CD4$^+$ T cells was markedly increased in T1D subjects after receiving closed loop treatment. The number of total CD4$^+$ T cells was constantly maintained in peripheral blood during one-year follow-up. Due to the short lifespan (3 months) for most T cells, the data suggest that the expansion of naive CD4$^+$ T cells represented a normal restoration of immune system balance to the T1D subject by closed loop treatment. Clinical evidence demonstrates that population of T$_{EM}$ is increased in chronic inflammation or autoimmune diseases, such as chronic rhinosinusitis [Pant et al., "Accumulation of effector memory CD8+ T cells in nasal polyps", Am. J. Rhinol. Allergy, Vol. 27(5): 117-126, (2013)] and long-standing T1D subjects [Matteucci et al., "Altered proportions of naive, central memory and terminally differentiated central memory subsets among CD4+ and CD8$^+$ T cells expressing CD26 in patients with type 1 diabetes", J. Clin. Immunol, Vol. 31: 977-984, (2011)]. Additionally, both the percentage and absolute cell number of naive T cells and T$_{CM}$ were reduced in longstanding T1D subjects [Matteucci et al., "Altered proportions of naive, central memory and terminally differentiated central memory subsets among CD4$^+$ and CD8+T cells expressing CD26 in patients with type 1 diabetes", J. Clin. Immunol, Vol. 31: 977-984, (2011)]. Notably, the present clinical data demonstrated that the percentage of Naïve CD4$^+$ T cells and T$_{CM}$ were all significantly increased, but D4$^+$ T$_{EM}$ and CD8$^+$ T$_{EM}$ declined in these T1D subjects after receiving closed loop treatment.

Thus, the data demonstrate that closed loop treatment corrected the dysfunction of T$_{EM}$ and favored the differentiation of T$_{CM}$ in long-standing T1D subjects. Differently, both CD4$^+$ T$_{CM}$ and T$_{EM}$, together with CD8$^+$ T$_{CM}$ (but not CD8$^+$ T$_{EM}$), were all decreased by the treatment of new-onset T1D patients with Alefacept therapy in T1D trial, an approach that use the genetically engineered fusion protein targeting and deleting CD2$^+$ T cells.

Example 3: Prospective, Single Arm, Open-Label, Single-Center Pilot Study to Assess the Safety, Feasibility and Efficacy of a Discontinuous Treatment Regime for Treatment of Patients with T1D Study Objectives Primary objective: to assess the safety of a discontinous treatment regime in a pilot group of patient subjects with T1D.

Secondary Objectives

To assess the feasibility of discontinuous treatment in patients with T1D.

To evaluate preliminary efficacy of discontinuous treat ent for improving $\beta$-cell function in patients with T1D through 12 months.

To evaluate markers of immune function in T1D patients after discontinuous treatment.

General Study Design

This is a prospective, single arm, open-label, single-center pilot study to assess the safety, feasibility, and efficacy of discontinuous treatment for the treatment of patients with T1D. Up to 10 patients meeting eligibility criteria will be enrolled. Patients with T1D will be evaluated by the study principal investigator or co-investigators. Informed consent will be obtained at the initial screening visit. The initial screening visit will occur within 30 days of initiation of treatment (Table 4). The second screening visit will occur within 7 days of therapy. Subjects who meet all criteria will be scheduled for treatment. The mononuclear cells of all enrolled subjects will receive treatment with the bioreactor device comprising adherent UC-SC cells. Mononuclear cells will be collected in a single session by pheresis where 10-12 L ($\sim$1$\times$10$^{10}$ mononuclear cells) of blood will be processed on day −1. The MNC product containing the mononuclear cells from each subject will then be exposed over a 17-hour period of time to the device to form a stem cell educated MNC Product. On day 0 the educated MNC product will be infused in ravenously back to the patient over a 3-5 hour period. All treated subjects will receive a telephone follow-up assessment on Day +1 to monitor for acute adverse events +7±1 day. Follow-up visits will occur on the 1st, 3rd, 6th, 9th, and 12th month (±5 days) post-therapy. Subjects will be instructed to record daily insulin doses, sugar levels, and physical activities. After infusion of the educated MNC product, daily insulin doses will be monitored and adjusted by a physician.

CB-SC cultures and device units will be prepared as previously described [Zhao Y. et al., "Reversal of type 1 diabetes via islet $\beta$-cell regeneration following immune modulation by cord blood-derived multipotent stem cells" BMC Med., Vol. 10(3), 1-11, (2012)]. Briefly, human cord blood units derived from healthy allogeneic donors will be obtained from FDA-registered CORD USE Cord Blood Bank (Orlando, FL). All cord blood samples will be screened for HIV 1/2, HBs g, HBcAg, HCV, HIVNAT, STS, HBVNAT, HCVNAT, AbScr, HTLV I/II, West Nile, Chagas, and CMV, and only pathogen-free cord blood units will be used for clinical treatment. The human CB-SCs will be isolated from fresh cord blood unit (at least 100 mL/unit). 50 mL tubes will be put in holders. Three mL HISTOPAQUE®-1077 will be added to each tube, (20 mL conical centrifuge tubes) and brought to room temperature to isolate the CB-SCs. Three mL of whole blood will be carefully layered onto t e HISTOPAQUE®-1077. Centrifugation will be done at 400×g for 30 minutes at room temperature. After centrifugation, the upper layer will be aspirated to within 0.5 cm of the opaque interface containing the CB-SCs. The opaque

86 endotoxin level is <0.05 EU/mL. One device will be generated from one cord blood unit, and used for one subject.

After overnight co-culture of MNC product with CB-SCs, the device-treated MNC product will be collected and infused intravenously (i.v.) back to the subject over a 3 hour period, a 4 hour period, or a 5 hour period.

TABLE 4 shows a schedule of events of the SCE therapy used in the prospective, single arm type 1 diabetes clinical study

| PROCEDURE | SCREENING 1 Day −30 to −1 | SCREENING 2 Day −7 to −1 | Treat Day 0 | Safety 1 Day +1 to +2 | Safety 2 Day +6 to +8 | FU 1 Month 1 | FU 2 Month 3 | FU 3 Month 6 | FU 4 Month 9 | FU 5 Month 12 |
|---|---|---|---|---|---|---|---|---|---|---|
| Informed Consent | x | | | | | | | | | |
| Verify Inclusion/Exclusion Criteria | x | | | | | | | | | |
| Vital Signs (Ht/Wt/Temp/BP/HR/RR) | x | | x | | x | | x | x | x | x |
| Medical History | x | | x | | x | | x | x | x | x |
| Physical Exam | x | | x | | x | | x | x | x | x |
| Various assessment for apheresis | x | | | | | | | | | |
| LOCAL LABS | | | | | | | | | | |
| CBC | x | | x | | x | | x | x | x | x |
| CMP | x | | | | | | x | x | x | x |
| HbA1C | x | | | | | | x | x | x | x |
| Infectious disease panel | x | | | | | | | | | |
| Urine Pregnancy Test | | x | | | | | | | | |
| Auto-antibodies (ICA, IAA, IA2, GAD, ZnT8) | x | | | | | | x | x | x | x |
| EKG | x | | | | | | | | | |
| METABOLIC STATUS | | | | | | | | | | |
| Mixed meal tolerance test | | x | | | | | x | x | x | x |
| Daily Insulin Doses: Patient Diary | | | | | Continuous | | | | | |
| Daily Glucose Levels: Patient Diary | | | | | Continuous | | | | | |
| IMMUNE MARKERS | | | | | | | | | | |
| CD4⁺CD25⁺Foxp3⁺ Tregs | | x | | | | x | x | x | x | x |
| IL-1, TNFα, IL-17 | | x | | | | x | x | x | x | x |
| IL-10 and TGF-β1 | | x | | | | x | x | x | x | x |
| Th1/Th2 cytokines (IL-4, IL-5, IL-12, IL-13) | | x | | | | x | x | x | x | x |
| TREATMENT | | | | | | | | | | |
| Apheresis | | day −1 x | cell infusion | | | | | | | |
| SAFETY ASSESSMENTS | | | | | | | | | | |
| Phone call for safety follow-up | | | | x | x | | | | | |
| Concomitant med monitoring | | | | | | Continuous | | | | |
| Adverse event monitoring | | | | | | Continuous | | | | | interface will be transferred in a new clean 20 mL conical tube. The cells will be washed with 10 mL isotonic phosphate buffered saline solution. After washing which is done by mixing and centrifuging at 250×g for minutes, the supernatant will be discarded and after washing two more times, the CB-SCs will be resuspended in 0.5 mL isotonic phosphate buffered saline solution. Human CB-SCs will be produced and the cord blood mononuclear cells will be plated in 150×15 mm Petri dishes (Becton Dickinson Labware, Franklin Lakes, NJ, not tissue culture-treated dishes) at a density of at least 1×10⁶ cells/mL, 25 mL/dish in RPMI 1640 medium and incubated at 37° C. in 8% CO₂. Cord blood mononuclear cells will be plated in bioreactor devices in serum-free culture medium (Lonza, Walkersville, MD) and incubated at 37° C., in 8% CO₂ for about 2-3 weeks. CB-SCs will be observed for being round and further verified for attachment on the bottom of the Petri dishes. CB-SCs growing at 80% confluence (about 1×10⁷ cells/device) will be prepared for the clinical trial. Desired Primary Study Endpoints Primary study endpoints include the occurrence of treatment-related adverse events. Adverse events that occur during therapy (especially those that necessitate temporary or permanent discontinuation of therapy) and over the 12-month follow-up period will be assessed.

Secondary Study Endpoints (Feasibility Endpoints)

Feasibility endpoints include the number of patients who were unable to complete the discontinuous treatment and the number of patients who are lost to follow-up prior to the 12-month follow-up visit.

Any non-adverse event related reasons for discontinuation of therapy will be recorded (e.g. technical problems with the device).

Secondary Study Endpoints (Efficacy Endpoints)

Efficacy endpoints include:

The Area under the C-peptide curve (AUC) over the first 2 hours of a 3-hour mixed meal tolerance test (MMTT), and an assessment of the AUG at 12-months and changes over time;

An assessment of peak C-peptide levels over a 3-hour MTT, peak C-peptide level at 12-months and changes over time;

An assessment of basal C-peptide levels at 12-months and changes over time;

An assessment of daily insulin requirements;

An assessment of change in HbA1C levels over time; and

An assessment of changes in auto-antibody levels over time.

Secondary Study Endpoints (Exploratory Endpoints)

Exploratory endpoints include measurements of regular immune cell markers at baseline, 1, 3, 6, 9, and 12 months and flow cytometry of memory T cell markers at baseline, 1, 3, 6, 9, and 12 months. Blood samples for testing will be shipped to the NIH/NIDDK designated North American Autoantibody/HLA Core Laboratory at Barbara Davis Center for Diabetes, School of Medicine, University of Colorado.

Subject Selection and Withdrawal

This study will enroll a total of 10 subjects who meet the following eligibility criteria:

Inclusion Criteria

1) Adult patients (18 years).

2) Must have a diagnosis of type 1 diabetes mellitus based on the 2015 American Diabetes Association criteria for the Clarification and Diagnosis of diabetes.

3) Must have a blood test confirming the presence of at least one autoantibody to pancreatic islet β-cells (ICA, IAA, IA2, GAD 65, ZnT8).

4) Fasting C-peptide level>0.3 ng/mL.

5) Adequate venous access for apheresis.

6) Ability to provide informed consent.

7) Must agree to comply with all study requirements and be willing to complete all study visits.

Exclusion Criteria

Potential subjects meeting any of the following criteria will be excluded from participation:

1) AST or ALT 2>x upper limit of normal.

2) Creatinine>2.0 mg/dl.

3) Known coronary artery disease or EKG suggestive of coronary artery disease unless cardiac clearance by a cardiologist is obtained.

4) Known active infection.

5) Pregnancy or breastfeeding mothers.

6) Use of immunosuppressive medication within one month, of enrollment including but not limited to prednisone, cyclosporine, tacrolimus, sirolimus, and chemotherapy.

1) Presence of any other autoimmune diseases (lupus, rheumatoid arthritis, scleroderma, etc.).

2) Anticoagulation other than acetylsalicylic acid (ASA).

3) Hemoglobin<10 g/dL or platelets<100 k/mL.

4) Is unable or unwilling to provide informed consent.

5) Presence of any other physical or psychological medical condition that, in the opinion of the investigator, would preclude participation.

Subject Recruitment and Screening

If subject's consent to participate in the clinical trial, has been obtained, diagnostic testing necessary to meet above inclusion or exclusion criteria will be performed. The list of screening requirements will include a reg lar blood count analysis, a blood test to confirm the presence of at least one autoantibody to pancreatic islet beta-cells, and other associated testing to exclude clinically significant liver, kidney, or heart disease; pregnancy; immunosuppressive medication; viral diseases; or diseases associated with human immunodeficiency virus (HIV).

Early Withdrawal of Subjects

The risks to the patients are expected to be minimal and akin to a standard apheresis procedure. The cells returned to the patients are autologous cells that will be treated (or educated) by CB-SCs. In this study a patient may be withdrawn from this protocol:

If the patient suffers some type of allergic or hypersensitivity reaction to the SCE treated cells precluding the infusion of the product.

If technical difficulties preclude the completion of apheresis.

If the patient does not want to complete the required post treatment follow-up testing.

Participation in this trial is voluntary for all subjects. If a subject decides not to participate, the subject is free to withdraw their consent and discontinue participation at any time without affecting their future care at the healthcare facility. In the event that a patient is withdrawn for above or any other unexpected reasons they will be allowed to continue to receive medical care for treatment associated problems.

Data Collection and Follow-Up for Withdrawn Subjects

Even though subjects may be withdrawn prematurely from the study, it is imperative to collect toxicity data for 12 weeks after. We will use all possible methods (e.g. number of phone calls to subject, phone calls to next-of-kin listed on the HIPPA Form if possible, certified letters, etc.) to confirm that the subjects is truly lost for follow-up. If a patient withdraws from the study prior to their 12 month follow-up, enrollment of a replacement patient will occur.

Study Device

A chamber (160×160×200 cm) for co-culture of lymphocytes and CB-SCs as part of a continuous closed loop system has been described [Zhao Y. et al., "Reversal of type 1 diabetes via islet β-cell regeneration following immune modulation by cord blood-derived multipotent stem cells", BMC Med., Vol. 10(3), 1-11, (2012)] and T2D [Zhao Y. et al., "Targeting insulin resistance in type 2 diabetes via immune modulation of cord blood-derived multipotent stem cells (CB-SCs) in stem cell educator therapy: phase I/II clinical trial", BMC Med., Vol. 11: 160, (2013)] this pilot study will use a discontinuous system, i.e., the whole blood sample obtained from a subject will be sent to a processing facility, the processing facility will prepare the educated MNC product, and once the educated MNC product meets release criteria, will ship the educated MNC product back to a clinical facility for infusion into the subject.

Each bioreactor device will be designed, manufactured, assembled and packaged in a Class 100K clean room. After being sterilized by gamma-irradiation (Cesium-137), each device will be stored at room temperature in dark cabinets of a Class 100K clean room, which is an FDA-approved facility for cell isolation and cultures. The materials used to produce the device are FDA-approved for in vivo use per the United States Pharmacopeia (i.e., Grade Class VI Plastic). The sterilized device is single use. CB-SCs are generated from one cord blood unit for one subject application. CB-SCs remain inside of the device due to their unique attaching ability [Zhao Y. et al., "Reversal of type 1 diabetes via islet @-cell regeneration following immune modulation by cord blood-derived multipotent stem cells", BMC Med., Vol. 10(3), 1-11, (2012)].

Treatment Regimen

Subjects who meet all criteria will be scheduled for treatment by the following discontinuous method A whole blood sample will be collected for each subject and mononuclear cells will be collected by apheresis; 10-12 L (~1×

Figure 11:
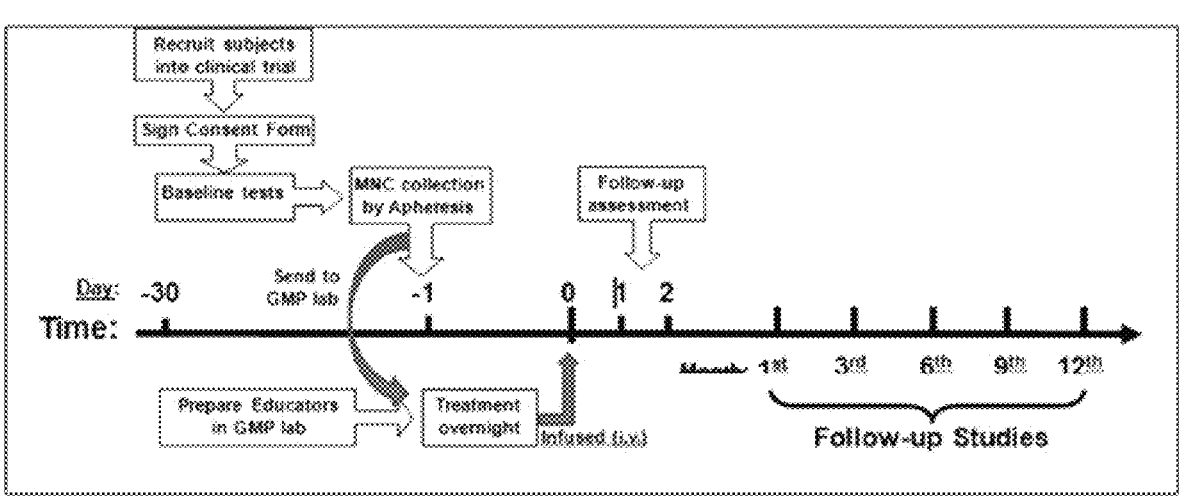
FIG. 11 depicts the treatment regime for SCE treatment and follow-up in the prospective, single arm, open label, single-center pilot study. Mononuclear cells will be obtained under sterile conditions from each subject by apheresis, transported to a processing facility, treated in the SCE device overnight in the processing facility, and then transported back to a clinical facility for reinfusion into the subject.

$10^{10}$ mononuclear cells) of blood will be processed on day −1. The mononuclear cell preparation will be shipped to a cGMP processing facility. At the processing facility the mononuclear cell preparation will be introduced into the bioreactor device containing adherent UC-SC cells over a 17-hour period of time. The educated mononuclear cell product will be tested for sterility, viability and purity; once release criteria have been satisfied, the processing facility will send the educated mononuclear cell product to a clinical facility. On day 0 the product will be infused intravenously back to the patient. All treated subjects will receive a telephone follow-up assessment on Day +1 to monitor for acute adverse events. All treated subjects will attend a safety visit on Day +7±1 day. Follow-up visits will occur on 1st, 3rd, 6th, 9th, and 12th month (±5 days) post-therapy as shown in FIG. 11. Subjects will be instructed to record daily insulin doses, sugar levels, and physical activities. After treatment, patients' daily insulin doses will be monitored and adjusted by their own physician.

Method for Assigning Subjects to Treatment Group

Based on fasting C-peptide levels (a by-product of insulin biosynthesis, with normal reference range 0.8-3.1 ng/mL), as an indicator for islet-β cell function, all participants will be characterized and assigned as one group having moderate T1D with some residual β-cell function (fasting C-peptide level≥0.3 ng/mL, n=10). Each participant will receive one treatment.

Preparation and Use of Study Device

Figure 12C:
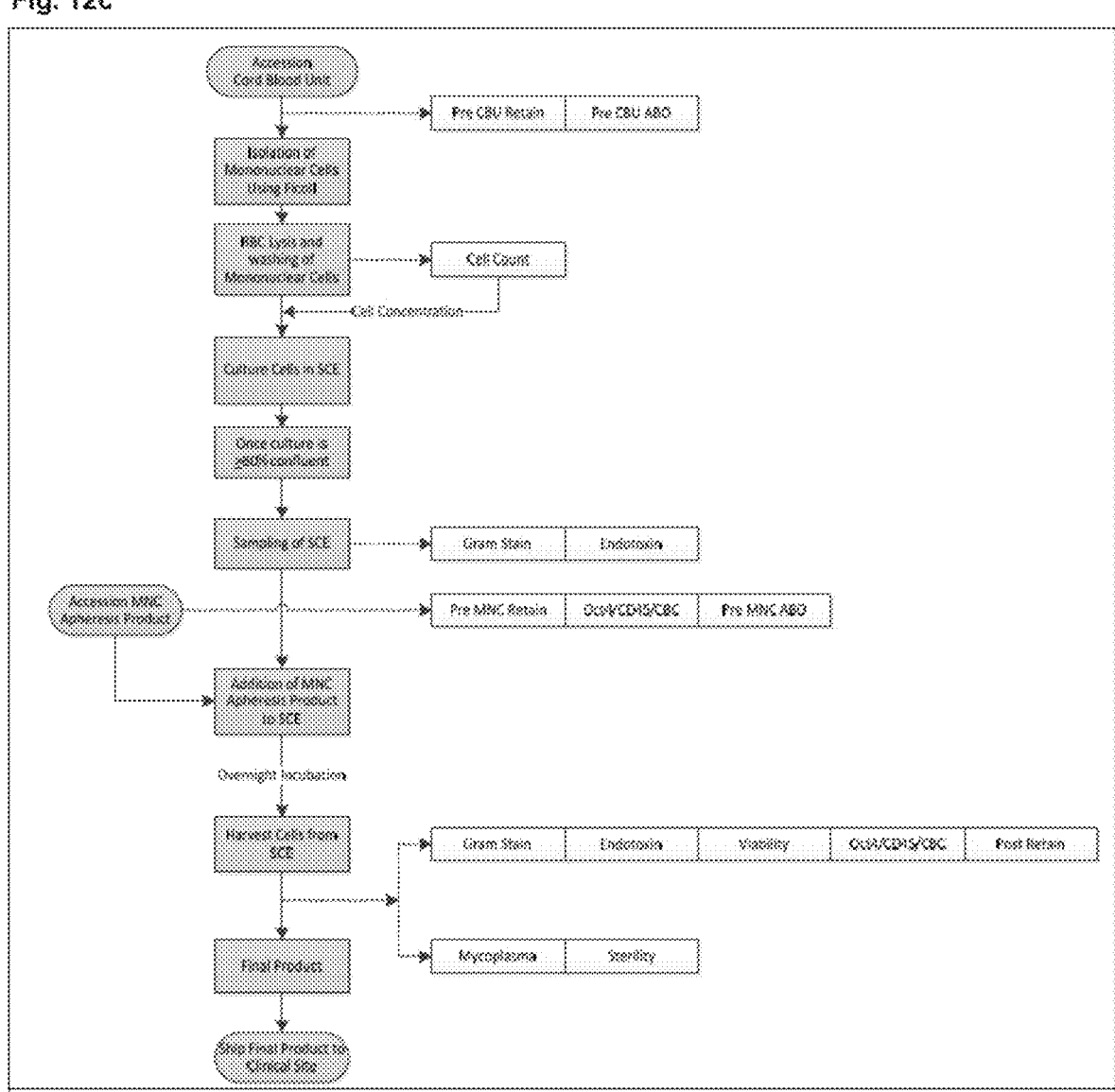
Figure 13:
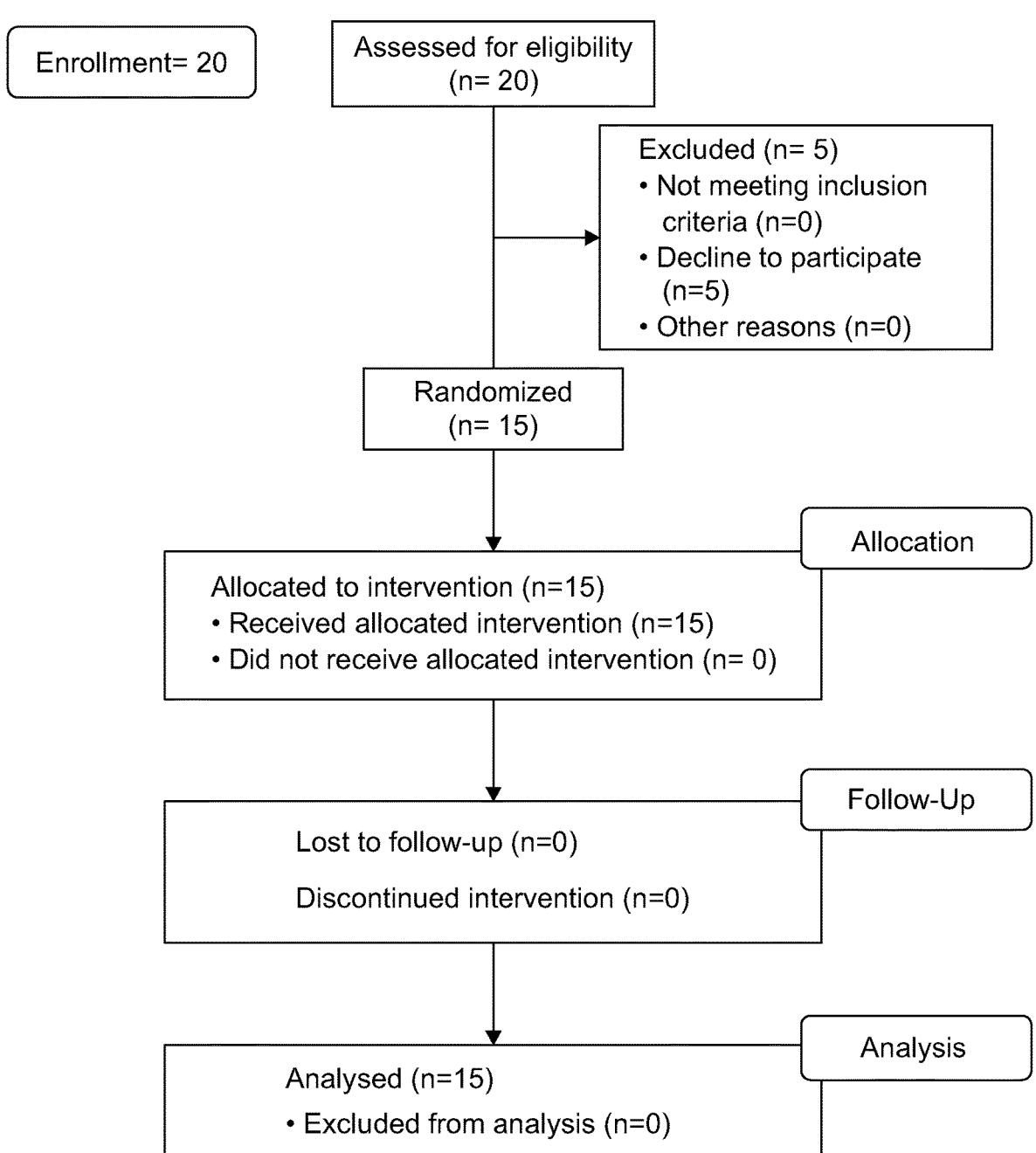

Use of the bioreactor device comprising adherent UC-SC cells to treat the MNC preparation will be extended to 17 hours through overnight co-culture of mononuclear cells and CB-SCs in the cGMP processing facility. The protocol for the preparation and use of the SCE device is shown as following steps as a diagram in FIGS. 12a-c and as described below.

Step 1: Collection of Human Cord Blood Units

Human cord blood units derived from healthy donors will be provided by FDA-registered CORD: USE Cord Blood Bank Inc. All cord blood samples are screened for communicable disease as requested by regulatory agencies Step 2: Preparation of CB-SC in the Device Prior to introducing CB-SCs into the device, cord blood mononuclear cells will be isolated from fresh cord blood unit (at least 100 mL/unit) according to the following protocol:

1) Take 50 mL tubes and put in holders: normally use 4 tubes;

2) Add HISTOPAQUE®-1077 to each tube at 20 mL/tube to isolate the mononuclear cells;

3) Plant mononuclear cells in the device (Tianhe Stem Cell Biotechnologis Inc.) at $1\times10^6$ cells/mL, 25-30 mL/dish in serum-free culture medium;

4) Incubate cells at 37° C., 8% $CO_2$ conditions for 10-20 days;

5) Cell observation: CB-SC are round and attach on the bottom of dishes. If cell density reaches at least 80% of confluence, CB-SC can be prepared for clinical application.

Step 3: Test the CB-SC Culture for Endotoxin and Gram Stain

Testing for Endotoxin

The supernatant from the culture of CB-SCs will be collected into 1.8 mL sterilized tubes. Endotoxin will be tested by using the Endosafe-PTS Portable Test System (Charles River, Charleston, SC) and Endosafe-Licensed PTS Endotoxin Cartridge (0.05 EU/mL sensitivity, Fisher Scientific). The standard endotoxin level will be <0.5 EU/mL. Only the SCE device that meets this standard can be used for the clinical trial.

Gram Stain

The supernatant from the culture of CB-SCs will be collected into 1.8 mL sterilized tubes. Gram staining will be performed by using the Gram Stain kit (BD Diagnostic Systems, Sparks, MD). Only negatively stained devices can be used for the clinical trial. The test specimen is applied to a clean glass slide in a manner that will yield a thin and uniform smear of the supernatant from the culture of CB-SCs. The smear is allowed to air dry. The smear is fixed to the slide using one of the following techniques.

Heat fixing by passing the slide through a low flame 2-3 times. The slide is cooled to room temperature before staining. Or, by fixing the slide by flooding with absolute methanol for 1-2 min and rinsing with tap water before staining.

Test Procedure

The test procedure for the Gram Stain is as follows:

The fixed smear is flooded with primary stain (Gram Crystal Violet) and stained for 1 min.

The primary stain is removed by gently washing with cold tap water.

The slide is flooded with mordant (Gram Iodine or Stabilized Gram Iodine) and retained on the slide for 1 min.

The mordant is removed by gently washing with tap water.

The mordant is decolorized (Gram Decolorizer) until solvent running from the slide is colorless (3-60 seconds).

The slide is washed gently in cold tap water.

The slide is flooded with counterstain (either Gram Safranin or Gram Basic Fuchsin) and stain for 30-60 seconds.

The slide is washed with cold tap water.

The slide is blotted with blotting paper or paper towel or allowed to air dry.

The smear is examined under an oil immersion lens.

Step 4: Preparation of the Bioreactor Device

The device is prepared at the processing facility by executing the following steps:

1) Sterilize the hood in a GMP facility for preparation of the device;

2) Clean out side of device with 70% ethanol gauze and carefully remove all caps;

3) Discard all supernatants inside of device;

4) Add physiological saline to each layer at 20 mL/layer, washing each layer and removing all floating cells and debris;

5) Additional wash with physiological saline (20 mL/layer);

6) Remove the caps from the top and bottom, replace with Plastisol Horseshoe Y Connectors, and seal with Medical Device Super Glue (these glues meet USP Class 6 criteria for use on medical devices);

7) Add physiological saline to each layer at 15-20 mL/layer, and close with caps;

8) Turn around the device and check for leaking;

9) Put in the sterilized container;

Step 5: Co-Culture Mononuclear Cell Product by Passage into the Device Comprising an Adherent Monolayer of CB-SC's 1) On day −1 patients will undergo a steady state mononuclear collection by apheresis in a clinical facility with an optimal goal of processing 10-12 L (~$10^{10}$ mononuclear cells) of blood. Apheresis may be stopped before the goal is reached based on tolerability and venous access. A minimum of 6 L processed will be required to continue on to the next phase. Plasma will be added to the collection bag at the end of apheresis to target a product volume of 250 mL. Labeling of the product will be done prior to disconnecting the product from the donor in accordance with the Blood and Marrow Transplant program labelling policy.

2) The product will be packaged, stored and picked up by the GMP facility in accordance with the Blood and Marrow Transplant prog am SOPs.

3) Once at the GMP facility, the GMP facility will expose the MNC product to the device.

4) On day Q, the educated mononuclear cell (MNC) product will be infused to the patient in accordance with the Blood and Marrow Transplant program cellular infusion SOP.

Upon receipt of the study treatment supplies, an inventory must be performed and a device receipt log filled out and signed by the person accepting the shipment. It is important that the designated study staff count and verify that the shipment contains all the items noted in the shipment inventory. Any damaged or unusable study device in a given shipment will be documented in the study files. The investigator must notify study sponsor of any damaged or unusable study treatments that were supplied to the investigator's site.

The devices are stored at room temperature in dark cabinets of the GMP facility suitable for cell cultures. There is no need for protection from light. Storage considerations include avoiding dropping of the devices or placing a heavy weight on top of the devices.

All empty devices (without stem cells) are of the same quality. Any single device will be assigned to any single subject and dispensed.

The only standard will be the quality of CB-SCs cultured in the device. If cell density reaches the ≥80% of confluence, endotoxin level<0.5 EU/mL, the device with CB-SCs can be assigned to a subject and prepared for clinical application. Regular study device reconciliation will be performed to document device assignments, devices used, devices remaining, and inadvertently damaged devices. This reconciliation will be logged on the device accountability form, and signed and dated by the study team.

Devices are discarded at the conclusion of the treatment as per institutional biohazard waste disposal SOP. At the completion of the study, there will be a final reconciliation of devices shipped, devices consumed, and devices remaining. This reconciliation will be logged on the device reconciliation form, signed and dated. Any discrepancies noted will be investigated, resolved, and documented prior to return or destruction of unused study devices. Any devices destroyed on site will be documented in the study files.

Step 6: Testing the Treated MNC Product (Hereinafter the Final Product) for Endotoxin, Gram Stain, *Mycoplasma*, and Stem Cell Markers Testing for Endotoxin A sample from the CB-SC-treated MNCs will be collected into 1.8 mL sterilized tubes. Endotoxin will be tested by using the Endosafe-PTS Portable Test System (Charles River, Charleston, SC) and Endosafe-Licensed PTS Endotoxin Cartridge (0.05 EU/mL sensitivity, Fisher Scientific). A routine PTS LAL assay is conducted by following the simple prompts on the PTS instrument. The following represents a typical assay procedure:

Instrument Operation

Press the MENU key on the PTS keypad to turn instrument on (Menu 5 turns instrument off).

The PTS Reader initiates a "SYSTEM SELF TEST" as it heats up to 37° C.—this takes approximately 5 minutes.

The PTS Reader displays "SELF TEST OK" and then "INSERT CARTRIDGE".

Insertion of Sample

Insert the Cartridge.

Allow the cartridge to come to room temperature in pouch before use.

Remove cartridge from pouch and insert with sample reservoirs facing up into slot at front of the PTS Reader.

Press cartridge firmly into slot.

Enter Required Information

Once the cartridge has been firmly inserted into the PTS Reader, the PTS Reader prompts the user to enter the following information:

Enter OID (Operator ID).

Enter Lot #(Cartridge Lot #).

Enter Calibration Code (if the Calibration Code for the particular lot #has already been entered, the PTS Reader does not prompt for the code again. (To erase all stored lot #'s and corresponding calibration codes, select menu, 2, followed by 4 from the initial menu).

Lot #(Confirms Cartridge Lot Number Entered)

Enter Sample Lot #.

Enter Sample ID (Selecting and scrolling with the menu key under the sample ID Header allows for fifty (50) samples to be entered and stored).

Enter Dilution Factor.

While the above information is being entered into the PTS Reader, the cartridge is being pre-warmed.

Dispense the Sample

Once all test information is entered, the PTS Reader displays:

ADD SAMPLE; PRESS ENTER.

Pipette 25 µL of sample into all four (4) sample reservoirs of the inserted cartridge and press Enter on the PTS Reader keypad.

Pumps draw sample aliquots into the test channels, thereby initiating the test.

Results will be obtained in approximately 15 minutes. When the test is complete, the PTS Reader gives an audible notification that the assay is finished. At the conclusion of the test, the endotoxin measurement and the assay acceptance criteria are displayed on the screen.

The standard endotoxin level will be <0.5 EU/mL. Only the Final Product that meets this standard can be used for the clinical infusion.

Gram Stain

The supernatant from the culture of CB-SCs will be collected into 1.8 mL sterilized tubes. Gram staining will be performed by using the Gram Stain kit (BD Diagnostic Systems, Sparks, MD). Only negatively stained devices can be used for the clinical trial. This is done by applying the test specimen to a clean glass slide in a manner that will yield a thin and uniform smear of the supernatant from the culture of CB-SCs. The smear is allowed to air dry. The smear is fixed to the slide using one of the following techniques.

Heat fixing by passing the slide through a low flame 2-3 times. The slide is cooled to room temperature before staining. Or, by fixing the slide by flooding with absolute methanol for 1-2 min and rinsing with tap water before staining.

Test Procedure

Test Procedure for the Gram Stain is as follows:

Flood the fixed smear with primary stain (Gram Crystal Violet) and stain for 1 min.

Remove the primary stain by gently washing with cold tap water.

Flood the slide with mordant (Gram Iodine or Stabilized Gram Iodine) and retain on the slide for 1 min.

Remove the mordant by gently washing with tap water.

Decolorize (Gram Decolorizer) until solvent running from the slide is colorless (3-60 seconds).

Wash the slide gently in cold tap water.

Flood the slide with counterstain (either Gram Safranin or Gram Basic Fuchsin) and stain for 30-60 seconds.

Wash the slide with cold tap water.

Blot with blotting paper or paper towel or allow to air dry.

Examine the smear under an oil immersion lens.

Testing for *Mycoplasma*, Cell Viability and Sterility

Sterility and contamination of *Mycoplasma* in the sample from the CB-SC-treated MNCs can be assessed by the following methods.

For regular cell cultures, cell viability can be monitored under phase-contrast microscope to exclude the contamination of *mycoplasma* and other bacteria.

Alternatively, cell viability is determined by excluding the dying cells which take up the intercalating DNA dye 7-aminoactinomycin D (7AAD) [Brocklebank A. M. et al., "Enumeration of CD34$^+$ cells in cord blood: a variation on a single-platform flow cytometric method based on the ISHAGE gating strategy", Cytometry. Vol. 46: 254-261, (2001)]; [Barnett D, et al., "Absolute CD4$^+$ T-lymphocyte and CD34$^+$ stem cell counts by single-platform flow cytometry: the way forward", Br. J Haematol. Vol. 106: 1059-1062, (1999)]; [Sutherland, et al., "The ISHAGE guidelines for CD34+c II determination by flow cytometry. International Society of Hematotherapy and Graft Engineering", J Hematotherapy. Vol. 5: 213-226, (1996)], and U.S. Pat. Nos. 4,520,110; 4,859,582; 5,055,556; European Patent No. 76.695; Canadian Patent No. 1,179,942 (PE, APC); U.S. Pat. No. 4,876,190 (PerCP); U.S. Pat. Nos. 5,286,486; 5,486, 616; 5,569,587; 5,569,766; 5,627,027 (Cy); U.S. Pat. Nos. 4,714,680; 4,965,204, 5,035,994 (CD34); U.S. Pat. No. 5,776,709 (Lyse/no-wash method); U.S. Pat. Nos. 5,723,218 and 5,187,288 (TruCOUNT Tubes), the contents of each of which are incorporated by reference herein in their entirety.

Real time PCR: A sample from the educated MNC product will be collected into 1.8 mL sterilized tubes and tested by BioReliance (Rockville, MD) in compliance with the requirements of the US FDA Good Laboratory Practice Regulations (21 CFR 58). 3).

Sterility Testing will be performed by using a Direct Inoculation Method at BioReliance Company.

Testing for Stem Cell Markers CD45 and OCT3/4 by Flow Cytometry

To exclude contamination of the educated MNC product with CB-SCs flow cytometry with double-staining for CB-SCs markers CD45 and OCT3/4 will be performed.

Subject Compliance Monitoring

Subjects will receive one treatment with the bioreactor device. Follow-up visits will be scheduled 1, 3, 6, 9 and 12 months (±5 days) after treatment for clinical assessments and laboratory tests as described previously. A telephone follow-up will be performed the day after the cell infusion.

Prior and Concomitant Therapy

All T1D subjects shall receive their daily insulin injections prior to or during the study. Daily insulin doses will be adjusted after discontinuous treatment by the subject's own physicians, not the study PI. No other new diabetes medicines or therapies will be permitted during this study.

Packaging

The bioreactor devices will be packaged in box (4 devices/box) and shipped to the cGMP facility with the Good Manufacturing Practices (GMP) Labeling System.

After treatment with the device, the educated MNC Product will be shipped to the clinical site in a sterilized cooler. One device containing CB-SCs from one cord blood unit will be used for each subject.

Blinding

In this single-arm study, MNC products acquired and enriched from all subjects will receive open label treatment with the device.

Study Procedures—Visit 1

Screen for Enrollment:

First, all consented subjects will be screened for enrollment in accordance with the Inclusion Criteria and Exclusion Criteria of the discontinuous treatment. Patients will be qualified for enrollment if they meet the 2015 diagnosis standards of the American Diabetes Association and a blood test confirm the presence of at least one autoantibody to pancreatic islet beta cells themselves.

Complete Blood Count (CBC) with different immune cell markers.

EKG.

Venous assessment as per Blood and Marrow Transplant program SOP. Patients without sufficient venous access will be referred for a central venous catheter placement able to sustain apheresis flow rates. Catheter placement will be performed no earlier than 5 days prior to the apheresis procedure and will be removed after infusion of the Educated MNC Product.

Specifically testing for the presence of autoantibodies against islet cell cytoplasmic (ICA), insulin autoantibodies (IAA), insulinoma-associated antigen-2 (IA2), glutamic acid decarboxylase (GAD) and pancreatic beta-cell-specific zinc transporter ZnT8 will be performed (see Table 4).

Infectious disease testing (HIV, HTLV, Hep B, cAB, Hep C ab will be performed.

Venous assessment as per institutional SOP will be performed.

Mixed Meal Tolerance Test (MMTT): MMTT testing should be done in the morning while the subject is fasting. Subjects will consume nothing by mouth (NPO) after midnight except water. Liquids that contain only simple sugars can be used to treat or prevent hypoglycemia during the night and morning prior to study. The target glucose level at the start of the test should be between 70 and 200 mg/dL for subjects with T1 DM.

Insulin Application: Subjects with T1DM should take their usual dose of insulin on the evening before the test. Subjects on Lantus® or Levemir® should take their usual injection the evening before and/or on the morning of the test, as per their normal routine. Subjects on continuous subcutaneous insulin infusion (CSII) should continue with their usual basal settings on night prior to test. Usual doses of rapid-acting insulin analog will be used until midnight the evening before the test. Small correction doses of rapid-acting insulin analog may also be used up to 4 hours before the test if needed to achieve a blood glucose level<150 mg/dL at the start of the study. Usual doses of neutral protamine Hagedorn (NPH) human insulin (rDNA origin) aid rapid-acting insulin analogs are not given on the morning of the test.

Blood Sampling: Blood will be obtained for measurement of plasma glucose, c-peptide and glucagon at −10, 0, 15, 30, 60, 90, 120, 150 and 180 minutes. A split-duplicate sample for quality control will also be collected. IV lines will be inserted in one arm for blood sampling.

Boost Dose: The mixed meal used will be Boost High Protein Nutritional Energy Drink® (Mead-Johnson).

The MMTT should take 180 minutes to perform. The dose of Boost High Protein Nutritional Energy Drink® (Mead-Johnson) mixed meal is 6 kcal/kg (@1 kcal/mL=6 mL/kg), given at time 0 minutes. The dose should be consumed in no more than 5 minutes.

Study Procedures—Visit 2

Ten participants will receive a single treatment with the bioreactor comprising adherent UC-SC cells.

Study Procedures—Visit 3

Follow-up visit 1 is scheduled 1 month (±5 days) after treatment for clinical assessments (e.g., fasting blood glucose, C-peptide, and HbA1C) and laboratory tests as per Table 4.

Study Procedures—Visit 4

Follow-up visit 2 is scheduled 3 months (±5 days) after treatment for clinical assessments (e.g., fasting blood glucose, C-peptide, and HbA1C) and laboratory tests as per Table 4.

Study Procedures—Visit 5

Follow-up visit 3 is scheduled 6 months (±5 days) after treatment for clinical assessments (e.g., fasting blood glucose, C-peptide, and HbA1C) and laboratory tests as per Table 4.

Study Procedures—Visit 6

Follow-up visit 4 is scheduled 9 months (±5 days) after treatment for clinical assessments (e.g., fasting blood glucose, C-peptide, and HbA1C C-peptide levels post a 75 g-OGTT and MMTT) and laboratory tests as per Table 4.

Study Procedures—Visit 7

Follow-up visit 5 is scheduled 12 months (±5 days) after treatment for clinical assessment and laboratory tests as per Table 4.

Statistical Plan

Statistical Methods

An intention-to-treat approach will be used, with 10 patients undergoing treatment using the discontinuous regime. All patients will be included in the safety analyses.

The primary efficacy end point will be the change in C-peptide secretion between baseline and follow-up. Statistical analyses of data will be performed by t-test using Power and Precision software (www.power-analysis.com). Paired t test will be used to study the significance between baseline and follow-ups. Using the fasting blood glucose levels and the plasma C-peptide, as well as their levels following an oral glucose tolerance test (OGTT) or MMTT as the parameters, we want to detect the difference after the SCE therapy with an effect size of 0.8 ng/mL at 2.5% significance level, 80% power, one side. According to our calculations, we will need 10 subjects in order to find this difference.

Subject Population(s) for Analysis

All protocol-compliant subject populations will be included in the safety analyses. The primary efficacy end point will be the change in C-peptide secretion between baseline and follow-up.

Safety and Adverse Events—Definitions

Any incident, experience, or outcome that meets all of the following criteria:

Unexpected in nature, severity, or frequency (i.e. not d scribed in study-related documents such as the IRB-approved protocol or consent form, the investigators brochure, etc).

Related or possibly related to participation in the research (i.e. possibly related means there is a reasonable possibility that the incident experience, or outcome may have been caused by the procedures involved in the research.

Serious (as defined below) "Serious" is different than "severe" as reported in the CTC criteria that applies a grade to the AE.

Adverse Event

An adverse event (AE) is any symptom, sign, illness or experience that develops or worsens in severity during the course of the study. Concurrent illnesses or injuries should be regarded as adverse events. Abnormal results of diagnostic procedures are considered to be adverse events if the abnormality:

Results in study withdrawal.

Is associated with a serious adverse event.

Is associated with clinical signs or symptoms.

Leads to additional treatment or to further diagnostic tests.

Is considered by the investigator to be of clinical significance.

Serious Adverse Event

Adverse events are classified as serious or non-serious. A serious adverse event is any adverse event that is:

Fatal.

Life-threatening.

Requires or prolongs hospital stay.

Results in persistent or significant disability or incapacity.

A congenital anomaly or birth defect.

An important medical event.

Important medical events are those that may not be immediately life threatening, but are clearly of major clinical significance. They may jeopardize the subject, and may require intervention to prevent one of the other serious outcomes noted above. For example, drug overdose or abuse, a seizure that did not result in in-patient hospitalization, or intensive treatment of bronchospasm in an emergency department would typically be considered serious. All adverse events that do not meet any of the criteria for serious should be regarded as non-serious adverse events.

Adverse Event Reporting Period

The study period during which adverse events must be reported is normally defined as the period from the initiation of any study procedures to the end of the study treatment follow-up. For this study, the study treatment follow-up is defined as 30 days following the administration of study treatment. Serious adverse events should be reported to the local IRB and FDA within 7-10 days from the time of the event. Minor events can be reported in an annual report.

Preexisting Condition

A preexisting condition is one that is present at the start of the study. A preexisting condition should be recorded as an adverse event if t e frequency, intensity, or the character of the condition worsens during the study period.

General Physical Examination Findings

At screening, any clinically significant abnormality should be recorded as a preexisting condition. At the end of the study, any new clinically significant findings/abnormalities that meet the definition of an adverse even must also be recorded and documented as an adverse event.

Post-Study Adverse Event

All unresolved adverse events should be followed by the investigator until the events are resolved, the subject is lost to follow-up, or the adverse event is otherwise explained. At the last scheduled visit, the investigator should instruct each subject to report any subsequent event(s) that the subject, or the subject's personal physician, believes might reasonably be related to participation in this study. The investigator should notify the study sponsor of any death or adverse event occurring at any time (during the 6-month follow-up) after a subject has discontinued or terminated study participation that may reasonably be related to this study. The sponsor should also be notified if the investigator should become aware of the development of cancer or of a congenital anomaly in a subsequently conceived offspring of a subject that has participated in this study.

Abnormal Laboratory Values

A clinical laboratory abnormality should be documented as an adverse event if any one of the following conditions is met:

The laboratory abnormality is not otherwise refuted by a repeat test to confirm the abnormality.

The abnormality suggests a disease and/or organ toxicity.

The abnormality is of a degree that requires active management; e.g. change of dose, discontinuation of the drug, more frequent follow-up assessments, further diagnostic investigation, etc.

Hospitalization, Prolonged Hospitalization or Surgery

Any adverse event that results in hospitalization or prolonged hospitalization should be documented and reported as a serious adverse event unless specifically instructed otherwise in this protocol. Any condition responsible f r surgery should be documented as an adverse event if the condition meets the criteria for and adverse event. Neither the condition, hospitalization, prolonged hospitalization, nor surgery are reported as an adverse event in the following circumstances:

Hospitalization or prolonged hospitalization for diagnostic or elective surgical procedures for a preexisting condition. Surgery should not be reported as an outcome of an adverse event if the.

purpose of the surgery was elective or diagnostic and the outcome was uneventful.

Hospitalization or prolonged hospitalization required to allow efficacy measurement for the study.

Hospitalization or prolonged hospitalization for therapy of the target disease of the study, unless it is a worsening or increase in frequency of hospital admissions as judged by the clinical investigator.

Recording of Adverse Events

No significant adverse events were seen during closed loop treatment with the bioreactor device, and follow-up studies after treatment for 4 years Based on clinical data in 200 subjects including Chinese and Caucasian patients. No participants experienced any significant adverse events during the course of treatment. Most patients experienced mild discomfort during venipuncture and some soreness of the arm during apheresis, but discomfort and soreness resolved quickly following the conclusion of the procedure. No tumor formation and other safety concerns in all subjects after receiving closed loop treatment for 4 years.

At each contact with the subject, the investigator must seek information on adverse events by specific questioning and, as appropriate, by examination. Information on all adverse events should be recorded immediately in the source document, and also in the appropriate adverse event module of the case report form (CRF). All clearly related signs, symptoms, and abnormal diagnostic procedures results should recorded in the source document, though should be grouped under one diagnosis.

All adverse events occurring during the study period must be recorded. The clinical course of each event should be followed until resolution, stabilization, or until it has been determined that the study treatment or participation is not the cause. Serious adverse events that are still ongoing at the end of the study period must be followed up to determine the final outcome. Any serious adverse event that occurs after the study period and is considered to be possibly related to the study treatment or study participation should be recorded and reported immediately.

Reporting of Serious Adverse Events and Unanticipated Problems

Investigators and the protocol sponsor must conform to the adverse event reporting timelines, formats and requirements of the various entities to which they are responsible, but at a minimum those events that must be reported are those that are:

Related to study participation,

Unexpected, and

Serious or involve risks to subjects or other.

If the report is supplied as a narrative, the minimum necessary information to be provided at the time of the initial report includes:

Study identifier.

Study Center.

Subject number.

A description of the event.

Date of onset.

Current status.

Whether study treatment was discontinued.

The reason why the event is classified as serious.

Investigator assessment of the association between the event and study treatment.

Investigator Reporting: Notifying the Study Sponsor

Any study-related unanticipated problem posing risk of harm to subjects or others, and any type of serious adverse event, must be reported to the study sponsor by telephone within 24 hours of the event. To report such events, a Serious Adverse Event (SAE) form must be completed by the investigator and faxed to the study sponsor within 24 hours. The investigator will keep a copy of this SAE form on file at the study site.

Within the following 48 hours, the investigator must provide further information on the serious adverse event or the unanticipated problem in the form of a written narrative. This should include a copy of the completed Serious Adverse Event form, and any other diagnostic information that will assist the understanding of the event. Significant new information on ongoing serious adverse events should be provided promptly to the study sponsor.

Investigator Reporting

For reportable deaths, the initial submission to the IRB may be made by contacting the IRB Director or Associate Director. The AE/Unanticipated Problem Form is required as a follow up to the initial submission.

Other Reportable Events:

For clinical drug trials, the following events are also reportable to the IRB:

Any adverse experience that, even without detailed analysis, represents a serious unexpected adverse event that is rare in the absence of drug exposure (such as agranulocytosis, hepatic necrosis, Stevens-Johnson syndrome).

Any adverse event that would cause the sponsor to modify the investigators brochure, protocol or informed consent form, or would prompt other action by the IRB to assure protection of human subjects.

Information that indicates a change to the risks or potential benefits of the research, in terms of severity or frequency. For example:

An interim analysis indicates that participants have a lower rate of response to treatment than initially expected.

Safety monitoring indicates that a particular side effect s more severe, or more frequent than initially expected.

A paper is published from another study that shows that an arm of your research study is of no therapeutic value.

Change in FDA safety labeling or withdrawal from marketing of a drug, device, or biologic used in a research protocol.

Breach of confidentiality.

Change to the protocol taken without prior IRB review t eliminate apparent immediate hazard to a research participant.

Incarceration of a participant when the research was not previously approved under Subpart C and the investigator believes it is in the best interest of the subject to remain on the study.

Complaint of a participant when the complaint indicates unexpected risks or the complaint cannot be resolved by the research team.

Protocol violation (meaning an accidental or unintentional deviation from the IRB approved protocol) that in the opinion of the investigator placed one or more participants at increased risk, or affects the rights or welfare of subjects.

Investigators who are not affiliated with a clinical facility research site are responsible for safety reporting to their local IRB. Investigators are responsible for complying with their local IRB's reporting requirements, though must submit the required reports to their IRB no later than 10 working days. Copies of each report and documentation of IRB notification and receipt will be kept in the investigator's study file.

Sponsor Reporting: Notifying the FDA

If this protocol is being conducted under an FDA IND, it is the responsibility of the study regulatory sponsor, i.e. the IND holder, to report certain adverse events or unanticipated problems to the FDA.

The study sponsor is required to report certain study e ents in an expedited fashion to the FDA. These written notifications of adverse events are referred to as IND safety reports. The following describes the safety reporting requirements by timeline for reporting and associated type of event:

Within 7 calendar days

Any Study Event that is:

Associated with the use of the study drug

Unexpected,

Fatal or life-threatening, and

Within 15 calendar days

Any Study Event that is:

Associated with the use of the study drug,

Unexpected, and

Serious, but not fatal or life-threatening—or—

A previous adverse event that was not initially deemed reportable but is later found to fit the criteria for reporting (reporting within 15 calendar days from when event was deemed reportable).

Any Finding from Tests in Laboratory Animals that:

Suggests a significant risk for human subjects including reports of mutagenicity, teratogenicity, or carcinogenicity.

Sponsors are also required to identify in IND safety reports all previous reports concerning similar adverse events and to analyze the significance of the current event in light of the previous reports.

Reporting Process

Adverse events may be submitted on FDA Form 3500A or in a narrative format. If supplied as in a narrative format, the minimum information to be supplied is noted above.

Sponsor Reporting: Notifying Participating Investigators

It is the responsibility of the study to notify all participating investigators, in a written IND safety report, of any adverse event associated with the use of the drug that is both serious and unexpected, as well as any finding from tests n laboratory animals that suggest a significant risk for human subjects. Additionally, sponsors are also required to identify in IND safety reports all previous reports concerning similar adverse events and to analyze the significance of the current event in light of the previous reports.

Unblinding Procedures

The blind may be broken for a serious and unexpected event if it is essential for the medical management of the subject, or may provide critical safety information about the treatment that could have implications for the ongoing conduct of the trial (e.g., monitoring, informed consent). In those rare instances where it is considered necessary, steps must be in place to reveal the treatment assignment of the patient in question. To report such events, a Serious Adverse Event (SAE) form must be completed. To that end, the investigator must inform the sponsor of all subjects whose treatment was unblended. The unblinding will be 24 hours per day, 7 days a week; notification of sponsor will be within 24 hours by phone or fax, foil wed by a written narrative of the event within 48 hours.

Stopping Rules

In this single-arm study, in which all patients will receive the same experimental treatment at one dose, assesses treatment safety and efficacy. The conduct of this trial may thus be stopped by a stopping rule setting out the circumstances under which the trial will end and the action that will then be taken, if the primary safety endpoint and efficacy endpoints have been achieved, and/or the confirmation of the treatment is safe and efficacious.

Medical Monitoring

It is the responsibility of the Principal Investigator to oversee the safety of the study at his/her site. This safety monitoring will include careful assessment and appropriate reporting of adverse events as noted above, as well as the construction and implementation of a site data and safety-monitoring plan (see Auditing, Monitoring and Inspecting). Medical monitoring will include a regular assessment of the number and type of serious adverse events.

Internal Data and Safety Monitoring Board or DSMP

The initial review of a new protocol lies with the Institutional Review Board (IRB) in reviewing new trials to ensure each trial, regardless of sponsorship or support, contains adequate plans for data and safety monitoring. The Data and Safety Monitoring Board (DSMB) is responsible for monitoring all investigator-initiated trials (IITs) authored by clinical facility investigators, regardless of federal, institutional or industry support. This includes single site IITs, as well as multicenter IITs coordinated by clinical facility investigators with data management and site coordination by the principal investigator and includes all phases of clinical trials conducted at the facility. The members of DSMB at the clinical facility are clinicians, biostatisticians, bioethicists, and research scientists. Where appropriate, the use of an external/independent DSMB for a trial (e.g., high risk, multicenter) will be recommended.

Once a trial is determined as appropriate for monitoring by the internal DSMB, the DSMB has the responsibility for continuing review and monitoring of the study. Our DSMB's review and oversight are written in to the IRB-approved protocol for such trials. The DSMB provides oversight of study progress and safety by review of the following information by un-blinded analysis:

1) Rates of accrual and accrual retention.
2) Frequency and severity of adverse events (AEs) and serious adverse events (SAEs).
3) Response rates, where appropriate.
4) New information related to the trial, i.e., published scientific reports or other developments that may affect subject safety or ethical concerns.
5) Any changes to the anticipated risk/benefit ratio of the study that would affect its continuation.
6) Protocol deviations and violations.
7) Matters that pertain to serious errors or potential misconduct by any of the investigators or research staff, i.e., breaches in confidentiality, research fraud.
8) Subject complaints.
9) Conflict of interest.

The timeline for review of trials by the DSMB is determined at the outset of the study with approval by the IRB. The frequency of DSMB review required for a protocol (i.e., 6 month, yearly) is recorded by the PRMS Administrator and tracked in order that the appropriate DSMB submission documentation is requested from the study team in advance of a scheduled DSMB meeting. The Principal Investigator (PI) and clinical research coordinator (CRC) are provided forms for submission of required documentation to the DSMB.

Data Handlin and Record Keeping

Confidentiality

Information about study subjects will be kept confidential and managed according to the requirements of the Health Insurance Portability and Accountability Act of 1996 (HIPAA). Those regulations require a signed subject authorization informing the subject of the following:

Who will have access to that information and why.

Who will use or disclose that information.

The rights of a research subject to revoke their authorization for use of their PHI.

In the event that a subject revokes authorization to collect or use PHI, the investigator, by regulation, retains the ability to use all information collected prior to the revocation of subject authorization. For subjects that have revoke d authorization to collect or use PHI, attempts should be made to obtain permission to collect at least vital status (i.e. that the subject is alive) at the end of their scheduled study period.

Source Documents

Source data is all information, original records of clinical findings, observations, or other activities in a clinical trial necessary for the reconstruction and evaluation of the trial. Source data are contained in source documents. Examples of these original documents, and data records include: hospital records, clinical and office charts, laboratory notes, memoranda, subjects' diaries or evaluation checklists, pharmacy dispensing records, recorded data from automated instruments, copies or transcriptions certified after verification as being accurate and complete, microfiches, photographic negatives, microfilm or magnetic media, x-rays, subject files, and records kept at the pharmacy, at the laboratories, and at medico-technical departments involved in the clinical trial.

Case Report Forms

The study case report form (CRF) is the primary data collection instrument for the study. All data requested on the CRF must be recorded. All missing data must be explained. If a space on the CRF is left blank because the procedure was not done or the question was not asked, write "N/D". If the item is not applicable to the individual case, write "N/A". All entries should be printed legibly in black ink. If any entry error has been made, to correct such an error, draw a single straight line through the incorrect entry and enter the correct data above it. All such changes must be initialed and dated. DO NOT ERASE OR WHITE OUT ERRORS. For clarification of illegible or uncertain entries, print the clarification above the item, then initial and date it.

Records Retention

It is the investigator's responsibility to retain study essential documents for at least 2 years after the last approval of a marketing application in their country and until there are no pending or contemplated marketing applications in their country or at least 2 years have elapsed since the formal discontinuation of clinical development of the investigational product. These documents should be retained for longer period if required by an agreement with the sponsor. In such an instance, it is the responsibility of the sponsor to inform the investigator/institution as to when these documents no longer need to be retained.

Study Monitoring, Auditing, and Inspecting

Study Monitoring Plan

This study will be monitored in accordance with the monitoring plan.

The investigator will allocate adequate time for such monitoring activities.

The Investigator will also ensure that the monitor or other compliance or quality assurance reviewer is given access to all the above noted study-related documents and study related facilities (e.g. pharmacy, diagnostic laboratory, etc.) and has adequate space to conduct the monitoring visit.

The close-out visit will occur after the last subject's case report forms have been completed, study has been closed with reviewing IRB/IEC and all regulatory issues have been addressed. The following issues will be addressed at this visit: all CRFs have been completed and appropriately filed, a copy of the monitoring Patient Log (is obtained, maintenance and retention of study records.

In summary the Monitor will serve an important role in the successful conduct of the study. The relationship between the Monitor and the site staff is strengthened by open effective communication with the Monitor providing training and support to ensure participants' rights and safety as well as data quality and compliance with all applicable regulations of the regulatory authorities.

Auditing and Inspecting

The investigator will permit study-related monitoring, audits, and inspections by the IRB, the sponsor, government regulatory bodies, and clinical facility compliance and quality assurance groups of all study related documents (e.g. source documents, regulatory documents, data collection instruments, study data etc.). The investigator will ensure the capability for inspections of applicable study-relate facilities (e.g. pharmacy, diagnostic laboratory, etc.).

Participation as an investigator in this study implies acceptance of potential inspection by government regulatory authorities and applicable University compliance and quality assurance offices.

Ethical Considerations

This study is to be conducted according to US and international standards of Good Clinical Practice (FDA Title 21 part 312 and International Conference on Harmonization guidelines), applicable government regulations and Institutional research policies and procedures.

This protocol and any amendments will be submitted to a properly constituted independent Ethics Committee (EC) or Institutional Review Board (IRB), in agreement with local legal prescriptions, for formal approval of the study conduct. The decision of the EC/IRB concerning the conduct of the study will be made in writing to the investigator and a copy of this decision will be provided to the sponsor before commencement of this study. The investigator should provide a list of EC/IRB members and their affiliate to the sponsor.

All subjects for this study will be provided a consent form describing this study and providing sufficient information for subjects to make an informed decision about their participation in this study.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A pharmaceutical composition comprising:

a sterile, enriched population of educated mononuclear cells (EMCs)

wherein the population of EMCs comprises at least 1×10E8 cells;

wherein the population of EMCs comprises a reduced population of $T_{EM}$ cells that express CD4+ and of $T_{EM}$ cells that express CD8+ as compared to an untreated control, wherein the population of EMCs comprises a population of $T_{EM}$ cells with upregulated expression of CCR7 as compared to an untreated control;

wherein the pharmaceutical composition is produced by a method comprising:

(1) isolating peripheral blood from a subject with a disorder with an autoimmune component;

(2) isolating a population of T cells from the peripheral blood isolated from the subject;

(3) co-culturing the isolated population of T cells with adherent umbilical cord mononuclear cells (UC-MNCs) in a bioreactor for at least 17 hours to produce the population of EMCs, wherein the adherent UC-MNCs comprise immature cells of hematopoietic lineage including lymphocytes, monocytes, stem cells (UC-SCs), progenitor cells, mesenchymal stromal cells, and factors derived from umbilical cord blood;

wherein the UC-MNCs are at least 80% confluent;

(4) collecting the population of EMCs; and (5) formulating the population of EMCs into the pharmaceutical composition.

2. The pharmaceutical composition of claim 1, wherein the disorder with the autoimmune component comprises an imbalance of subpopulations of the T cells.

3. The pharmaceutical composition of claim 2, wherein the subpopulations of T cells include a naive T cell subpopulation, an antigen-experienced T cell subpopulation, a regulatory T cell subpopulation ($T_{regs}$), a helper T cell subpopulation, a cytotoxic T cell subpopulation, a central memory T cell subpopulation ($T_{CM}$), and an effector T cell subpopulation ($T_{EM}$), wherein the $T_{EM}$ subpopulation comprises a CD4+$T_{EM}$ subpopulation and a CD8+$T_{EM}$ subpopulation.

4. The pharmaceutical composition according to claim 1, wherein the disorder with the autoimmune component is diabetes.

5. The pharmaceutical composition according to claim 4, wherein the diabetes is type 1 diabetes (T1D) or type 2 diabetes (T2D).

* * * * *